United States Patent
Lin et al.

(10) Patent No.: US 10,500,232 B2
(45) Date of Patent: Dec. 10, 2019

(54) SMALL MOLECULE CELLULAR REPROGRAMMING TO GENERATE NEURONAL CELLS

(71) Applicant: The J. David Gladstone Institutes, a testamentary trust established under the Will of J. David Gladstone, San Francisco, CA (US)

(72) Inventors: Changsheng Lin, San Francisco, CA (US); Sheng Ding, Orinda, CA (US)

(73) Assignee: The J. David Gladstone Ins., a testamentary trust established under the Will of J. David Gladstone, San Francisco, CA (US)

( * ) Notice: Subject to any disclaimer, the term of this patent is extended or adjusted under 35 U.S.C. 154(b) by 0 days.

(21) Appl. No.: 14/913,549

(22) PCT Filed: Aug. 26, 2014

(86) PCT No.: PCT/US2014/052658
§ 371 (c)(1),
(2) Date: Feb. 22, 2016

(87) PCT Pub. No.: WO2015/041809
PCT Pub. Date: Mar. 26, 2015

(65) Prior Publication Data
US 2016/0250260 A1 Sep. 1, 2016

Related U.S. Application Data

(60) Provisional application No. 61/870,088, filed on Aug. 26, 2013.

(51) Int. Cl.
| | | |
|---|---|---|
| A61K 35/30 | (2015.01) | |
| C12N 5/0793 | (2010.01) | |
| A61K 45/06 | (2006.01) | |
| A61K 31/167 | (2006.01) | |
| A61K 31/192 | (2006.01) | |
| A61K 31/198 | (2006.01) | |
| A61K 31/352 | (2006.01) | |
| A61K 31/4015 | (2006.01) | |
| A61K 31/4406 | (2006.01) | |
| A61K 31/4439 | (2006.01) | |
| A61K 31/506 | (2006.01) | |
| A61K 31/688 | (2006.01) | |
| A61K 31/165 | (2006.01) | |
| A61K 31/46 | (2006.01) | |
| A61K 31/196 | (2006.01) | |
| A61K 31/222 | (2006.01) | |
| A61K 31/4402 | (2006.01) | |

(52) U.S. Cl.
CPC ............ *A61K 35/30* (2013.01); *A61K 31/165* (2013.01); *A61K 31/167* (2013.01); *A61K 31/192* (2013.01); *A61K 31/196* (2013.01); *A61K 31/198* (2013.01); *A61K 31/222* (2013.01); *A61K 31/352* (2013.01); *A61K 31/4015* (2013.01); *A61K 31/4402* (2013.01); *A61K 31/4406* (2013.01); *A61K 31/4439* (2013.01); *A61K 31/46* (2013.01); *A61K 31/506* (2013.01); *A61K 31/688* (2013.01); *A61K 45/06* (2013.01); *C12N 5/0619* (2013.01); *C12N 2501/01* (2013.01); *C12N 2501/385* (2013.01); *C12N 2501/395* (2013.01); *C12N 2501/415* (2013.01); *C12N 2501/727* (2013.01); *C12N 2501/999* (2013.01); *C12N 2506/1307* (2013.01)

(58) Field of Classification Search
None
See application file for complete search history.

(56) References Cited

U.S. PATENT DOCUMENTS

2013/0189780 A1    7/2013    Shoemaker et al.

FOREIGN PATENT DOCUMENTS

| WO | WO-2007030697 A2 | 3/2007 |
|---|---|---|
| WO | WO-2010124290 A2 | 10/2010 |
| WO | WO-2012168167 A1 | 12/2012 |
| WO | WO-2015041809 A2 | 3/2015 |
| WO | WO-2015041809 A3 | 3/2015 |

OTHER PUBLICATIONS

Atkinson et al., British J Pharm, 169:269-289, published online Apr. 19, 2012.*
Lu and Atala, Drug Discovery Today, 19(6):801-808, Jun. 2014.*
Hou et al., Science, 341:651-654, Aug. 9, 2013.*
Ferrari et al., Science, 321(5892):1086-1088, Aug. 2008.*
Chaterjee et al, J Neurosci., 33(26):10698-10712, Jun. 26, 2013.*
Zhang et al., J Cell Science, 125:5609-20, Dec. 1, 2012.*
Science, 341:1157, Sep. 13, 2013.*
Pearson et al, Biochim et Biophysica Acta, 1489:354-364, 1999.*
Hegarty et al., Mol and Cell Neurosci, 56:263-271, 2013.*
"International Application Serial No. PCT/US2014/052658, International Search Report dated Apr. 17, 2015", 5 pgs.
"International Application Serial No. PCT/US2014/052658, Written Opinion dated Apr. 17, 2015", 9 pgs.

(Continued)

*Primary Examiner* — Kimberly Ballard
*Assistant Examiner* — Stacey N Macfarlane
(74) *Attorney, Agent, or Firm* — Schwegman Lundberg & Woessner, P.A.

(57) ABSTRACT

Compositions and methods are described herein for chemically inducing cells to change their differentiation state and become neuronal cells.

13 Claims, 49 Drawing Sheets
(41 of 49 Drawing Sheet(s) Filed in Color)
Specification includes a Sequence Listing.

(56) References Cited

OTHER PUBLICATIONS

Lian, Li, et al., "Effects of administration route on migration and distribution of neural progenitor cells transplanted into rats with focal cerebral ischemia, an MRI study", Journal of Cerebral Blood Flow & Metabolism, vol. 30, No. 3,, (Nov. 4, 2009), 653-662.
"European Application Serial No. 14824595.4, Communication Pursuant to Article 94(3) EPC dated May 18, 2017", w/ English Translation, 6 pgs.
"European Application Serial No. 14824595.4, Response filed Oct. 20, 2016 to Communication pursuant to Rules 161(1) and 162 EPC dated Apr. 26, 2016", 8 pgs.
"International Application Serial No. PCT/US2014/052658, International Preliminary Report on Patentability dated Mar. 10, 2016", 10 pgs.
"European Applicatian Serial No. 14824595.4, Communication Pursuant to Article 94(3) EPC dated Jul. 30, 2018", 4 pgs.
"European Applicatian Serial No. 14824595.4, Response filed Apr. 25, 2018 to Communication Pursuant to Article 94(3) EPC dated Jan. 5, 2018", 6 pgs.
"European Application Serial No. 14824595.4, Communication Pursuant to Article 94(3) EPC dated Jan. 5, 2018", 5 pgs.
"European Applicatian Serial No. 14824595.4, Response filed Nov. 30, 2018 to Communication Pursuant to Article 94(3) EPC dated Jul. 30, 2018", 122 pgs.

\* cited by examiner

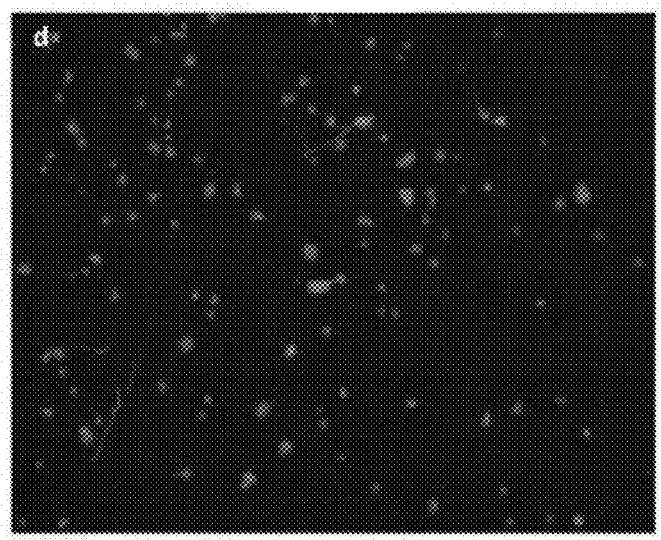
Fig. 1D Ascl1&Myt1l
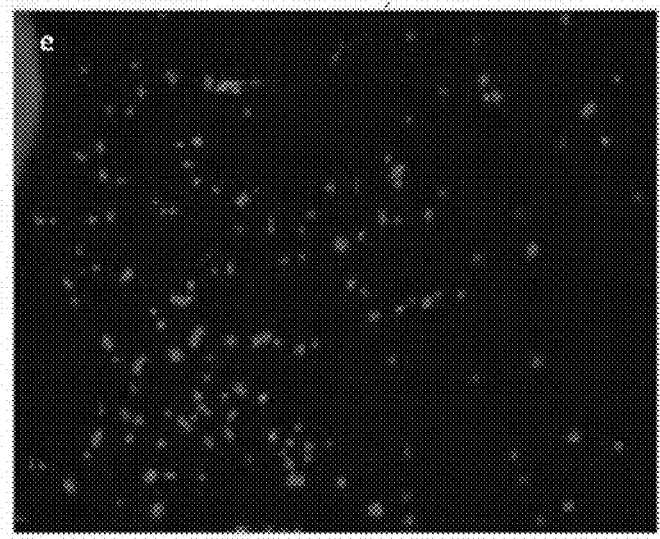
Fig. 1E Ascl1&Brn2
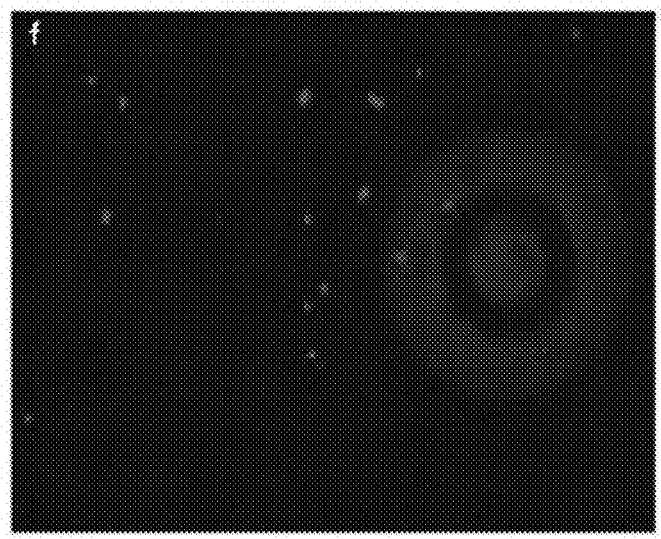
Fig. 1F Brn2&Myt1l

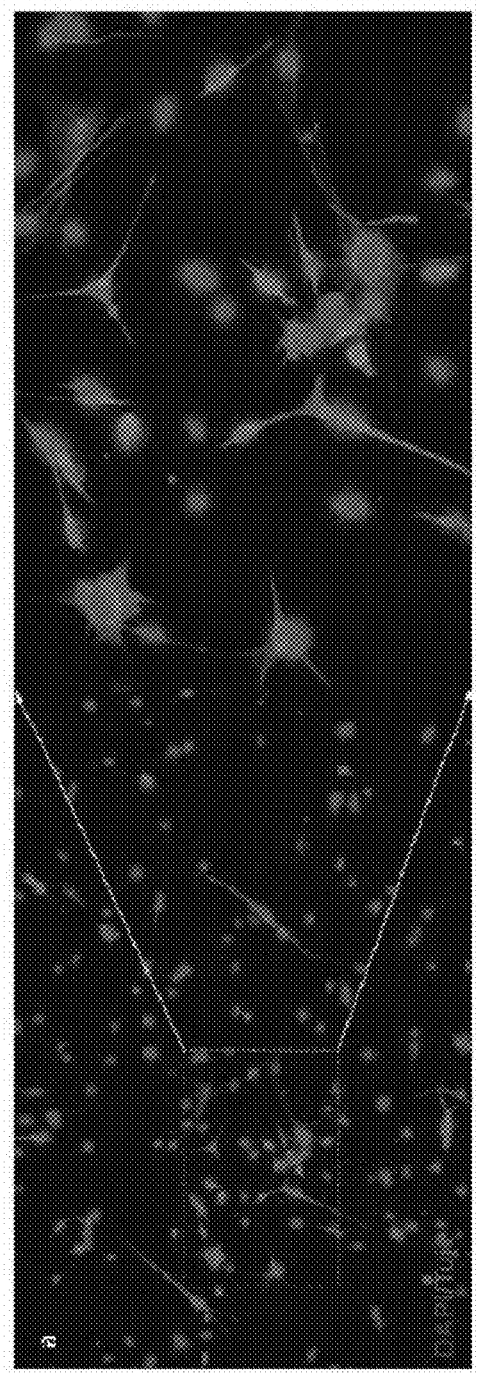
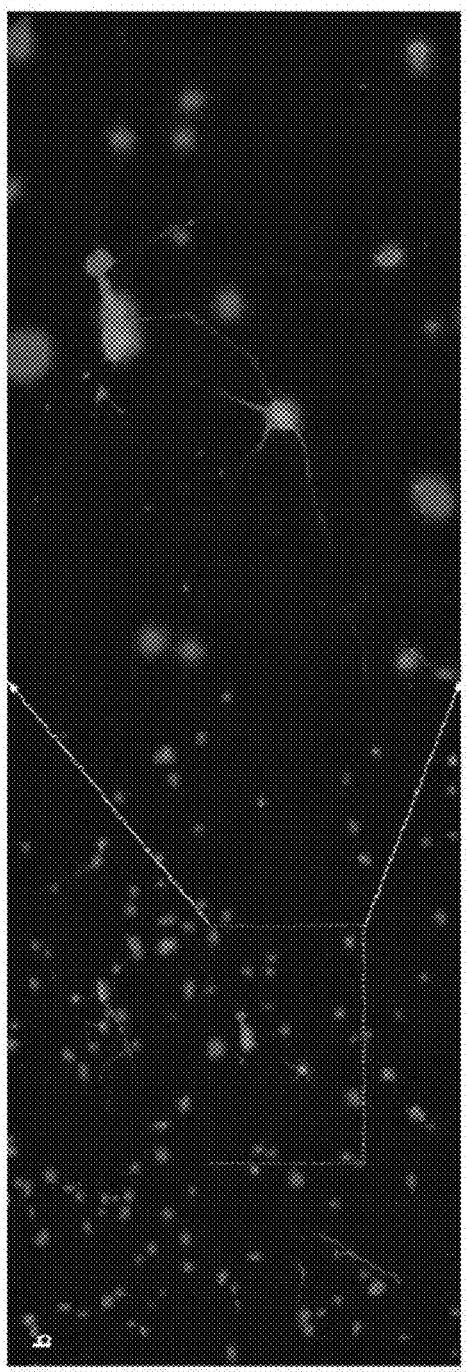
Fig. 2A
Fig. 2B

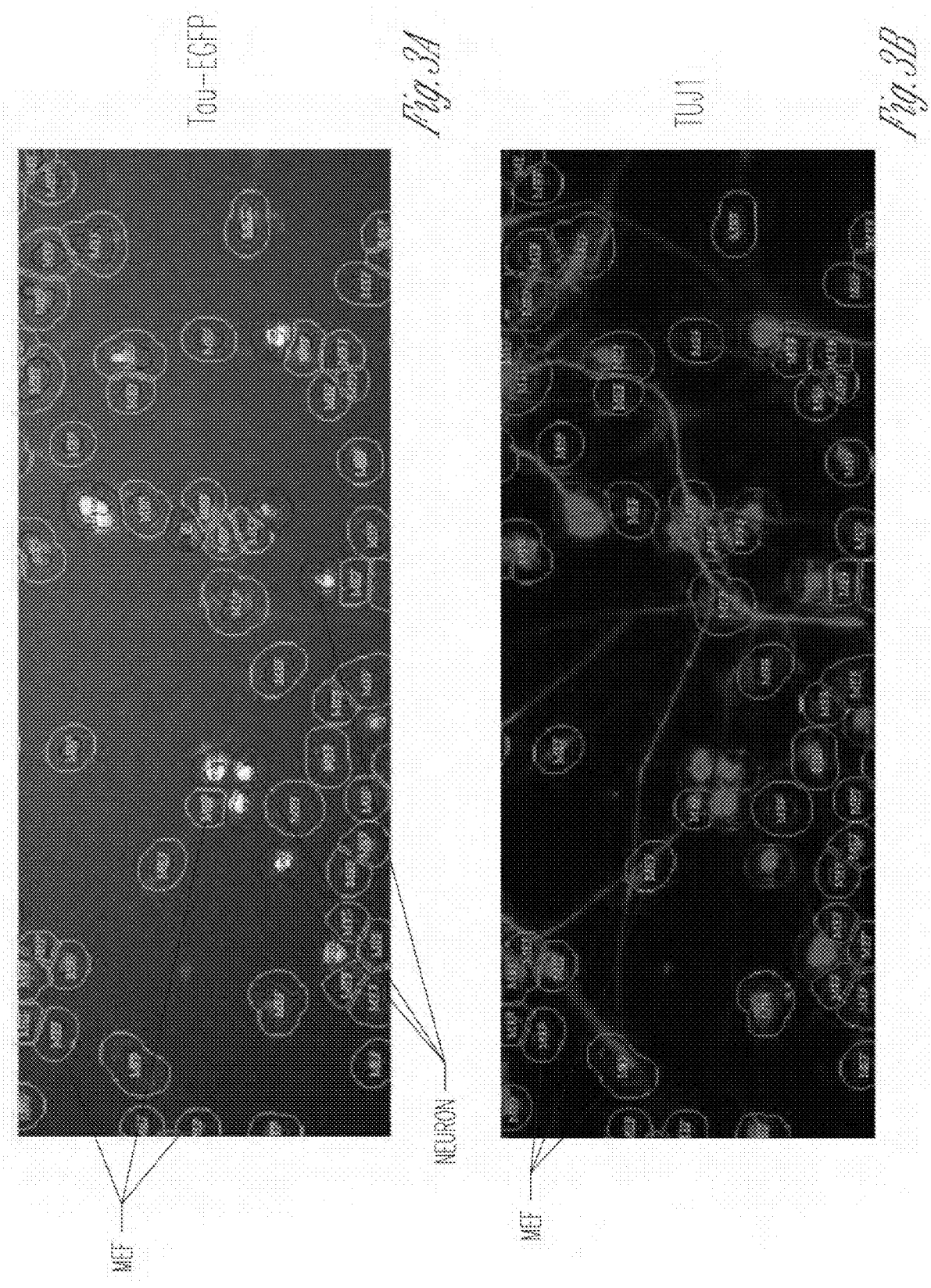

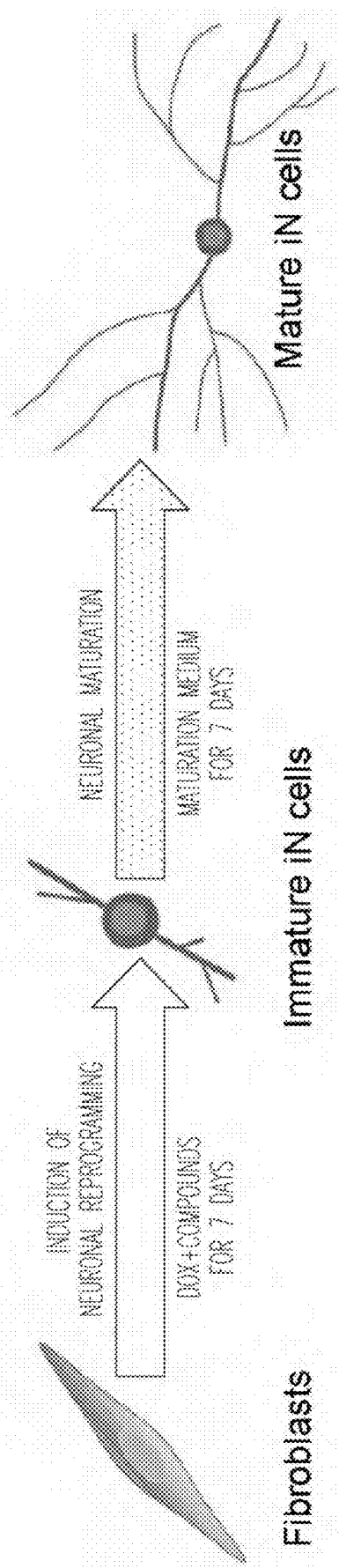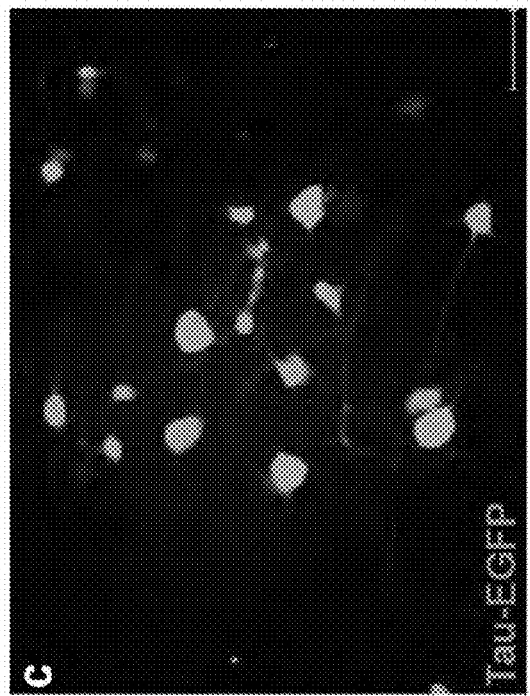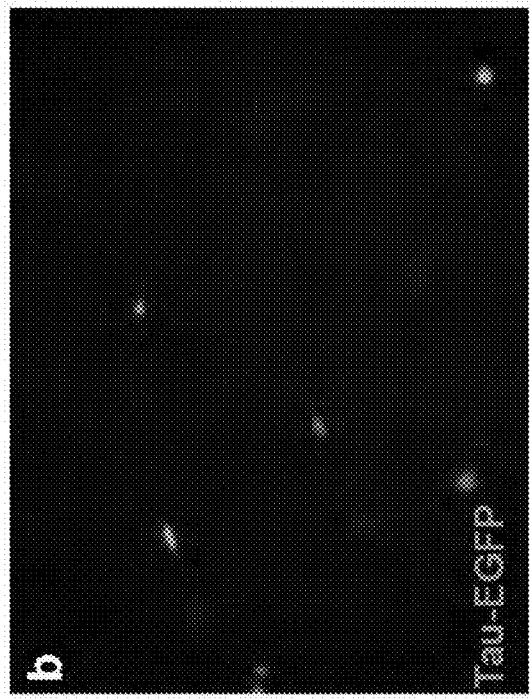

STRC2-AM Cells

Day 9

STRC2-Ascl1 Cells

Day 9

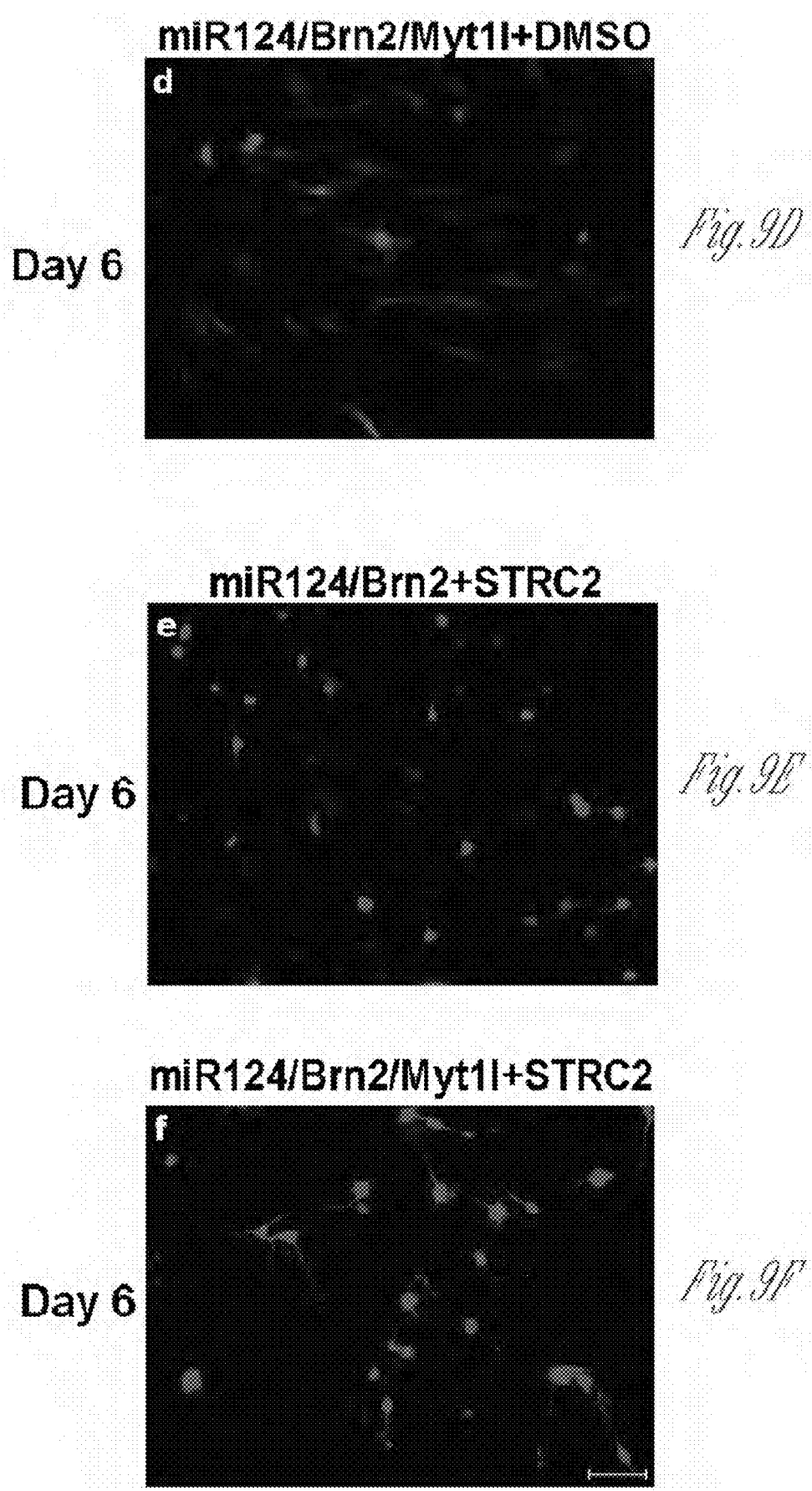

DMSO/miR124-RFP/Brn2

SC/miR124-RFP/Brn2

STRC2/miR124-RFP/Brn2

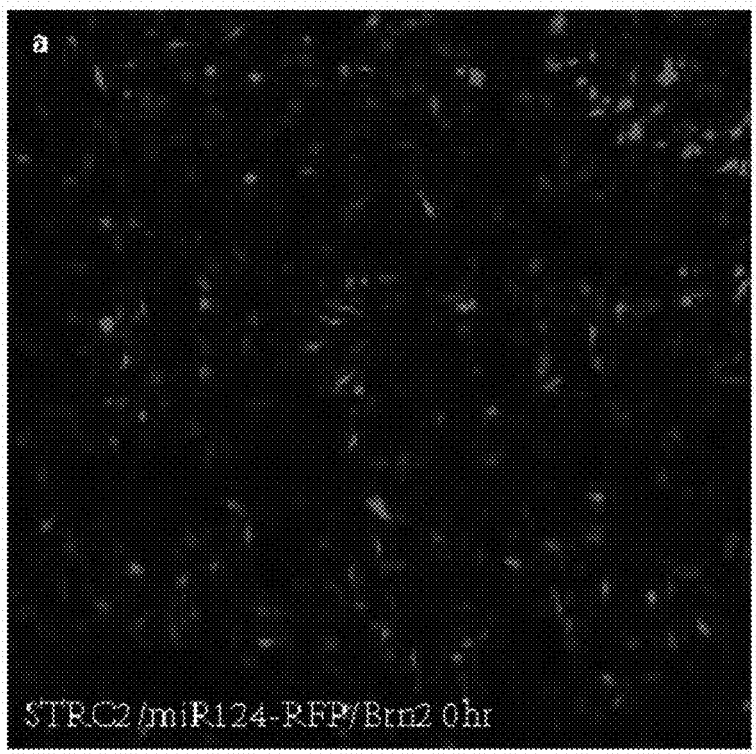
STRC2/miR124-RFP/Brn2 0hr  *Fig.11A*
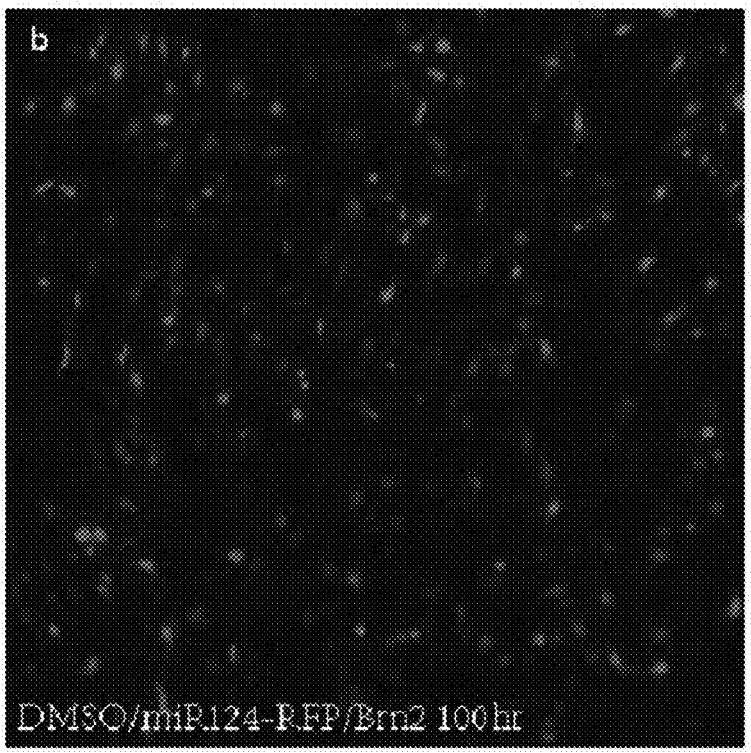
DMSO/miR124-RFP/Brn2 100hr  *Fig.11B*

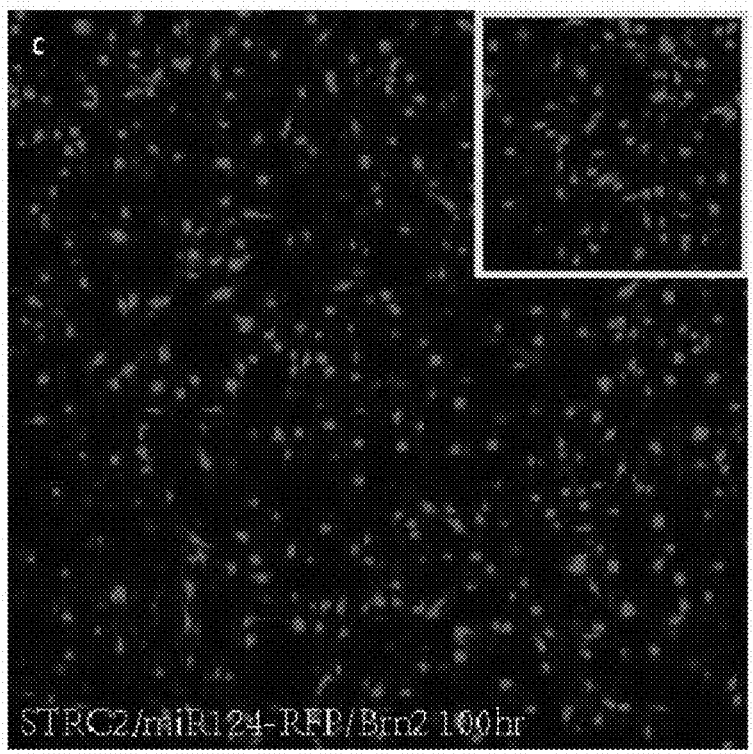
STRC2/miR124-RFP/Brn2 100hr    *Fig. 11C*
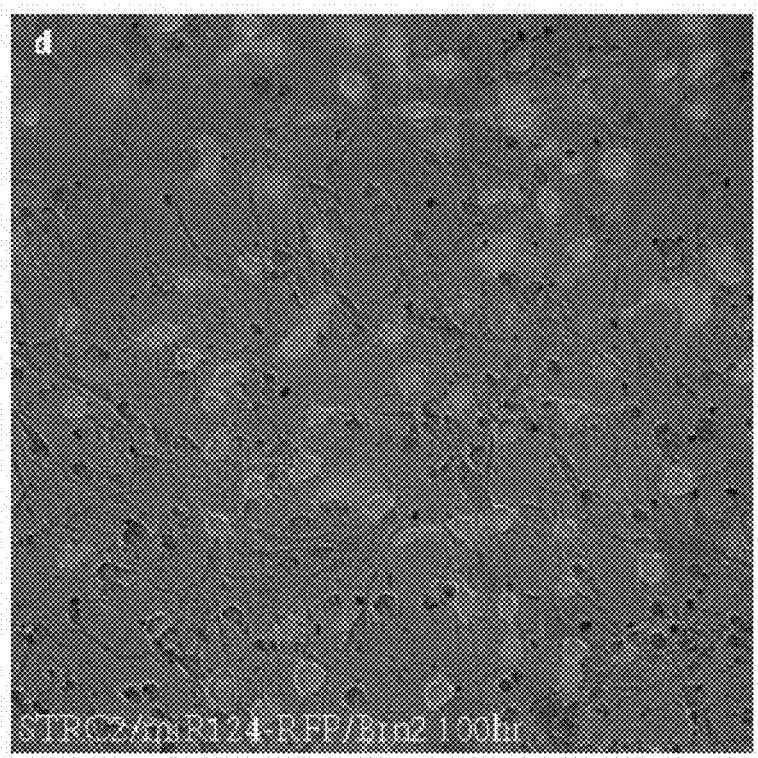
STRC2/miR124-RFP/Brn2 100hr    *Fig. 11D*

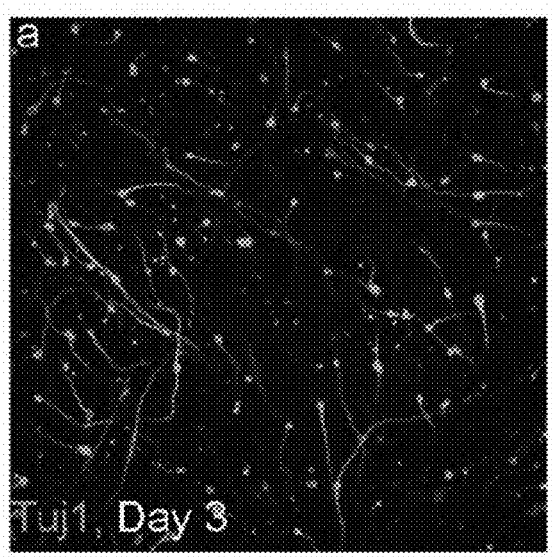
Tuj1, DAY 3  *Fig. 13A*
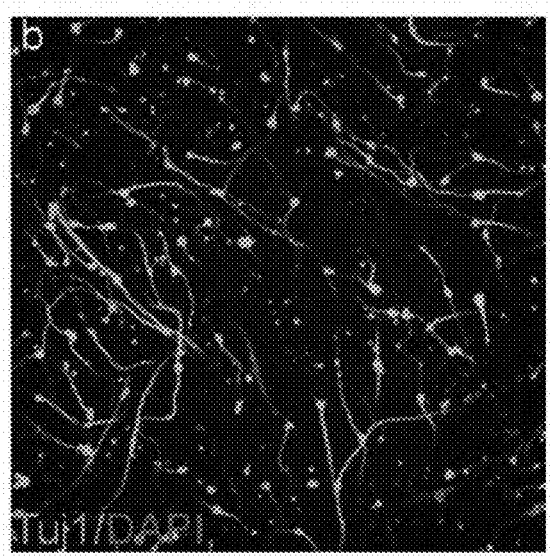
Tuj1/DAPI  *Fig. 13B*

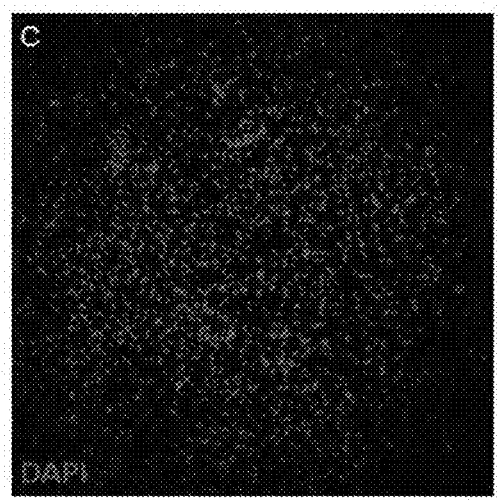
DAPI *Fig. 13C*
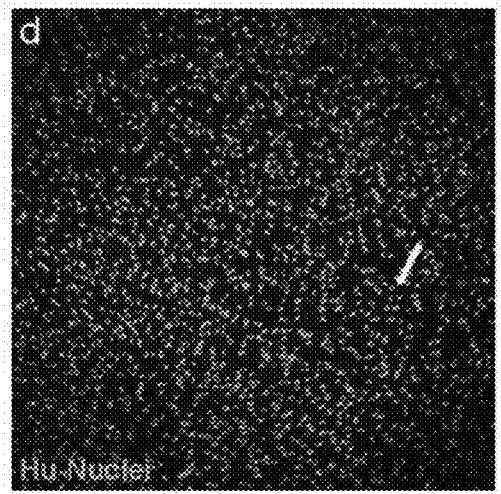
Hu-Nuclei *Fig. 13D*
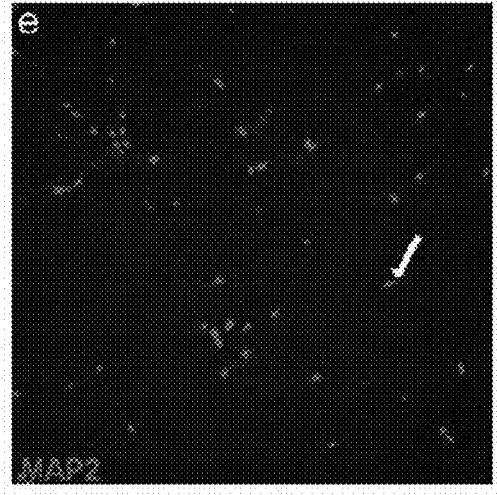
MAP2 *Fig. 13E*

SEQUENCE LISTING

<160> NUMBER OF SEQ ID NOS: 10

<210> SEQ ID NO 1
<211> LENGTH: 85
<212> TYPE: RNA
<213> ORGANISM: Homo sapiens

<400> SEQUENCE: 1
aggccucucu cuccguguuc acagcggacc uugauuuaaa uguccauaca auuaaggcac    60
gcggugaaug ccaagaaugg ggcug                                         85

<210> SEQ ID NO 2
<211> LENGTH: 109
<212> TYPE: RNA
<213> ORGANISM: Homo sapiens

<400> SEQUENCE: 2
aucaagauua gaggcucugc ucuccuguuu cacagcggac cuugauuuaa ugucauacaa    60
uuaaggcacg cggugaaugc caagagcgga gccuacggcu gcacuugaa                109

<210> SEQ ID NO 3
<211> LENGTH: 22
<212> TYPE: RNA
<213> ORGANISM: Homo sapiens

<400> SEQUENCE: 3
cguguucaca gcggaccuug au                                            22

<210> SEQ ID NO 4
<211> LENGTH: 20
<212> TYPE: RNA
<213> ORGANISM: Homo sapiens

<400> SEQUENCE: 4
uaaggcacgc ggugaaugcc                                               20

<210> SEQ ID NO 5
<211> LENGTH: 85
<212> TYPE: RNA
<213> ORGANISM: Mus musculus

```
<400> SEQUENCE: 5
aggccucucu cuccguguuc acagcggacc uugauuuaaa uguccauaca auuaaggcac    60
gcggugaaug ccaagaaugg ggcug                                         85

<210> SEQ ID NO 6
<211> LENGTH: 22
<212> TYPE: RNA
<213> ORGANISM: Mus musculus

<400> SEQUENCE: 6
cguguucaca gcggaccuug au                                            22

<210> SEQ ID NO 7
<211> LENGTH: 20
<212> TYPE: RNA
<213> ORGANISM: Mus musculus

<400> SEQUENCE: 7
uaaggcacgc ggugaaugcc                                               20

<210> SEQ ID NO 8
<211> LENGTH: 87
<212> TYPE: RNA
<213> ORGANISM: Rattus norvegicus

<400> SEQUENCE: 8
ugagggcccc ucugcguguu cacagcggac cuugauuuaa ugucuauaca auuaaggcac    60
gcggugaaug ccaagagagg cgccucc                                       87

<210> SEQ ID NO 9
<211> LENGTH: 22
<212> TYPE: RNA
<213> ORGANISM: Rattus norvegicus

<400> SEQUENCE: 9
cguguucaca gcggaccuug au                                            22

<210> SEQ ID NO 10
<211> LENGTH: 20
<212> TYPE: RNA
<213> ORGANISM: Rattus norvegicus

<400> SEQUENCE: 10
uaaggcacgc ggugaaugcc                                               20
```

SMALL MOLECULE CELLULAR REPROGRAMMING TO GENERATE NEURONAL CELLS

CROSS REFERENCE TO RELATED APPLICATIONS

This application is a U.S. National Stage application filed under 35 U.S.C. § 371 from International Patent Application Serial No. PCT/US2014/052658, filed Aug. 26, 2014, published on Mar. 26, 2015 as WO 2015/041809, which applications claim the benefit of priority to U.S. Provisional patent Application Ser. No. 61/870,088, entitled "Small Molecule Cellular Reprogramming to Generate Neuronal Cells," filed Aug. 26, 2013, the disclosures of which applications are incorporated herein by reference in their entireties.

GOVERNMENT FUNDING STATEMENT

This invention was made with government support under Grant Nos. R01EY021374 and R33MH087908 awarded by the National Institutes of Health. The government has certain rights in the invention.

BACKGROUND

The differentiated cell state is often considered stable and resistant to changes in lineage identity. However, differentiated somatic cell types from humans and other organisms have been reprogrammed to the pluripotent state ("pluripotent reprogramming") by forced expression of a set of transcription factors (Takahashi, K. et al. *Induction of pluripotent stem cells from adult human fibroblasts by defined factors*. Cell 131, 861-872 (2007)), somatic cell nuclear transfer (Campbell et al., *Sheep cloned by nuclear transfer from a cultured cell line*. Nature 380: 64-66 (1996); Gurdon et al., *Sexually mature individuals of Xenopus laevis from the transplantation of single somatic nuclei*, Nature 182, 64-65 (1958)) or cell fusion (Cowan et al., *Nuclear reprogramming of somatic cells after fusion with human embryonic stem cells*, Science (New York, N.7309, 1369-1373 (2005); Tada et al., *Nuclear reprogramming of somatic cells by in vitro hybridization with ES cells*, Curr Biol 11, 1553-1558 (2001)). Additionally, a few studies have demonstrated that through ectopic expression of selected genes or by cell fusion, an adult cell type can be directly converted to another adult cell type (Cobaleda et al., *Conversion of mature B cells into T cells by dedifferentiation to uncommitted progenitors*, Nature 449, 473-477 (2007); Davis et al., *Expression of a single transfected cDNA converts fibroblasts to myoblasts*, Cell 51, 987-1000 (1987); Feng, et al. *PU.1 and C/EBPalpha/beta convert fibroblasts into macrophage-like cells*, Proc. Nat. Acad. Sci. USA 105, 6057-6062 (2008); Ieda et al. *Direct reprogramming of fibroblasts into functional cardiamyocytes by defined factors*, Cell 142, 375-386 (2010); Zhou et al., *In vivo reprogramming of adult pancreatic exocrine cells to beta-cells*, Nature 455, 627-632 (2008); and Zhou, Q. & Melton, D. A. *Extreme makeover: converting one cell into another*, Cell Stem Cell 3, 382-388 (2008)). This process is termed trans-differentiation or lineage reprogramming.

However, major challenges remain due to the low efficiency and slow reprogramming process. A more significant challenge is how to accomplish cell reprogramming without the need for genetic changes in the reprogrammed cells, because such genetic changes give rise to concerns about introduced mutations at the insertion site of expression cassettes encoding pluripotency factors.

SUMMARY

The compositions and methods described herein can accomplish reprogramming of differentiated, non-neuronal cells to generate neural progenitor and mature neuronal cells by chemical means and without the need for genetic engineering. Concerns about introduced genetic mutations are obviated when the compositions and methods described herein are employed. Moreover, use of the compositions and methods described herein is less labor intensive, and less time consuming, than previously available methods.

One aspect of the invention is a composition that includes one or more of the following agents: a GSK3 inhibitor, a WNT agonist, an ALK4/5/7 inhibitor, an HDAC inhibitor, a p300 activator, a PDE4 inhibitor, an Adenylyl cyclase agonist, a retinoic acid receptor γ agonist, a 5-HT3 antagonist, or a metabotropic glutamate (mGlu) receptor agonist. In some embodiments, the composition includes, two or more, or three or more, or four or more, or five or more, or six or more, or seven or more, or eight or more, or nine, or ten of the agents. The composition can include other components, such as those typically found in cell culture media. The composition can be used to generate neuronal cells by in vitro culture of selected cells in the composition. Alternatively, the composition can be administered to a subject. For example, the composition can be administered to a subject orally, parenterally, or to a local site for treatment of a neuronal disease, condition, or injury.

Another aspect of the invention is a method of generating a neuronal cell that includes contacting a selected cell with such a composition, to thereby generate a neuronal progenitor cell. The selected cell contacted with the composition can be a somatic cell, a differentiated cell, a population of cells, a heterogeneous mixture of cells, a non-neuronal cell, or a combination thereof. For example, the selected cell can be a newborn cord blood cell, a newborn stem cell, an adult cell, a fibroblast cell, an epithelial cell, a lymphocyte, or a combination thereof. The selected cell can be an allogenic or autologous cell. The method can further include administering one or more (e.g., a population) of neuronal progenitor cells to an animal. For example, the method can include administering a population of neuronal progenitor cells generated by the methods described herein to a mammal in need thereof.

Another aspect of the invention is a kit that includes any of the compositions described herein, and instructions for using the composition. Such a kit can also include components for in vitro cell culture of a selected cell or a selected population of cells. The kit can also include other components such as one or more cell collection devices, diluents, pharmaceutically acceptable carriers, syringes, catheters, devices for delivery of cells, devices for delivery of the composition, or any combination thereof.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A-1F show that only Ascl1, of the transcription factors tested, could induce expression of the neuronal marker Tuj1 (i.e. β-III-tubulin) in mouse embryonic fibroblast cells. FIG. 1A shows expression of the neuronal marker Tuj1 in mouse embryonic fibroblast cells as induced by only Ascl1. FIG. 1B shows expression of the neuronal marker Tuj1 in mouse embryonic fibroblast cells as induced by only Myt1l. FIG. 1C shows expression of the neuronal marker Tuj1 in mouse embryonic fibroblast cells as induced by only Brn2. FIG. 1D shows expression of the neuronal marker Tuj1 in mouse embryonic fibroblast cells as induced by Ascl1 and Myt1l. FIG. 1E shows expression of the neuronal marker Tuj1 in mouse embryonic fibroblast cells as induced by Ascl1 and Brn2. FIG. 1F shows expression of the neuronal marker Tuj1 in mouse embryonic fibroblast cells as induced by Myt1l and Brn2. One or more transcription factors (Ascl1, Brn2, and/or Myt1l) were introduced into mouse embryonic fibroblasts. After 2 weeks induction by doxycycline, immunostaining was performed by using antibodies against the neuronal marker Tuj1. DAPI was used for nuclei staining.

FIG. 2A-2B illustrates that Ascl1 and Myt1l expression is effective for neuronal reprogramming of mouse embryonic fibroblasts on Day 14. FIG. 2A shows that Ascl1-induced mouse embryonic fibroblasts expressed Tuj1, but did not have neuronal morphology. FIG. 2B shows that Ascl1/Myt1l cells not only expressed Tuj1, but also exhibited typical neuronal morphology.

FIG. 3A-3B shows that the Tau-EGFP signal can be used to define mature neurons. FIG. 3A illustrates that the Tau-EGFP signal is a marker for mature neurons in the analysis of InCell data. FIG. 3B illustrates that only some of Tuj1 positive cells, which have neuronal morphology, are Tau-EGFP positive cells in the analysis. Mouse embryonic fibroblasts are labeled as MEF; lighter stained neuronal cells are labeled as Neur.

FIG. 4A-4T demonstrates that neuronal reprogramming of Ascl1/Myt1l-expressing cells is enhanced by chemically defined conditions. FIG. 4A is a schematic showing of the experimental protocol for chemical reprogramming. FIG. 4B-4D illustrate induction of Tau-EGFP expression in Ascl1/Myt1l-expressing cells treated with DMSO (FIG. 4B) or a cocktail of the following compounds: SB431542, Trichostatin A (TSA), Rolipram, CHIR99021, and CTPB (STRC2; FIG. 4C) for 14 days. FIG. 4D graphically illustrates the percentage of Tau-EGF positive cells after treatment of Ascl1-Myt1l-expressing cells with DMSO or STRC2. The student's t-test was used for comparison of DMSO treated (control) and STRC2 treated cells (p value=0.00039). FIG. 4G-4I show that STRC2-treatment induced expression of neuronal cell markers Tuj1 (FIG. 4G), vGlut1 expression (FIG. 4H) and both Tuj1 and vGlut1 expression (FIG. 4I). FIG. 4J-4L show that STRC2-treatment induced MAP2 expression (FIG. 4J), NeuN expression (FIG. 4K) and both MAP2 plus NeuN expression (FIG. 4L). FIG. 4M-4O show that STRC2 treatment induced GAD65 expression (FIG. 4M), Synapsin I (FIG. 4N), and both GAD65 and Synapsin I (FIG. 4O). Bar 50 µm. FIG. 4T shows spontaneous inhibitory postsynaptic currents (sIPSCs; Vm=0 mV) recorded under voltage clamp. sEPSCs and IPSCs were blocked after addition of 10 mM 2,3-dihydroxy-6-nitro-7-sulfamoylbenzo quinoxaline (NBQX; FIG. FIG. 4S) or 50 mM picrotoxin (FIG. 4T).

FIG. 5A illustrates expression of Tuj1 in Ascl1/Myt1l cells. FIG. 5B illustrates expression of Tuj1 in DAPI stained Ascl1/Myt1l cells.

FIG. 6A shows that Tau-EGFP was expressed in STRC2-treated Ascl1/Myt1l cells at five days after treatment with the STRC2 cocktail. FIG. 6B shows that Tau-EGFP was not yet expressed by day five in STRC2-treated Ascl1-expressing cells (that do not express Myt1l). FIG. 6C shows Tau-EGFP expression in STRC2-treated Ascl1/Myt1l cells at seven days after treatment with the STRC2 cocktail. FIG. 6D shows that STRC2-treated Ascl1 cells began to express Tau-EGFP by Day 7. FIG. 6E shows that Ascl1/Myt1l cells exhibited highly branched neurites by Day 9 after STRC2 treatment. FIG. 6F shows that Ascl1 cells still appeared to be immature neurons on Day 9 after STRC2 treatment.

FIG. 7A-7J illustrate neuronal reprogramming of Ascl1-expressing cells by STRC2 treatment. FIG. 7A shows that DMSO-treated Ascl1-expressing fibroblasts did not express Tau-EGFP and did not exhibit a neuronal morphology at ten days after DMSO treatment. In contrast, FIG. 7B shows that about 0.6% of STRC2-Ascl1 cells were induced to express Tau-EGFP that exhibited a characteristic neuronal morphology at ten days after STRC2 treatment. FIG. 7C graphically illustrates that about 0.7% of Ascl1-expressing cells express Tau-EGFP after incubation with the STRC2 cocktail compared to 0% of Ascl1-expressing cells that were treated with DMSO for fourteen days; the comparison was analyzed using Student's t-test (p value=0.0137). FIG. 7D shows that Tau-EGFP positive cells also expressed vGlut1 at eighteen (18) days after STRC2 treatment, while FIG. 7E shows that the same Tau-EGFP positive cells were also positive for Synapsin I as detected by immunostaining. Bar, 50 µm. FIG. 7F shows a Tau-EGFP positive Ascl1 cell selected for patch clamp. FIG. 7G-7H illustrates that STRC2-Ascl1 cells exhibited trains of action potential after current application and that the cells exhibited typical action current and slow-onset potassium current after step-wise increase of depolarization. FIG. 7I shows that the recorded cells exhibited spontaneous excitatory postsynaptic current (sEPSC) (Vm=−70 mV). FIG. 7J graphically illustrates the percentage of sEPSC among DMSO-treated Ascl1, STRC2-treated Ascl1 and STRC2-treated Ascl1/Myt1l (AM) induced neuronal cells on Day 12 and Day 18 respectively. Student's t-test was applied for the comparison between STRC2-Ascl1 treatment Day 12 and Day 18 (p value=0.00352).

FIG. 8A shows that STRC2-treated Ascl1 cells were converted to Tau-EGFP positive cells by day 10. FIG. 8B shows that these Tau-EGFP cells also expressed MAP2.

FIG. 9A-9F illustrates that neuronal reprogramming of human fibroblasts was enabled and accelerated by STRC2 condition. FIG. 9A illustrates the morphology of miR124-RFP/Brn2/Myt1l cells after DMSO treatment for 2 days. FIG. 9B illustrates the morphology of miR124-RFP/Brn2 cells after STRC2 treatment for 2 days. FIG. 9C illustrates the morphology of miR124-RFP/Brn2/Myt1l cells after STRC2 treatment for 2 days. FIG. 9D illustrates the morphology of miR124-RFP/Brn2/Myt11 cells after DMSO treatment for 6 days. FIG. 9E illustrates the morphology of miR124-RFP/Brn2 cells after STRC2 treatment for 6 days. FIG. 9F illustrates the morphology of miR124-RFP/Brn2/Myt11 cells after STRC2 treatment for 6 days. As shown, the cells exhibited a neuron-like morphology after 2 or 6 days of STRC2 treatment, whereas DMSO treated miR124-RFP/Brn2/Myt11 cells retained morphology of fibroblast cells. Red fluorescent protein (RFP) was indicative of miR124 expression. Bar, 50 µm. FIGS. 9I and 9J show that more than 30% of the miR124-RFP/Brn2 cells were converted into MAP2-positive cells exhibiting characteristic neuronal morphology after 6 days of treatment with STRC2. FIGS. 9L, 9O, and 9R show RFP expression only; while FIGS. 9M, 9P and 9S show expression of Tuj1, NeuN and Synapsin I by the same cells as in FIGS. 9L, 9O, and 9R, respectively. A merged view of the cells shown in FIGS. 9L and 9M is shown in FIG. 9N. Similarly, a merged view of the shown in FIGS. 9O and 9P is shown in FIG. 9Q; and a merged view of the cells shown in FIGS. 9R and 9S is shown in FIG. 9T.

FIG. 10A illustrates that DMSO treatment of miR124-RFP/Brn2 human fibroblasts does not convert the cells to neuronal-like cells. FIG. 10B illustrates that the SB431542 and CHIR99021 (SC condition) also did not affect the morphology of miR124-RFP/Brn2 human fibroblasts. FIG. 10C illustrates that the STRC2 condition was able to convert miR124-RFP/Brn2 human fibroblasts to neuron-like cells within two days of treatment. FIG. 10D shows that by day 6, DMSO treatment had no effect on the morphology of miR124-RFP/Brn2 human fibroblasts no neuronal-like cells were observed. FIG. 10E also shows that even by day 6, treatment with SB431542 and CHIR99021 (SC condition) did not alter the morphology of miR124-RFP/Brn2 human fibroblasts—no neuronal-like cells were observed. However, as shown by FIG. 10F, the STRC2 condition continued to convert significant numbers of miR124-RFP/Brn2 human fibroblasts into neuronal-like cells.

FIG. 11A-11D further illustrate that STRC2 treatment converts significant numbers of miR124-RFP/Brn2 human fibroblasts into neuronal-like cells. FIG. 11A shows miR124-RFP/Brn2 human fibroblasts before STRC2 treatment. FIG. 11B shows that even 100 hours of DMSO treatment miR124-RFP/Brn2 human fibroblasts are not converted into neuronal-like cells. However, FIG. 11C shows that most of miR124-RFP/Brn2 cells were converted to neuron-like cells after 100 hours of STRC2 and doxycycline treatment. FIG. 11D shows an expanded view of the region indicated in FIG. 11C.

FIG. 12A shows a patch clamp of an RFP-positive miR124-RFP/Brn2 cell treated with STRC2 for 6 days. FIG. 12F shows that STRC2 treated miR124-RFP/Brn2 cells express red fluorescent protein (RFP), indicating that the cell expresses microRNA124. FIG. 12G shows that the same STRC2-treated miR124-RFP/Brn2 cell expresses vGlut1. FIG. 12H shows expression of both RFP and vGlut1 in the STRC2 treated miR124-RFP/Brn2 cell shown in FIG. 12F-12G. FIG. 12I shows a different STRC2-treated miR124-RFP/Brn2 cell than shown in FIG. 12F-12H, and that this STRC2-treated miR124-RFP/Brn2 cell also expressed RFP (indicating that this cell also expressed microRNA124). FIG. 12K shows that the same STRC2-treated miR124-RFP/Brn2 cell expresses RFP (FIG. 12I), as well as GlutR2 and GlutR3 (FIG. 12J). FIG. 12K shows expression of both RFP and vGlut1 in the STRC2 treated miR124-RFP/Brn2 cell shown in FIG. 12I-12J. FIG. 12L-12P shows that more than 80% of the human neonatal fibroblasts (hF2097) were converted to Tuj1-positive cells with typical neuronal morphology after 20 days of '9C' treatment. The 9C treatment involved incubation of the cells with the following nine compounds: CHIR99021 (GSK3 inhibitor), SB431542 (ALK4/5/7 inhibitor), MS275 (HDAC1 inhibitor), CTB (p300 activator), Rolipram (PDE4 inhibitor), Forskolin (Adenylyl cyclase agonist), CD1530 (RARγ receptor agonist), TDMB (Tropanyl-3,5-dimethylbenzoate, 5-HT3 antagonist), and ACPD (mGlu receptor agonist). Some cells also expressed NeuN. In contrast, DMSO treated cells (FIGS. 12L and 12O) are negative for both neural markers. FIGS. 12M, 12N, and 12P show that in the absence of other factors (e.g., without induced expression of pluripotency factors such as Oct, Klf, Myc, and/or Sox) most of the hF2097 cells treated with the 9C combination of compounds express Tuj1 and some of them also express NeuN.

FIG. 13A-13G illustrate rapid neuronal conversion of human CCL171 fibroblast cells upon incubation in the 9C composition. FIGS. 13A and 13B show images of CCL171 fibroblasts after treatment with the 9C composition for 3 days. The cells shown in FIGS. 13A and 13B were stained with an antibody against beta-Tubulin III; the cells shown in FIG. 13B were also stained with DAPI. FIGS. 13C-13G show CCL171 fibroblasts treated with the 9C composition for 24 hours and then co-cultured with rat neurons for another 5 days. The cells were fixed and analyzed by immunocytochemistry (ICC) for expression of MAP2 and a human nuclear marker. The arrows point to the 9C induced-neurons derived from human lung CCL171 fibroblasts. FIG. 13C shows DAPI stained CCL171 cells. FIG. 13D shows CCL171 cells stained fora marker of human nuclei. FIG. 13E shows the same cells as shown in FIGS. 13C-13D, stained for MAP2 expression. FIG. 13F shows the same cells as shown in FIGS. 13C-13E, stained for both MAP2 and the human nuclear markers. The inset in FIG. 13F shows a close-up of the cell indicated by the arrow, illustrating expression of both MAP2 and the nuclear marker. FIG. 13G shows the same cells as shown in FIGS. 13C-13F, stained for both DAPI, MAP2 and the human nuclear markers.

DETAILED DESCRIPTION

Figure 1A:
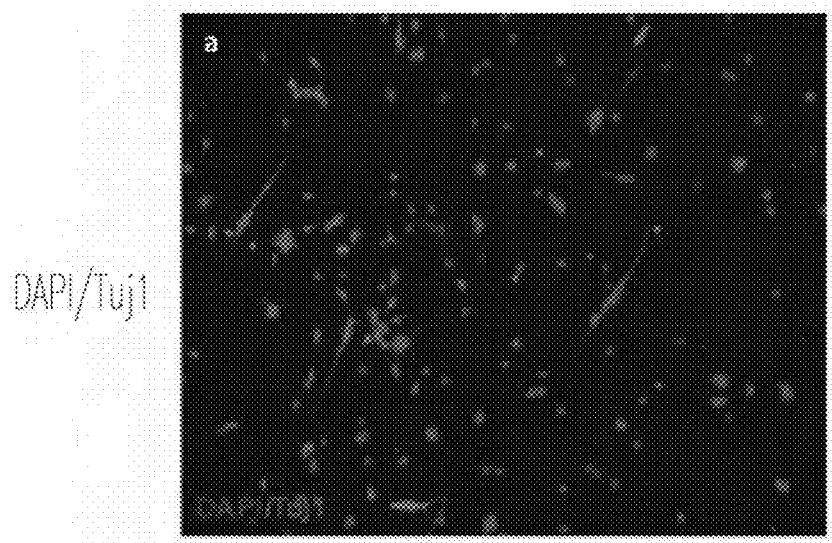

As described herein differentiated non-neuronal, mammalian cells can be reprogrammed to cross lineage boundaries and to directly convert to another cell type, for example a neuronal progenitor cell or a mature functional neuronal cell type, without genetic manipulation. Instead a differentiated non-neuronal cell can simply be treated with a composition of chemical compounds to change that cell into a neuronal cell.

Although one or more recombinantly introduced transcription factors can be used if desired, differentiated mammalian cells can be converted into the neuronal cell lineage without such genetic manipulation. Instead, a composition of chemical compounds can be administered to a subject, or differentiated (e.g., non-neuronal) cells from the subject can be incubated with such a composition to convert the subject's cells to a neuronal cell type. The composition can contain one or more of the following chemical agents: a GSK3 inhibitor, a WNT agonist, a TGF-beta inhibitor, an ALK4/5/7 inhibitor, an HDAC inhibitor, a p300 activator, a PDE4 inhibitor, an Adenylyl cyclase agonist, a retinoic acid receptor γ agonist, a 5-HT3 antagonist, or a metabotropic glutamate (mGlu) receptor agonist. For example, the composition can contain at least two of the agents, or at least three of the agents, or at least four of the agents, or at least five of the agents, or at least six of the agents, or at least seven of the agents, or at least eight of the agents.

In addition, the following compounds can also be useful for reprogramming non-neuronal, mammalian cells to cross lineage boundaries and directly convert a neuronal progenitor or a mature functional neuronal cell type: one or more ROCK inhibitors, one or more neuronal differentiation enhancers, one or more omega-3 fatty acids, one or more A3 adenosine receptor agonists and/or one or more L-type calcium channel blockers. The compositions and methods can, for example, contain one of these types of compounds, or at least two of the compounds, or at least three of the compounds, or at least four of the compounds.

These compounds are described in more detail below.
WNT Agonists

Approximately twenty WNT proteins have been identified in mammals. Examples of WNT proteins include WNT1, WNT2, WNT2b/13, WNT3, WNT3a, WNT4, WNT5a, WNT5b, WNT6, WNT7a, WNT7b, WNT7c, WNT8, WNT8a, WNT8b, WNT8c, WNT10a, Wnt10b, Wnt11, Wnt14, Wnt15, or Wnt16. WNT proteins are secreted, cysteine-rich proteins.

The WNT signaling pathway includes a series of events that occur when a WNT protein binds to a cell-surface receptor of a Frizzled receptor family member. This results in the activation of Dishevelled family proteins which inhibit a complex of proteins that includes axin, GSK-3, and the protein APC to degrade intracellular beta-catenin. The resulting enriched nuclear beta-catenin enhances transcription by TCF/LEF family transcription factors. A WNT agonist can therefore include an agent that activates TCF/LEF-mediated transcription in a cell. WNT agonists can be selected from true WNT agonists that bind and activate a Frizzled receptor family member including any and all of the WNT family proteins, an inhibitor of intracellular beta-catenin degradation, activators of TCF/LEF, and inhibitors of GSK-3.

Activation of the WNT pathway leads to inhibition of GSK3, subsequent nuclear accumulation of β-catenin and the expression of target genes. WNT agonists can include WNT-3a, a GSK-inhibitor (such as any of those described herein), WNT 5, WNT-6a, Norrin, and any other WNT family protein.

For example, a WNT agonist can include a secreted glycoprotein including WNT-1/Int-1, WNT-2/Irp (InM-related Protein), WNT-2b/13, WNT-3/Int-4, WNT-3a (R&D Systems), WNT-4, WNT-5a, WNT-5b, WNT-6 (Kirikoshi et al., *Biochem Biophys Res Com* 283: 798-805 (2001)), WNT-7a (R&D systems), WNT-7b, WNT-8a/8d, WNT-8b, WNT-9a/14, MINT- 9b/14b/15, WNT-10a, WNT-10b/12, WnM 1, and Wnt-16. An overview of human WNT proteins is provided in "THE WNT FAMILY OF SECRETED PROTEINS", R&D Systems Catalog, 2004. Other WNT agonists include the R-spondin family of secreted proteins, which is implicated in the activation and regulation of WNT signaling pathway. The R-spondin family of secreted proteins has four members (R-spondin 1 (NU206, Nuvelo, San Carlos, Calif.), R-spondin 2 (R&D systems), R-spondin 3, and R-spondin 4). Another WNT agonist is Norrin (also called Nome Disease Protein or NDP) (R&D systems), which is a secreted regulatory protein that functions like a WNT protein in that it binds with high affinity to the Frizzled-4 receptor and induces activation of the WNT signaling pathway (Kestutis Planutis et al., *BMC Cell Biol* 8-12 (2007)). In some embodiments, one or more WNT agonists can include an R-spondin mimic, for example an agonist of Lgr5 such as an anti-Lgr5 antibody. A small-molecule agonist of the WNT signaling pathway, an aminopyrimidine derivative, was recently identified and is also expressly included as a WNT agonist (Lin et al. *Angew Chem Int Ed Engl* 44, 1987-90 (2005)).

In some embodiments, the WNT agonist is a GSK-inhibitor.

One or more WNT agonists can be included in a composition for treatment of a subject. Alternatively, one or more WNT agonists can be included in a cell medium useful for reprogramming a differentiated cell into a neuronal cell type.

The WNT agonists can be employed in the compositions and methods described herein in a variety of amounts and/or concentrations. For example, the WNT agonists can be employed in a solution at a concentration of about 0.01 micromolar to about 20 millimolar. In a dry formulation, the WNT agonists can be present in amounts of about 0.01 mg to about 100 mg, or about 0.05 mg to about 10 mg, or about 0.1 mg to about 1.0 mg.

GSK3 Inhibitors

Glycogen synthase kinase 3 (GSK3) is a serine/threonine protein kinase that catalyzes the addition of phosphate molecules on certain serine and threonine amino acid residues in target protein substrates within cells. Phosphorylation of such target protein substrates often results in the modification of their specific activities or function.

As illustrated herein GSK3 inhibitors can facilitate reprogramming of differentiated cells to neuronal lineage. Examples of GSK3 inhibitors that can be employed include one or more of the following compounds:

CHIR99021 (6-(2-(4-(2,4-dichlorophenyl)-5-(4-methyl-1H-imidazol-2-yl)pyrimidin-2-ylamino)ethylamino) nicotinonitrile);

1-azakenpaullone (9-Bromo-7,12-dihydro-pyrido[3',2':2,3]azepino[4,5-b]indol-6(5H)-one), BIO ((2'Z,3'E)-6-Bromoindirubin-3'-oxime);

AR-A014418 (N-(4-Methoxybenzyl)-N'-(5-nitro-1,3-thiazol-2-yl)urea);

Indirubin-3'-monoxime;

5-Iodo-indirubin-3'-monoxime;

kenpaullone (9-Bronco-7,12-dihydroindolo-[3,2-d][1]benzazepin-6(5H)-one);

SB-415286 (3-[(3-Chloro-4-hydroxyphenyl)amino]-4-(2-nitro-phenyl)-1H-pyrrole-2,5-dione);

SB-216763 (3-(2,4-Dichlorophenyl)-4-(1-methyl-1H-indol-3-yl)-1H-pyrrole-2,5-dione);

Maybridge SEW00923SC (2-anilino-5-phenyl-1,3,4-oxadiazole);

(Z)-5-(2,3-Memylenedioxyphenyl)imidazolidine-2,4-dione,

TWS119 (3-(6-(3-aminophenyl)-7H-pyrrolo[2,3-d]pyrimidin-4-yloxy)phenol);

CHIR98014 (N2-(2-(4-(2,4-dichlorophenyl)-5-(1H-imidazol-1-yl)pyrimidin-2-ylamino)ethyl)-5-nitropyridine-2,6-diamine);

SB415286 (3-(3-chloro-4-hydroxyphenylamino)-4-(2-nitrophenyl)-1H-pyrrole-2,5-dione);

Tideglusib (also known as NP031112, or NP-12; 1,2,4-Thiadiazolidine-3,5-dione, 2-(1-naphthalenyl)-4-(phenylmethyl));

LY2090314 (1H-Pyrrole-2,5-dione, 3-imidazo[1,2-a]pyridin-3-yl-4-[1,2,3,4-tetrahydro-2-(1-piperidinylcarbonyl)pyrrolo[3,2,1-jk][1,4]benzodiazepin-7-yl]);

lithium salt (e.g., LiCl); or any combination thereof.

GSK-inhibitors can also include small-interfering RNAs (siRNA, Cell Signaling), lithium (Sigma), kenpaullone (Biomol International, Leost, Metal (2000) *Eur J Biochem* 267, 5983-5994), 6-Bromoindirubin-30-acetoxime (Meyer, L et al (2003) *Chem Biol* 10, 1255-1266), SB 216763 and SB 415286 (Sigma-Aldrich), and FRAT-family members and FRAT-derived peptides that prevent interaction of GSK-3 with axin. An overview is provided by Meijer et al, (2004) *Trends in Pharmacological Sciences* 25, 471-480, which is hereby incorporated by reference in its entirety. GSK3 inhibitors that can be used in the compositions and methods described herein can also include those disclosed in US 20120329152 by Pera et al., which is specifically incorporated herein in its entirety.

The GSK3 inhibitor can, for example, be CHIR99021, SB216763, TWS119, CHIR98014, Tideglusib, SB415286, LY2090314, or any combination thereof. In some embodiments, the GSK3 inhibitor can be CHIR99021.

The GSK3 inhibitor can be employed in the compositions and methods described herein in a variety of amounts and/or concentrations. For example, the GSK3 inhibitor can be employed at a concentration of about 0.01 micromolar to about 20 millimolar in a solution. In a dry formulation, the GSK3 inhibitor can be present in amounts of about 0.01 mg to about 100 mg, or about 0.05 mg to about 10 mg, or about 0.1 mg to about 1.0 mg.

Methods and assays for determining a level of GSK-3 inhibition are available to a skilled person and include, for example, the methods and assays described in Liao et al., *Endocrinology*, 145(6): 2941-2949 (2004); and in U.S. Pat. No. 8,323,919, both of which are specifically incorporated by reference herein in their entireties.

TCF-Beta Inhibitors

As illustrated herein use of one or more transforming growth factor-beta (TGF-β) inhibitors can facilitate conversion of differentiated cells into the neuronal cell lineage.

There are about thirty members of the transforming growth factor-beta (TGF-β) superfamily, including activin, Nodal, and BMPs. These TGF-β family members elicit their responses through a variety of cell surface receptors that activate Smad protein signaling cascades.

A TGF-beta inhibitor can directly or indirectly, negatively regulate TGF-beta signaling. In some embodiments, one or more TGF-beta inhibitors binds to and reduces the activity of one or more serine/threonine protein kinases selected from the group consisting of ALK5, ALK4, TGF-beta receptor kinase 1 and ALK7. ALK4, ALK5 and ALK7 are all closely related receptors of the TGF-beta superfamily. Desirable TGF-beta inhibitors can bind to and reduce the activity of ALK4, ALK5 (TGF-beta receptor kinase 1) and/or ALK7. In another embodiment, the TGF-beta receptor binds to and reduces the activity of a Smad protein, for example R-SMAD or SMADI-5 (i.e. SMAD 1, SMAD 2, SMAD 3, SMAD 4 or SMAD 5).

Examples of TGF-B inhibitors include, but are not limited to:

4-[4-(1,3-benzodioxol-5-yl)-5-(2-pyridinyl)-1H-imidazol-2-yl]benzamide (also known as SB 431542 from Tocris Bioscience; a potent and selective inhibitor of TGF-β type I receptor activin receptor-like kinase ALK5 (e.g., with $IC_{50}$ =94 nM), and its relatives ALK4 and ALK7);

3-(6-Methyl-2-pyridinyl)-N-phenyl-4-(4-quinolinyl)-1H-pyrazole-1-carbothioamide (also known as A83-01 from Tocris Bioscience; a selective inhibitor of TGF-β type I receptor ALK5 kinase, type I activin/nodal receptor ALK4 and type I nodal receptor ALK7 (IC50 values can, e.g., be 12, 45 and 7.5 nM respectively);

2-(3-(6-Methylpyridine-2-yl)-IH-pyrazol-4-yl)-1,5-naphthyridine (also known as SJN 2511 from Tocris Bioscience; selective inhibitor of the TGF-β type I receptor ALK5 (IC50 values can, e.g., be 0.004 and 0.023 μM for ALK5 autophosphorylation and ALK5 binding, respectively);

4-[4-(2,3-Dihydro-1,4-benzodioxin-6-yl)-5-(2-pyridinyl)-IH-imidazol-2-yl]benzamide (also known as D 4476 from Tocris Bioscience; a selective inhibitor of casein kinase 1 (CK1) and TGF-β type-1 receptor (ALK5) that displays greater than 20-fold selectivity over SAPK2/p38);

4-[3-(2-Pyridinyl)-1H-pyrazol-4-yl]-quinoline (also known as LY 364947 from Tocris Bioscience; a selective inhibitor of TGF-β type-I receptor (TGF-β R1, TGFR-I, TβR-1, ALK-5) (IC50 values can, e.g., be 59, 400 and 1400 nM for TGR-β RI, TGF-β RII and MLK-7K respectively);

2-(4-(benzo[d][1,3]dioxol-5-yl)-2-tert-butyl-1H-imidazol-5-yl)-6-methylpyridine (also known as SB505124, and available from Selleckchem.com; a selective inhibitor of ALK4 and ALK5 (e.g., with IC50 of 129 nM and 47 nM, respectively);

6-[2-(1,1-Dimethylethyl)-5-(6-methyl-2-pyridinyl)-1H-imidazol-4-yl]quinoxaline (also known as SB 525334 from Sigma-Aldrich; a selective inhibitor of transforming growth factor-β receptor I (ALK5, TGF-βRI), with IC50=14.3 nM, for example);

2-(5-Chloro-2-fluorophenyl)-4-[(4-pyridyl)amino]pteridine (also known as SD 208 from Tocris Bioscience; a potent, orally active ATP-competitive transforming growth factor- 2 receptor 1 (TGF-βRI) inhibitor, e.g., with IC50=49 nanomolar);

4-(6-(4-(piperazin-1-yl)phenyl)pyrazol[1,5-a]pyrimidin-3-yl)quinoline (also known as LDN-193189 from Miltenyi Biotec); and any combination thereof.

The inhibitor that directly or indirectly negatively regulates TGF-beta signaling can, for example, be selected from the group consisting of SB-431542, A83-01, SJN-2511, LY-36494, SB-505124, SB-525334, and SD-208. In some embodiments, the inhibitor that directly or indirectly negatively regulates TGF-beta signaling can inhibit ALK4, ALK5 and/or ALK7. For example, the inhibitor that directly or indirectly negatively regulates TGF-beta signaling can be SB-431542.

The TGF-beta inhibitor can be employed in the compositions and methods described herein in a variety of amounts and/or concentrations. For example, the TGF-beta inhibitor can be employed at a concentration of about 0.01 micromolar to about 20 millimolar in a solution. In a dry formulation, the TGF-beta inhibitor can be present in amounts of about 0.01 mg to about 200 mg, or about 0.05 mg to about 100 mg, or about 0.1 mg to about 20 mg.

Various methods for determining if a substance is a TGF-beta inhibitor are known. For example, a cellular assay may be used, in which cells are stably transfected with a reporter construct comprising the human PAI-1 promoter or Smad binding sites, driving a luciferase reporter gene. Inhibition of luciferase activity relative to control groups can be used as a measure of compound activity (De Gouville et al., *Br J Pharmacol.* 2005 May; 145(2): 166-177). Another example is the ALPHASCREEN® phosphosensor assay for measurement of kinase activity (Drew A E et al., Comparison of 2 Cell-Based Phosphoprotein Assays to Support Screening and Development of an ALK Inhibitor *J Biomol Screen* 16(2) 164-173, 2011).

HDAC1 Inhibitor

Histone deacetylases (HDAC) are a class of enzymes that remove acetyl groups from an ε-N-acetyl lysine amino acid on a histone. Exemplary HDACs include those of Class I HDAC: HDAC1, HDAC2, HDAC3, HDAC8; and Class II HDACs: HDAC4, HDAC5, HDAC6, HDAC7A, HDAC9, HDAC10. Type I mammalian HIDACs include: HDAC1, HDAC2, HDAC3, HDAC8, and HDAC11. Type II mammalian HDACs include: HDAC4, HDAC5, HDAC6, HDAC7, HDAC9, and HDAC10.

As illustrated herein use of one or more histone deacetylase inhibitors can facilitate conversion of differentiated cells into the neuronal cell lineage. The histone deacetylase inhibitors can inhibit one or more of these histone deacetylases. In some instances the histone deacetylase inhibitors are inhibitors of HDAC1.

Inhibitors of HDACs (HDAC inhibitors) can include, for example, small molecular weight carboxylates (e.g., less than about 250 amu), hydroxamic acids, benzamides, epoxyketones, cyclic peptides, and hybrid molecules. (See, for example, Drummond et al., *Annu Rev Pharmacol Toxicol* 45: 495-528 (2005), (including specific examples therein) which is hereby incorporated by reference in its entirety). Non-limiting examples of negative regulators of type I/II HDACs include:

Suberoylanilide Hydroxamic Acid (SAHA: also called Vorinostat and MK0683), which inhibits the activities of HDAC1 and HDAC3, for example, with IC50 values of about 10 nM and 20 nM, respectively;

BML-210 (N1-(2-aminophenyl)-N8-phenyl-octanediamide, available from Sigma-Aldrich); in HeLa extracts, the IC50 of BML-210 for inhibition of HDAC activity can, for example, be about 80 μM;

Depudecin (e.g., (−)-Depudecin; 4,5:8,9-Dianhydro-1,2,6,7,11-pentadeoxy-D-threo-D-ido-undeca-1,6-dienitol), which can, for example, have an IC50 for HDAC1 of about 4.7 μM;

HC Toxin ((6R,9S,14aR)-3,6R-dimethyl-9S-(7-((S)-oxiran-2-yl)-7-oxoheptyl)decahydropyrrolo[1,2-a][1,4,7,10]tetraazacyclododecine-1,4,7,10-tetranone, available from Cayman Chemical); HC Toxin is a cell-permeable, reversible inhibitor of histone deacetylases (HDACs) (e.g., $IC_{50}$=30 nM);

Scriptaid (N-Hydroxy-1,3-dioxo-1H-benz[de]isoquinoline-2(3H)-hexananmide);

Phenylbutyrate (e.g., sodium phenylbutyrate), Sodium Butyrate, pivaloyloxymethyl butyrate (Pivanex, AN-9);

Valproic Acid ((VPA) and other short chain fatty acids), Suramin (e.g., Suramin Sodium);

Trichostatin A (TSA; (R,2E,4E)-6-(4-(dimethylamino)benzoyl)-N-hydroxy-4-methylhepta-2,4-dienamide), for example, with an IC50 of about 1.8 nM;

APHA Compound 8 (3-(1-Methyl-4-phenylacetyl-1H-2-pyrrolyl)-N-hydroxy-2-propenamide), which is HDAC class I-selective;

Apicidin (Cyclo[(2S)-2-Amino-8-oxodecanoyl-1-methoxy-L-tryptophyl-L-isoleucyl-(2R)-2-piperidinecarbonyl]), which is a potent histone deacetylase with, for example, an IC50=0.7 nM;

Trapoxin B (3,6-dibenzyl-9-[6-(oxiran-2-yl)-6-oxohexyl]-1,4,7,10-tetrazabicyclo[10.3.0]pentadecane-2,5,8,11-tetrone), an HDAC1 inhibitor with, for example, an IC50 of about 0.1 nM;

Chlamydocin ((3R)-3-benzyl-6,6-dimethyl-9-[6-[(2R)-oxiran-2-yl]-6-oxohexyl]-1,4,7,10-tetrazabicyclo[10.3.0]pentadecane-2,5,8,11-tetrone), with, for example, an IC50 of about 0.15 nM;

Depsipeptide (also known as romidepsin, FR901228 or FK228; (1S,4S,7Z,10S,16E,21R)-7-ethylidene-4,21-di(propan-2-yl)-2-oxa-12,13-dithia-5,8,20,23-tetrazabicyclo[8.7.6]tricos-16-ene-3,6,9,19,22- pentone);

CI-994 (also known as acetyldinaline or Tacedinaline; 4-acetamido-N-(2-aminophenyl)benzamide), with, for example, a Ki of 0.05 for HDAC1;

MS-27-275 (also known as MS275 or entinostat; pyridin-3-ylmethyl-N-[[4-[(2-aminophenyl)carbamoyl]phenyl]methyl]carbamate), with, for example, an IC50 of about 0.1-1 μM;

MGCD0103 (also known as Mocetinostat, N-(2-aminophenyl)-4-[[(4-pyridin-3-ylpyrimidin-2-yl)amino]methyl]benzamide), with, for example, an IC50 of about 0.1 μM;

NVP-LAQ-824 (also known as Dacinostat or LAQ824, (E)-N-hydroxy-3-[4-[[2-hydroxyethyl-[2-(1H-indol-3-yl)ethyl]amino]methyl]phenyl]prop-2-enamide), with, for example, an IC50 for HDAC1 of about 0.003-0.008 μM;

CBHA (also known as m-carboxycinnaminic acid bishydroxamic acid; N-hydroxy-3-[(E)-3-(hydroxyamino)-3-oxoprop-1-enyl]benzamide);

JNJ16241199 (also known as R306465; N-hydroxy-2-(4-(naphthalen-2-ylsulfonyl)piperazin-1-yl)pyrimidine-5-carboxamide), a potent inhibitor of HDAC1 with, for example, IC50 values of about 30 to 300 nM;

Tubacin (also known as 537049-40-4, AC1O7Y2P, CHEMBL356769, CTK8E6516, DIOX-H_003551, Y6280; N-[4-[(2R,4R,6S)-4-[(4,5-diphenyl-1,3-oxazol-2-yl)sulfanylmethyl]-6-[4-(hydroxymethyl)phenyl]-1,3-dioxan-2-yl]phenyl]-N'-hydroxyoctanediamide), with, for example, a Ki for HDAC1 of about 0.028 µM;

A-161906 (7-[4-(4-cyanophenyl)phenoxy]-heptanohydroxamic acid);

Proxamide (see WO2007031853A2);

Oxamflatin ((E)-5-[3-(benzenesulfonamido)phenyl]-N-hydroxypent-2-en-4-ynamide);

3C1-UCHA (6-(3-chlorophenylureido)caproic hydroxamic acid);

AOE (2-amino-8-oxo-9,10-epoxydecanoic acid);

CHAP31 ((2S)-N'-hydroxy-N-[(2R)-3-(4-methoxyphenyl)-1-[[(2S,3R)-3-methyl-1-oxopentan-2-yl]amino]-1-oxopropan-2-yl]-2-(pyrrolidine-2-carbonylamino) octanediamide); or any combination thereof.

See WO2007031853A2, which is incorporated by reference herein in its entirety, for structures of many of these HDAC inhibitors.

Other inhibitors include, for example, dominant negative forms of the HDACs (e.g., catalytically inactive forms), siRNA inhibitors of the HDACs, and antibodies that specifically bind to the HDACs. Inhibitors are available, e.g., from BIOMOL International, Fukasawa, Merck Biosciences, Novartis, Gloucester Pharmaceuticals, Aton Pharma, Than Pharmaceuticals, Schering AG, Pharmion, MethylGene, and Sigma Aldrich.

In some embodiments the HDAC inhibitor(s) can be Trichostatin A (TSA) and/or MS275.

The HDAC inhibitor can be employed in the compositions and methods described herein in a variety of amounts and/or concentrations. For example, the HDAC inhibitor can be employed at a concentration of about 0.001 micromolar to about 20 millimolar, or about 0.01 micromolar to about 5 millimolar in a solution. In a dry formulation, the HDAC inhibitor can be present in amounts of about 0.01 mg to about 100 mg, or about 0.05 mg to about 50 mg, or about 0.1 mg to about 25 mg, or about 1 mg to about 8 mg. For example, entinostat (MS275) has been administered during clinical trials at dosages of about 4-5 mg/m$^2$ (Pili et al., *Br J Cancer* 106(1): 77-84 (2012)), where mg/m$^2$ is mg per body surface area of patient. The adult average body surface is about 2.2 m$^2$ and formulae are available converting height and weight into body surface area.

p300 Activator

The p300 gene product is a histone acetyltransferase. As illustrated herein one or more activators of p300 histone acetyltransferase facilitate conversion of differentiated cells into a neuronal lineage. Examples of p300 activators include CTB, CTPB, TTK21, or any combination thereof (see, Devipriya et al., *Indian J Biochem Biophys* 47(6): 364-69 (2010); Chatterjee et al., *J. Neurosci* 33(26): 10698-712 (2013).

The CTPB [N-(4-chloro-3-trifluoromethyl-phenyl)-2-ethoxy-6-pentadecyl-benzamide] and CTB [N-(4-chloro-3-trifluoromethyl-phenyl)-2-ethoxybenzamide], compounds are available from Sigma-Aldrich. CTPB was a first known small molecular activator of histone acetyltransferase p300. CTB is a simplified analog of CTPB with comparable or higher activity. The compound activates the histone acetyltransferase (HAT) activity of p300/EP300/E1A binding protein. In some embodiments, the p300 activator can be CTB.

The p300 activator(s) can be employed in the compositions and methods described herein in a variety of amounts and/or concentrations. For example, the p300 activator(s) can be employed at a concentration of about 0.001 micromolar to about 20 millimolar, or about 0.01 micromolar to about 5 millimolar in a solution. In a dry formulation, the p300 activator(s) can be present in amounts of about 0.01 mg to about 100 mg, or about 0.05 mg to about 50 mg, or about 0.1 mg to about 25 mg, or about 1 mg to about 8 mg.

PDE4 Inhibitor(s)

As illustrated herein use of one or more phosphodiesterase type 4 (PDE4) inhibitors can facilitate conversion of differentiated cells into the neuronal cell lineage.

PDE4-inhibitors that can be used in the methods and compositions described herein can be compounds selected from among the following:

rolipram (also known as Rolipramum; 4-(3-cyclopentyloxy-4-methoxyphenyl)pyrrolidin-2-one), with, for example, an IC50 against PDE4 of about 0.001 to 0.01 µM;

enprofylline (also known as 3-Propylxanthine, 3-n-Propylxanthine, Nilyph, Oxeze, Enprofilina, Enprofyllinum; 3-propyl-7H-purine-2,6-dione), theophylline (also known as Elixophyllin, or Theolair, 1,3-Dimethylxanthine; 1,3-dimethyl-7H-purine-2,6-dione);

roflumilast (also known as Daliresp, or DAXAS, 162401-32-3; 3-(cyclopropylmethoxy)-N-(3,5-dichloropyridin-4-yl)-4-(difluoromethoxy)benzamide), with, for example, an IC50 of 0.6 nM against PDE4;

ariflo (also known as cilomilast, SB 207499, 153259-65-5; 4-cyano-4-(3-cyclopentyloxy-4-methoxyphenyl)cyclohexane-1-carboxylic acid), with, for example, an IC50 of about 0.15 µM;

tofimilast (also known as 185954-27-2, SureCN230762, CHEMBL217899, CHEBI:465916;), with, for example, an IC50 of about 0.013 µM against PDE4;

pumafentrin (also known as AC1MHJYR, SureCN26718, UNII-063D2YI19E, CHEMBL2106994; 4-[(4aR,10bS)-9-ethoxy-8-methoxy-2-methyl-3,4,4a,10b-tetrahydro-1H-benzo[c][1,6]naphthyridin-6-yl]-N,N-di(propan-2-yl)benzamide);

lirimilast (also known as UNII-GDK3KY5FCU, AC1O5FM0, CHEMBL1922282, NCGC00263118-01; [3-(carbamoylamino)-2-(2,4-dichlorobenzoyl)-1-benzofuran-6-yl]methanesulfonate);

arofyllin (also known as AC1L4YAX, AC1Q3SIW, Arofylline (USAN/INN); 3-(4-chlorophenyl)-1-propyl-7H-purine-2,6-dione);

atizoram (also known as SureCN118783, UNII-8SI21E44GN, CHEMBL1229569, MolPort-009-019-632, Cp-76593; 5-[3-[[(1R,3S,4S)-3-bicyclo[2.2.1] heptanyl]oxy]-4-methoxyphenyl]-1,3-diazinan-2-one);

D-4418 (N-(2,5-dichloropyridin-3-yl)-8-methoxyquinoline-5-carboxamide), with, for example, an IC50 of about 170 nM against PDE4;

Bay-198004 (2-(2,4-dichlorobenzoyl)-3-ureidobenzofuran-6-yl methanesulfonate);

Sch-351591 (also known as SureCN157018, CHEMBL2SOS46, CHEBI:513635, DNC004167; 5-dichloro-1-hydroxypyridin-4-ylidene)-8-methoxy-2-(trifluoromethyl)quinoline-5-carboxamide), with, for example, an IC50 of 0.15 µM against PDE4;

AWD-12-281 (also known as GW-842470, AC1OCFF4, SureCN155120, UNII-550671J2D, ZINC02003640, GSK 842470, GSK-842470, LS-8916; N-(3,5-dichloropyridin-4-yl)-2-[1-[(4-fluorophenyl)methyl]-5-hydroxyindol-3-yl]-2-oxoacetamide);

NCS-613 (9-(3-fluorobenzyl)-N-methyl-2-(trifluoromethyl)-9H-purin-6-amine);

CDP-840 (4-[(2R)-2-(3-cyclopentyloxy-4-methoxyphenyl)-2-phenylethyl]pyridine), with, for example, an IC50 of about 10 µM for PDE4;

Cl-1018 (N-[(3R)-9-methyl-4-oxo-1-phenyl-3,4,6,7-tetrahydro[1,4]diazepino[6,7,1-hi]indol-3-yl]pyridine-4-carboxamide), with, for example, an IC50 of about 3 µM for PDE4;

T-440 (also known as SureCN155132, ACIL432R, ZINC01544489, 89607-EP2270008A1, 89607-EP2281819A1, 89607-EP2292617A1, 89607-EP2292619A1, 89607-EP2298415A1; 4-[6,7-diethoxy-2,3-bis(hydroxymethyl)naphthalen-1-yl]-1-(2-methoxyethyl)pyridin-2-one);

Tyrphostin AG 537 (also known as NSC676486, bis-tyrphostin, Dimeric Tyrphostin 2, ACINS6EB, Lopac-T-2585; (E)-2-cyano-N-[3-[[(E)-2-cyano-3-(3,4-dihydroxyphenyl)prop-2-enoyl]amino]propyl]-3-(3,4-dihydroxyphenyl)prop-2-enamide);

V-11294A (3-[3-(cyclopentyloxy)-4-methoxybenzyl]-6-(ethylamino)-8-isopropyl-3H-purine);

CDC-801 (β-[3-(Cyclo-pentyloxy)-4-methoxyphenyl]-1,3-dihydro-1,3-dioxo-2H-isoindole-2-propanamide);

D-22888 (8-methoxy-5-N-propyl-3-methyl-1-ethyl-imidazo[1,5-a]-pyrido[3,2-e]-pyrazinone);

YM-58997 (4-(3-bromophenyl)-1-ethyl-7-methyl-1,8-naphthyridin-2(1H)-one, see e.g., U.S. Pat. No. 6,828,333), with, for example, an IC50 value of 1.2 nM against PDE4;

Z-15370;

N-(3,5-dichloro-1-oxo-pyridin-4-yl)-4-difluoromethoxy-3-cyclopropylmethoxybenzamide;

(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide;

(R)-(+)-1-(4-bromobenzyl)-4-[(3-cyclopentyloxy)-4-methoxyphenyl]-2-pyrrolidone;

3-(cyclopentyloxy-4-methoxyphenyl)-1-(4-N'-[N-2-cyano-S-methyl-isothioureido]benzyl)-2-pyrrolidone;

cis[4-cyano-4-(3-cyclopentyloxy-4-methoxyphenyl)cyclohexane-1-carboxylic acid];

2-carbomethoxy-4-cyano-4-(3-cyclopropylmethoxy-4-difluoromethoxy-phenyl)cyclohexan-1-one;

cis[4-cyano-4-(3-cyclopropylmethoxy-4-difluoromethoxyphenyl)cyclohexan-1-ol];

(R)-(+)-ethyl[4-(3-cyclopentyloxy-4-methoxyphenyl) pyrrolidin-2-ylidene]acetate;

(S)-(−)-ethyl[4-(3-cyclopentyloxy-4-methoxyphenyl)pyrrolidin-2-ylidene]acetate;

9-cyclopentyl-5,6-dihydro-7-ethyl-3-(2-thienyl)-9H-pyrazolo[3.4-c]-1,2,4-triazolo[4.3-a]pyridine;

9-cyclopentyl-5,6-dihydro-7-ethyl-3-(tert-butyl)-9H-pyrazolo[3.4-c]-1,2,4-triazolo[4.3-a]pyridine; or any combinations thereof.

The PDE4 inhibitor(s) can optionally be formulated or used in the form of the racemates, enantiomers or diastereomers thereof and optionally in the form of the pharmacologically acceptable acid addition salts thereof, the solvates and/or hydrates thereof. The acid addition salts of the PDE4 inhibitors can be selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate, and hydro-p-toluenesulphonate.

In some embodiments, the PDE4 inhibitor can be rolipram.

The PDE4 inhibitor(s) can be employed in the compositions and methods described herein in a variety of amounts and/or concentrations. For example, the PDE4 inhibitor(s) can be employed at a concentration of about 0.001 micromolar to about 20 millimolar, or about 0.01 micromolar to about 5 millimolar in a solution. In a dry formulation, the PDE4 inhibitor(s) can be present in amounts of about 0.01 mg to about 100 mg, or about 0.05 mg to about 50 mg, or about 0.1 mg to about 25 mg, or about 1 mg to about 8 mg.

Adenylyl Cyclase Agonist(s)

As illustrated herein use of one or more adenylyl cyclase agonists can facilitate conversion of differentiated cells into the neuronal cell lineage.

Adenylyl cyclase agonists stimulate the production of cyclic AMP (cAMP) in mammalian cells. One example of an adenylyl cyclase agonist is Forskolin (also known as Colforsin, Coleonol, Boforsin, colforsina, colforsine, colforsinum), which, for example, can have an IC50 of about 0.04-0.15 µM for adenylate cyclase 1.

The adenylyl cyclase agonist(s) can be employed in the compositions and methods described herein in a variety of amounts and/or concentrations. For example, the adenylyl cyclase agonist(s) can be employed at a concentration of about 0.001 micromolar to about 20 millimolar, or about 0.01 micromolar to about 5 millimolar in a solution. In a dry formulation, the adenylyl cyclase agonist(s) can be present in amounts of about 0.01 mg to about 100 mg, or about 0.05 mg to about 50 mg, or about 0.1 mg to about 25 mg, or about 1 mg to about 8 mg.

Retinoic Acid Receptor-Gamma (RARγ) Agonists

As illustrated herein use of one or more agonists of retinoic acid receptor-gamma can facilitate conversion of differentiated cells into the neuronal cell lineage. Agonists of RARγ stimulate the receptor to activate transcription of various genes.

A variety of RARγ agonists can be used in the compositions and methods described herein. For example, RARγ agonists can include:

CD1530 (4-(6-hydroxy-7-tricyclo[3.3.1.13,7]dec-1-yl-2-naphthalenyl)benzoic acid);

CD666 (also known as SureCN12572388, CHEMBL97080, 4-[(E)-3-hydroxy-3-(5,5,8,8-tetramethyl-6,7-dihydronaphthalen-2-yl)prop-1-enyl]benzoic Acid), NRX204647 (4-((1E,3E)-3-(hydroxyimino)-3-(5,5,8,8-tetramethyl-5,6,7,8-tetrahydronaphthalen-2-yl)prop-1-en-1-yl)benzoic acid);

retinoic acid;

all-trans retinoic acid (ATRA);

9-cis retinoic acid;

all-trans 3-4 didehydro retinoic acid 4-oxo retinoic acid;

Retinol;

4-[(E)-2-(5,6,7,8-tetrahydro-5,5,8,8-tetramethyl-2-naphthalenyl)-1-propenyl]benzoic acid;

4-(5-methoxymethyl-5-methyl-2,3,4,5-tetrahydro-1-benzo[b]oxepin-8-yl-ethynyl)-benzoic acid;

4-(5-ethoxymethyl-5-methyl-2,3,4,5-tetrahydrobenzo[b]oxepin-8-ylethynyl)-benzoic acid;

4-(5-methyl-5-propoxymethyl-2,3,4,5-tetrahydrobenzo[b]oxepin-8-ylethynyl)-benzoic acid;

(E)-4-[2-(5-methoxymethyl-5-propyl-2,3,4,5-tetrahydrobenzo[b]oxepin-8-yl)-vinyl]-benzoic acid;

(E)-4-[2-(5-methoxymethyl-5-methyl-2,3,4,5-tetrahydrobenzo[b]oxepin-8-yl)-vinyl]-benzoic acid;

(E)-4-[2-(5-methyl-5-propoxymethyl-2,3,4,5-tetrahydrobenzo[b]oxepin-8-yl)-vinyl]-benzoic acid;

4-(5-methoxymethyl-5-methyl-2,3,4,5-tetrahydrobenzo[b]thiepin-8-ylethynyl)-benzoic acid;

4-(5-ethoxymethyl-5-methyl-2,3,4,5-tetrahydrobenzo[b]thiepin-8-ylethynyl)-benzoic acid;

(E)-4-[2-(5-ethoxymethyl-5-methyl-2,3,4,5-tetrahydrobenzo[b]thiepin-8-yl)-vinyl]-benzoic acid;

(E)-4-[2-(5-methoxymethyl-5-propyl-2,3,4,5-tetrahydrobenzo[b]thiepin-8-yl)-vinyl]-benzoic acid;

4-(4-methoxymethyl-4-methyl-chroman-6-ylethynyl)-benzoic acid;

(E)-4-[2-(4-methoxymethyl-4-methyl-chroman-6-yl)-vinyl]-benzoic acid; or any combination thereof.

Additional RARγ agonists are described in WO 2001030326; WO 2001014360; and Shimono et al. (*Nat. Med.* 17: 454-460 (2011)), which are specifically incorporated herein by reference in their entireties.

Agonists of RARγ can be identified or evaluated by transactivation assays. The term "transactivation" refers to the ability of a retinoid to activate the transcription of a gene where the gene transcription is initiated by the binding of a ligand (e.g., agonist) to the RARγ. Determining the ability of a compound to transactivate a retinoic acid receptor can be performed by methods known to those of skill in the art. Examples of such methods are found in Bernard et al, *Biochem. Biophys. Res. Commun.,* 186: 977-983 (1992) and C. Apfel et al, *Proc. Nat. Sci. Acad.* (*USA*), 89: 7129-7133 (1992).

In some embodiments, the RARγ agonist is a RARγ selective agonist. A RARγ selective agonist refers to a compound that is able to selectively bind to the RARγ receptor and promote RARγ activation. RARγ selective agonists will bind to the RARγ receptor at significantly lower concentrations (>10 fold selectivity, preferable 50 to 100 fold selectivity) than the RARα, and RARβ receptors.

The RARγ agonist can, for example, be CD1530.

The RARγ agonist(s) can be employed in the compositions and methods described herein in a variety of amounts and/or concentrations. For example, the RARγ agonist(s) can be employed at a concentration of about 0.001 micromolar to about 50 millimolar, or about 0.01 micromolar to about 20 millimolar in a solution. In a dry formulation, the RARγ agonist(s) can be present in amounts of about 1 mg to about 4 g, or about 5 mg to about 3 g, or about 10 mg to about 2 g, or about 15 mg to about 1 g.

5-HT3 Antagonists

As illustrated herein use of one or more 5-HT3 antagonists can facilitate conversion of differentiated cells into the neuronal cell lineage. The 5-HT3 receptor is a subtype of serotonin receptor, but it belongs to the Cys-loop superfamily of ligand-gated ion channels (LGICs), and therefore differs from other 5-HT (serotonin) receptors. The 5-HT3 receptor is found in terminals of the vagus nerve and in certain areas of the brain.

A variety of 5-HT3 antagonists can be used in the compositions and methods described herein. For example, 5-HT3 antagonists can include:

TDMB (also known as NSC195183, NSC-195183, Tropanyl-3,5-dimethylbenzoate; sodium; [3-[[3-[(2-bromoacetyl)amino]phenoxy]-hydroxyphosphoryl]oxy-5-(5-methyl-2,4-dioxopyrimidin-1-yl)oxolan-2-yl]methyl-[3-[(2-bromoacetyl)amino]phenyl]hydrogen phosphate);

Ondansetron (also known as Zofran, Zophren, Zudan, Zofran ODT, 99614-02-5, Apo-ondansetron, Novo-ondansetron, PHL-ondansetron, PMS-ondansetron; 9-methyl-3-[(2-methylimidazol-1-yl)methyl]-2,3-dihydro-1H-carbazol-4-one), with, for example, a Ki of about 0.0162 μM for rat 5-HT3 receptors;

Granisetron (also known as 109889-09-0, ACINR4P1, BIDD:GT0272, CHEMBL519643, HMS2089P14, Sancuso, BRL-43694, C07023, D04370; 1-methyl-N-[(1S,5R)-9-methyl-9-azabicyclo[3.3.1]nonan-3-yl]indazole-3-carboxamide);

Tropisetron (also known as Navoban, (3-endo)-8-methyl-8-azabicyclo[3.2.1]oct-3-yl 1H-indole-3-carboxylate, Tropisetron (INN), AC1LCVDG, Lopac-T-104, beta-Tropisetron; [(1R,5S)-8-methyl-8-azabicyclo[3.2.1]octan-3-yl]1H-indole-3-carboxylate);

Dolasetron (also known as Dolasetronum [INN-Latin], Dolasteron, Dolasetronum, Anzemet, Dolasetron [INN:BAN], AC1L1TNT; UNII-82W12L7Q6E, AC1Q6P88, HSDB 7565);

Palonosetron (also known as Aloxi, Onicit, 2-Qhbiqo, Palonosetron [INN], AC1L3WNN, RS 25233-197, RS 25233-198, RS 25259-197, RS 25259-198; (3aR)-2-[(3S)-1-azabicyclo[2.2.2]octan-3-yl]-3a,4,5,6-tetrahydro-3H-benzo[de]isoquinolin-1-one);

Ramosetron (also known as Ramosetron (INN), Ramosetron [INN], (1-methylindol-3-yl)-[(5R)-4,5,6,7-tetrahydro-3H-benzimidazol-5-yl]methanone, 132036-88-5; (1-methylindol-3-yl)-[(5R)-4,5,6,7-tetrahydro-3H-benzimidazol-5-yl]methanone), with, for example, a Ki of 0.00006 μM for human 5HTA receptors; or any combination thereof.

In some embodiments, the 5-HT3 antagonist can be TDMB.

The 5-HT3 antagonist(s) can be employed in the compositions and methods described herein in a variety of amounts and/or concentrations. For example, the 5-HT3 antagonist(s) can be employed at a concentration of about 0.001 micromolar to about 50 millimolar, or about 0.01 micromolar to about 20 millimolar in a solution. In a dry formulation, the 5-HT3 antagonist(s) can be present in amounts of about 1 mg to about 4 g, or about 5 mg to about 3 g, or about 10 mg to about 2 g, or about 15 mg to about 1 g.

Metabotropic Glutamate (mGlu) Receptor Agonist

As illustrated herein use of one or more mGlu receptor agonists can facilitate conversion of differentiated cells into the neuronal cell lineage. Metabotropic glutamate receptors are a type of glutamate receptor. They are members of the group C family of G-protein-coupled receptors. Like other glutamate receptors, mGlu receptors bind glutamate, an amino acid that functions as an excitatory neurotransmitter.

A variety of metabotropic glutamate (mGlu) receptor agonists can be used in the compositions and methods described herein. For example, one or more of the following compounds can be used as mGlu receptor agonists in the compositions and methods of this application. Examples of metabotropic glutamate (mGlu) receptor agonists include the following:

ACPD (also known as trans-ACPD, 1S,3R-ACPD, (1S,3R)-1-aminocyclopentane-1,3-dicarboxylic acid, trans-(1S,3R)-ACPD, CB 1712, cis-ACPD, t-ACPD; (1S,3R)-1-aminocyclopentane-1,3-dicarboxylic acid), with, for example, an EC50 of about 9-40 μM for mGlu receptors;

ACPT-I (1S,3R,4S)-1-aminocyclo-pentane-1,3,4-tricarboxylic acid);

AMN082 (also known as AMN082, AMN082 DIHYDROCHLORIDE, 97075-46-2, A6605_SIGMA, SureCN3012657, CTK8F7746, AMN-082, MolPort-003-983-511, AG-H-31880; N,N'-dibenzhydrylethane-1,2-diamine);

DCPG (also known as Dcpg-An; [(2R,3S,4R,5R)-5-(2-amino-8-anilino-6-oxo-3H-purin-9-yl)-3,4-dihydroxyoxolan-2-yl]methyl[(2R,3S,5S)-5-(4-amino-2-oxopyrimidin-1-yl)-2-(hydroxymethyl)oxolan-3-yl] hydrogen phosphate);

GET73 (N-[(4-trifluoromethyl)benzyl]4-methoxybutyramide);

LSP1-2111 ((2S)-2-amino-4-[hydroxy[hydroxy(4-hydroxy-3-methoxy-5-nitro-phenyl)methyl]phosphoryl] butanoic acid), with, for example, an EC50 of 2.2 µM for human mGlu4 receptors;

Lu AF21934 ((1S,2R)-N1-(3,4-dichlorophenyl)cyclohexane-1,2-dicarboxamide), with, for example, an EC50 of 500 nM for human mGlu4 receptors;

Lu AF21935 ((1R,2S)-N1-(3,4-dichlorophenyl)cyclohexane-1,2-dicarboxamide), with, for example, an EC50 of more than 10 µM for human mGlu4 receptors;

Lu AF32615;

LY354740 (also known as Eglumegad, Eglumegad [INN], LY354740, 176199-48-7, AC1Q4UAB; 1S,2S,5R,6S-2-aminobicyclo[3.1.0]hexane-2,6-dicarboxylate), with, for example, an IC50 of about 0.254 µM against rat Group II mGlu receptor;

LY379268 (also known as CHEMBL8900, CHEBI: 243796, LY379268, (–)-2-oxa-4-aminobicyclo[3.1.0] hexane-4,6-dicarboxylate; (4R,6R)-4-amino-2-oxabicyclo[3.1.0]hexane-4,6-dicarboxylic acid), with, for example, a Ki ranging from 0.0027-100 µM for various mGlu receptors (where the Ki depends on Which receptor is bound by LY379268);

LY2140023 (also known as pomaglumetad methionil, UNII-3V85EZ3KFQ, SureCN1101575, Pomaglumetad methionil [USAN], LY-2140023, 1026791-63-8; (1R, 4S,5S,6S)-4-[[(2S)-2-amino-4-methylsulfanylbutanoyl]amino]-2,2-dioxo-2λ6-thiabicyclo[3.1.0] hexane-4,6-dicarboxylic acid), an mGlu2/3 agonist;

LY459477 (2-amino-4-fluorobicyclo[3.1.0]hexane-2,6-dicarboxylic acid), potency of 1-2 nM for rodent and human mGlu(2) and mGlu(3) receptors;

MMPIP (6-(4-methoxyphenyl)-5-methyl-3-(4-pyridinyl)-isoxazolo[4,5-c]pyridin-4(5H)-one; or 6-(4-methoxyphenyl)-5-methyl-3-pyridin-4-ylisoxazolo[4,5-c]pyridin-4(5H)-one;

ML182 (also known as VU0400195-3), with, for example, an EC50 of about 0.3-1.4 µM against mGlu4;

ML128 (also known as 1161205-04-4, cc-716, CHEMBL562551, CTK8E8748, CHEBI:657815, VU0361737, VU0361737-1; N-(4-chloro-3-methoxyphenyl)pyridine-2-carboxamide), with, for example, an EC50 of about 0.2-2.3 µM against mGlu4;

VU0155041 (cis-2-[[(3,5-dichlorophenyl)amino]carbonyl]cyclohexanecarboxylic acid); (1R,2S)-2-((3,4-dichlorophenyl)carbamoyl)cyclohexanecarboxylic acid, with an EC50 of 1000 nM for human mGlu4 receptors; or any combination thereof.

In some embodiments, the mGlu receptor agonist can be ACPD.

The metabotropic glutamate (mGlu) receptor agonist(s) can be employed in the compositions and methods described herein in a variety of amounts and/or concentrations. For example, the metabotropic glutamate (mGlu) receptor agonist(s) can be employed at a concentration of about 0.001 micromolar to about 50 millimolar, or about 0.01 micromolar to about 20 millimolar in a solution. In a dry formulation, the metabotropic glutamate (mGlu) receptor agonist(s) can be present in amounts of about 1 mg to about 4 g, or about 5 mg to about 3 g, or about 10 mg to about 2 g, or about 15 mg to about 1 g.

Rho-Associated Coiled-Coil Kinase (ROCK) Inhibitors

As illustrated herein use of one or more ROCK inhibitors can facilitate conversion of differentiated cells into the neuronal cell lineage. For example, experimental data described herein shows that ROCK inhibitors can facilitate neuronal conversion of Ascl1/Myt11 fibroblasts to the neuronal lineage.

Rho-associated coiled-coil kinase (ROCK) is an effector molecule of the Rho GTPase signaling pathway and controls physiological processes such as vascular constriction and nerve axon extension (Riento et al, *Nat Rev Mol Cell Biol* 4:446-456, 2003). A variety of ROCK inhibitors can be employed in the compositions and methods described herein including the following:

Y27632 (also known as—27632, Y27632, 146986-50-7, Y-27632 dihydrochloride, Y27, Y-27632, Y27632, Ximelegatran; 4-[(1R)-1-aminoethyl]-N-pyridin-4-yl-cyclohexane-1-carboxamide), a selective ROCK1 (p160ROCK) inhibitor with, for example, an IC50 of 140 nM;

4-(2-pyridylcarbamoyl)piperidine 1-benzyloxycarbonyl-4-(4-pyridylcarbamoyl)piperidine 1-benzoyl-4-(4-pyridylcarbamoyl)piperidine 1-propyl-4-(4-pyridylcarbamoyl)piperidine 1-[3-(2-(2-thienylmethyl)phenoxy)-2-hydroxypropyl]-4-(4-pyridylcarbamoyl)piperidine 4-(4-pyridylcarbamoyl)piperidine 1-benzyl-4-(4-pyridylcarbamoyl)-1,2,5,6-tetrahydropyridine 3-(4-pyridylcarbamoyl)piperidine 1-benzyl-3-(4-pyridylcarbamoyl)piperidine 1-(2-(4-benzyloxyphenoxy)ethyl)-4-(N-(2-pyridyl)-N-benzylcarbamoyl)piperidine 1-formyl-4-(4-pyridylcarbamoyl)piperidine 4-(3-pyridylcarbamoyl)piperidine 1-isopropyl-4-(4-pyridylcarbamoyl)piperidine 1-methyl-4-(4-pyridylcarbamoyl)piperidine 1-hexyl-4-(4-pyridylcarbamoyl)piperidine 1-benzyl-4-(4-pyridylcarbamoyl)piperidine 1-(2-phenylethyl)-4-(4-pyridylcarbamoyl)piperidine 1-(2-(4-methoxyphenyl)ethyl)-4-(4-pyridylcarbamoyl)-piperidine 1-(2-(4-methoxyphenyl)ethyl)-4-(2-pyridylcarbamoyl)-piperidine 1-(2-(4-chlorophenyl)ethyl)-4-(4-pyridylcarbamoyl)-piperidine 1-diphenylmethyl-4-(2-pyridylcarbamoyl)piperidine 1-[2-(4-(5-methyl-3-oxo-2,3,4,5-tetrahydropyridazin-6-yl)phenyl)ethyl]-4-(2-pyridylcarbamoyl)piperidine 1-(4-(4,5-dihydro-2-furyl)phenyl)-4-(4-pyridylcarbamoyl)piperidine 1-(2-nitrophenyl)-4-(4-pyridylcarbamoyl)piperidine 1-(2-aminophenyl)-4-(4-pyridylcarbamoyl)piperidine 1-nicotinoyl-4-(4-pyridylcarbamoyl)piperidine 1-isonicotinoyl-4-(4-pyridylcarbamoyl)piperidine 1-(3,4,5-trimethoxybenzoyl)-4-(4-pyridylcarbamoyl)-piperidine 1-acetyl-4-(4-pyridylcarbamoyl)piperidine 1-(3-(4-fluorobenzoyl)propyl)-4-(4-pyridylcarbamoyl)-piperidine 1-(3-(4-fluorobenzoyl)propyl)-4-(2-pyridylcarbamoyl)-piperidine 1-(1-(4-hydroxybenzoyl)ethyl)-4-(2-pyridylcarbamoyl)-piperidine 1-(1-(4-benzyloxybenzoyl)ethyl)-4-(2-pyridylcarbamoyl)-piperidine
1-(2-(4-hydroxyphenoxy)ethyl)-4-(2-pyridylcarbamoyl)piperidine
1-(4-(4-fluorophenyl)-4-hydroxybutyl)-4-(4-pyridylcarbamoyl)piperidine
1-(1-methyl-2-(4-hydroxyphenyl)-2-hydroxyethyl)-4-(2-pyridylcarbamoyl)piperidine
1-cinnamyl-4-(2-pyridylcarbamoyl)piperidine
1-(2-hydroxy-3-phenoxypropyl)-4-(4-pyridylcarbamoyl)piperidine
1-(2-hydroxy-3-phenoxypropyl)-4-(3-pyridylcarbamoyl)piperidine
1-(2-hydroxy-3-phenoxypropyl)-4-(2-pyridylcarbamoyl)piperidine
1-(2-phenylethyl)-4-[N-(2-pyridyl)-N-(2-(N,N-dimethylamino)ethyl)carbamoyl]piperidine
1-benzyloxycarbonyl-4-(2-pyridylcarbamoyl)Dpiperidine
1-(3-chlorophenyl)carbamoyl-4-(4-pyridylcarbamoyl)piperidine
4-[N-(2-pyridyl)-N-(2-(N,N-dimetliylamino)ethyl)-carbamoyl]piperidine
1-methyl-4-(4-pyridylcarbamoyl)-1,2,5,6-tetrahydropyridine
1-nicotinoyl-3-(4-pyridylcarbamoyl)piperidine
1-[2-(4-fluorobenzoyl)ethyl]-4-(4-pyridylcarbamoyl)-piperidine
1-(6-chloro-2-methylimidazol[1,2-a]pyridine-3-carbonyl)-4-(4-pyridylcarbamoyl)piperidine
1-(4-nitrobenzyl)-4-(4-pyridylcarbamoyl)piperidine
1-hexyl-4-(4-pyridylcarbamoyl)piperidine
1-benzyloxycarbonyl-4-(2-chloro-4-pyridylcarbamoyl)-piperidine
4-(2-chloro-4-pyridylcarbamoyl)piperidine
1-(2-chloronicotinoyl)-4-(4-pyridylcarbamoyl)piperidine
3-(2-chloro-4-pyridylcarbamoyl)piperidine
1-(4-phthalimidobutyl)-4-(4-pyridylcarbamoyl)piperidine
1-(3,5-di-tert-butyl-4-hydroxycinnamoyl)-4-(4-pyridylcarbamoyl)piperidine
1-carbamoylmethyl-4-(4-pyridylcarbamoyl)piperidine
1-benzyloxycarbonyl-4-(5-nitro-2-pyridylcarbamoyl)-piperidine
4-(5-nitro-2-pyridylcarbamoyl)piperidine
trans-4-benzyloxycarboxamidomethyl-1-(4-pyridylcarbamoyl)cyclohexane
trans-4-aminomethyl-1-(4-pyridylcarbamoyl)cyclohexane
trans-4-formamidomethyl-1-(4-pyridylcarbamoyty-cyclohexane
trans-4-dimethylaminomethyl-1-(4-pyridylcarbamoyl)-cyclohexane
N-benzylidene-trans-(4-pyridylcarbamoyl)-cyclohexylmethylamine
trans-4-benzylaminomethyl-1-(4-pyridylcarbamoyl)-cyclohexane
trans-4-isopropylaminomethyl-1-(4-pyridylcarbamoyl)-cyclohexane
trans-4-nicotinoylaminomethyl-1-(4-pyridylcarbamoyl)-cyclaexane
trans-4-cyclohexylaminomethyl-1-(4-pyridylcarbamoyl)-cyclohexane
trans-4-benzyloxycarboxamide-1-(4-pyridylcarbamoyl)-cyclohexane
trans-4-amino-1-(4-pyridylcarbamoyl)cyclohexane
trans-4-(1-aminoethyl)-1-(4-pyridylcarbamoyl)cyclohexane
trans-4-aminomethyl-cis-2-methyl-1-(4-pyridylcarbamoyl)-cyclohexane
(+)-trans-4-(1-benzyloxycarboxamidopropyl)-1-cyclohexanecarboxylic acid
(+)-trans-4-(1-benzyloxycarboxamidopropyl)-1-(4-pyridylcarbamoyl)cyclohexane
(−)-trans-4-(1-benzyloxycarboxamidopropyl)-1-(4-pyridylcarbamoyl)cyclohexane
(+)-trans-4-(1-aminopropyl)-1-(4-pyridylcarbamoyl)-cyclohexane
(−)-trans-4-(1-aminopropyl)-1-(4-pyridylcarbamoyl)-cyclohexane
(−)-trans-4-(1-benzyloxycarboxamidoethyl)-1-(4-pyridylcarbamoyl)cyclohexane
(+)-trans-4-(1-benzyloxycarboxamidoethyl)-1-(4-pyridylcarbamoyl)cyclohexane
(+)-trans-4-(1-aminoethy)-1-(4-pyridylcarbamoyl)-cyclohexane
(−)-trans-4-(1-aminoethyl)-1-(4-pyridylcarbamoyl)-cyclohexane
trans-4-(4-chlorobenzoyl)aminomethyl-1-(4-pyridylcarbamoyl)cyclohexane
trans-4-aminomethyl-1-(2-pyridylcarbamoyl)cyclohexane
trans-4-benzyl oxycarboxamidomethyl-1-(2-pyridylcarbamoyl)cyclohexane
trans-4-methylaminomethyl-1-(4-pyridylcarbamoyl)-cyclohexane
trans-4-(N-benzyl-N-methylamino)methyl-1-(4-pyridylcarbamoyl)cyclohexane
trans-4-aminomethyl-1-(3-pyridylcarbamoyl)cyclohexane
trans-4-aminomethyl-1-[(3-hydroxy-2-pyridyl)carbamoyl]-cyclohexane
trans-4-benzyloxycarboxamidomethyl-1-(3-pyridylcarbamoytycyclohexane
trans-4-benzyloxycarboxamidomethyl-1-[(3-benzyloxy-2-pyridyl)carbamoyl]cyclohexane
trans-4-phthalimidomethyl-1-(4-pyridylcarbamoyl)-cyclohexane
trans-4-benzyloxycarboxamidomethyl-1-(3-methyl-4-pyridylcarbamoyl)cyclohexane
trans-4-aminomethyl-1-(3-methyl-4-pyridylcarbamoyl)-cyclohexane
4-(trans-4-benzyloxycarboxamidomethylcyclohexyl-carbonyl)amino-2,6-dimetliylpyridine-N-oxide
4-(trans-4-aminomethylcyclohexylcarbonyl)amino-2,6-dimethylpyridine-N-oxide
trans-4-aminomethyl-1-(2-methyl-4-pyridylcarbamoyl)-cyclohexane
trans-4-(1-benzyloxycarboxamidoethyl)-1-(4-pyridylcarbamoyl)cyclohexane
trans-4-(1-amino-1-methylethyl)-1-(4-pyridylcarbamoyl)-cyclohexane
trans-4-(2-aminoethyl)-1-(4-pyridylcarbamoyl)cyclohexane
trans-4-(2-amino-1-methylethyl)-1-(4-pyridylcarbamoyl)-cyclohexane
trans-4-(1-aminopropyl)-1-(4-pyridylcarbamoyl)cyclohexane
trans-4-aminomethyl-trans-1-methyl-1-(4-pyridylcarbamoyl)cyclohexane
trans-4-benzylaminomethyl-cis-2-methyl-1-(4-pyridylcarbamoyl)cyclohexane trans-4-(1-benzyloxycarboxamide-1-methylethyl)-1-(4-pyridylcarbamoyl)cyclohexane
trans-4-benzyloxycarboxamidomethyl-1-(N-methyl-4-pyridylcarbamoyl)cyclohexane
trans-4-(1-acetamide-1-methylethyl)-1-(4-pyridylcarbamoyl)cyclohexane
trans-N-(6-amino-4-pyrimidyl)-4-aminomethylcyclohexanecarboxamide
trans-N-(1H-pyrrolo[2,3-b]pyridin-4-yl)-4-aminomethylcyclohexanecarboxamide
(+)-trans-N-(1H-pyrrolo[2,3-b]pyridin-4-yl)-4-(1-aminoethylcyclohexanecarboxamide
trans-N-(1H-pyrrolo[2,3-b]pyridin-4-yl)-4-(1-amino-1-methylethyl)cyclohexanecarboxamide
trans-N-(1H-pyrazolo[3,4-b]pyridin-4-yl)-4-aminomethylcyclohexanecarboxamide
(+)-trans-N-(1H-pyrazolo[3,4-b]pyridin-4-yl)-4-(1-aminoethyl)cyclohexanecarboxamide
trans-N-(1H-pyrazolo[3,4-b]pyridin-4-yl)-4-(1-amino-1-methylethyl)cyclohexanecarboxamide
(+)-trans-N-(2-amino-4-pyridyl)-4-(1-aminoethyl)-cyclohexanecarboxamide
trans-N-(1H-pyrazolo[3,4-d]pyrimidin-4-yl)-4-aminomethylcyclohexanecarboxamide
(+)-trans-N-(1H-pyrazolo[3,4-d]pyrimidin-4-yl)-4-(1-aminoethyl)cyclohexane carboxamide
trans-N-(1H-pyrazolo[3,4-d]pyrimidin-4-yl)-4-(1-amino-1-methylethyl)cyclohexane carboxamide
trans-N-(4-pyrimidinyl)-4-aminomethylcyclohexanecarboxamide
trans-N-(3-amino-4-pyridyl)-4-aminomethylcycloliexanecarboxamide
trans-N-(7H-imidazo[4,5-d]pyrimidin-6-yl)-4-aminomethylcyclohexanecarboxamide
trans-N-(3H-1,2,3-triazolo[4,5-d]-pyrimidin-7-yl)-4-aminomethylcyclohexane carboxamide
trans-N-(1-benzyl-1H-pyrazolo[3,4-b]pyridin-4-yl)-4-aminomethylcyclohexane carboxamide  trans-N-(1H-5-pyrazolyl)-4-aminomethylcyclohexanecarboxamide
trans-N-(1H-pyrazolo[3,4-b]pyridm-4-yl)-4-aminomethylcyclohexanecarboxamide
trans-N-(4-pyridazinyl)-4-aminomethylcyclohexanecarboxamide
trans-N-(7H-pyrrolo[2,3-d]pyrimidin-4-yl)-4-aminomethylcyclohexanecarboxamide
trans-N-(2-amino-4-pyridyl)-4-aminomethylcyclohexanecarboxamide
trans-N-(thieno[2,3-d]pyrimidin-4-yl)-4-aminomethylcyclohexanecarboxamide
trans-N-(5-methyl-1,2,4-triazolo[1,5-a]pyrimidin-7-yl)-4-aminomethylcyclohexane carboxamide
trans-N-(3-cyano-5-methylpyrazolo[1,5-a]pyrimidin-7-yl)-4-aminomethylcyclohexanecarboxamide
trans-N-(1H-pyrazolo[3,4-b]pyridin-4-yl)-4-(1-amino-1-methylethyl)cyclohexanecarboxamide
trans-N-(2-(1-pyrrolidinyl)-4-pyridyl)-4-aminomethylcyclohexanecarboxamide
trans-N-(2,6-diamino-4-pyrimidyl)-4-aminomethylcyclohexanecarboxamide
(+)-trans-N-(7-methyl-1,8-naphthyridin-4-yl)-4-(1-aminoethyl)cyclohexanecarboxamide
trans-N-(1-benzyloxymethylpyrrolo[2,3-b]pyridin-4-yl)-4-aminomethylcyclohexanecarboxamide
(+)-trans-N-(1-methylpyrrolo[2,3-b]pyridin-4-yl)-4-(1-aminoethyl)cyclohexanecarboxamide
trans-N-benzyl-N-(2-benzylamino-4-pyridyl)-4-(1-amino-1-methylethyl)-cyclohexanecarboxamide
trans-N-(2-azide-4-pyridyl)-4-aminomethylcyclohexanecarboxamide
trans-N-(2,3-dihydro-1H-pyrrolo[2,3-b]pyridin-4-yl)-4-aminomethylcyclohexanecarboxamide
trans-N-(2,3-dihydro-1H-pyrrolo[2,3-b]pyridin-4-yl)-4-(1-amino-1-methylethyl)cyclohexanecarboxamide
trans-N-(2-carboxy-4-pyridyl)-4-aminomethylcyclohexanecarboxamide
(R)-(+)-trans-N-(3-bromo-1H-pyrrolo[2,3-b]pyridin-4-yl)-4-(1-aminoethyl)cyclohexanecarboxamide
trans-N-(1H-pyrrolo[2,3-b]pyridin-4-yl)-4-guanidinomethylcyclohexanecarboxamide
trans-N-(1H-pyrazolo[3,4-b]pyridin-4-yl)-4-guanidinomethylcyclohexanecarboxamide
trans-N-(4-pyridyl)-4-guanidinomethylcyclohexanecarboxamide
trans-N-(1-methylpyrrolo[2,3-b]pyridin-4-yl)-4-(guanidmomethyl)cyclohexanecarboxamide
trans-N-(1H-pyrrolo[2,3-b]pyridin-4-yl)-4-(2-imidazolin-2-yl)aminomethylcycloliexanecarboxamide
trans-N-(1-benzoxymethylpyrrolo[2,3-b]pyridin-4-yl)-4-guanidinomethylcyclohexanecarboxamide
trans-N-(2-amino-4-pyridyl)-4-guanidinomethylcyclohexanecarboxamide
trans-N-(1-benzyloxymethyl-1H-pyrrolo[2,3-]pyridin-4-yl)-4-(2-imidazolin-2-yl)aminomethylcyclohexanecarboxamide
trans-N-(1H-pyrrolo[2,3-b]pyridin-4-yl)-4-(3-benzylguanidinomethyl)cyclohexanecarboxamide
trans-N-(1H-pyrrolo[2,3-b]pyridin-4-yl)-4-(3-phenylguanidinomethyl)cyclohexanecarboxamide
trans-N-(1H-pyrrolo[2,3-b]pyridin-4-yl)-4-(3-propylguanidinomethyl)cyclohexanecarboxamide
trans-N-(1H-pyrrolo[2,3-b]pyridin-4-yl)-4-(3-octylguanidinomethyl)cyclohexanecarboxamide
trans-N-(1-benzyloxymethylpyrrolo[2,3-b]pyridin-4-yl)-4-(2-benzyl-3-ethylguanidinomethyl)cyclohexanecarboxamide
trans-N-(1H-pyrrolo[2,3-b]pyridin-4-yl)-4-(imidazol-2-yl)aminomethylcyclohexanecarboxamide
trans-N-(1H-pyrrolo[2,3-b]pyridin-4-yl)-4-(thiazol-2-yl)aminomethylcyclohexanecarboxamide
(R)-(+)-N-(4-pyridyl)-4-(1-aminoethyl)benzamide
N-(4-pyridyl)-4-(1-amino-1-methylethyl)benzamide
N-(4-pyridyl)-4-aminomethyl-2-benzyloxybenzamide
N-(4-pyridyl)-4-aminomethyl-2-ethoxybenzamide
(R)-(−)-N-(4-pyridyl)-4-(1-aminooethyl)-3-nitrobenzamide
(R)-(−)-N-(4-pyridyl)-3-amino-4-(1-aminoethyl)benzamide
(R)-(+)-N-(4-pyridyl)-4-(1-aminoethyl)-3-chlorobenzamide
N-(4-pyridyl)-3-aminomethylbenzamide
(R)-(+)-N-(1H-pyrrolo[2,3-b]pyridin-4-yl)-4-(1-aminoethyl)benzamide
(R)-(+)-N-(1H-pyrazolo[3,4-b]pyridin-4-yl)-4-(1-aminoethyl)benzamide
N-(1H-pyrazolo[3,4-b]pyridin-4-yl)-4-guanidinomethylbenzamide
N-(4-pyridyl)-4-guanidinomethylbenzamide
(R)-(+)-N-(4-pyridyl)-4-(1-aminoethyl)-3-fluorobenzamide
N-(4-pyridyl)-4-aminomethylbenzamide
N-(4-pyridyl)-4-aminomethyl-2-hydroxybenzamide
N-(4-pyridyl)-4-(2-aminoethyl)benzamide N-(4-pyridyl)-4-aminomethyl-3-nitrobenzamide
N-(4-pyridyl)-3amino-4-aminomethylbenzamide
(S)-(−)-N-(4-pyridyl)-4-(1-aminoethyl)benzamide
(S)-(−)-N-(4-pyridyl)-2-(1-aminoethyl)benzamide
(R)-(+)-N-(4-pyridyl)-4-(1-aminoethyl)-2-chlorobenzamide
(R)-(+)-N-(1H-pyrrolo[2,3-b]pyridin-4-yl)-4-(1-(3-propylguanidino)ethyl)-benzamide
(R)-(−)-N-(1H-pyrrolo[2,3-b]pyridin-4-yl)-4-(1-aminoethyl-3-azidebenzamide
(R)-(+)-N-(4-pyridyl)-4-(1-aminoethyl)-2-nitrobenzamide
(R)-(−)-N-(4-pyridyl)-4-(1-aminoethyl)-3-ethoxybenzamide
(R)-(+)-N-(3-iodo-1H-pyrrolo[2,3-b]pyridm-4-yl)-4-(1-ammoethyl)benzamide
(R)-(+)-N-(3-iodo-1H-pyrrolo[2,3-b]pyridin-4-yl)-4-(1-aminoethyl)-3-azidebenzamide
(R)-(−)-N-(4-pyridyl)-4-(1-aminoethyl)-3-hydroxybenzamide
N-(1H-pyrazolo[3,4-b]pyridin-4-yl)-4-guanidinomethyl-3-nitrobenzamide
(R)-N-(1H-pyrazolo[3,4-b]pyridin-4-yl)-4-(1-guanidinoethyl)-3-nitrobenzamide
(R)-N-(1H-pyrazolo[3,4-b]pyridin-4-yl)-4-(1-aminoethyl)-2-nitrobenzamide
N-(1H--pyrazolo[3,4-b]pyridin-4-yl)-4-guanidinobenzamide
(R)-N-(1H-pyrazolo[3,4-b]pyridin-4-yl)-4-(1-aminoethyl)-3-nitrobenzamide
(R)-N-(1H-pyrazolo[3,4-b]pyridin-4-yl)-4-(1-guanidinoethyl)benzamide
N-(1H-pyrazolo[3,4-b]pyridin-4-yl)-4-(1-amino-2-hydroxyethyl)benzamide
N-(1H-pyrazolo[3,4-b]pyridin-4-yl)-4-aminomethyl-3-nitrobenzamide
N-(1H-pyrrolo[2,3-b]pyridin-4-yl)-4-piperidinecarboxamide
N-(1H-pyrazolo[3,4-b]pyridin-4-yl)-4-piperidinecarboxamide
N-(1H-pyrazolo[3,4-b]pyridin-4-yl)-1-aminoacetyl-4-piperidinecarboxamide
N-(1-methoxymethyl-1H-pyrazolo[3,4-b]pyridin-4-yl)-4-piperidinecarboxamide
N-(2,3-dihydro-1H-pyrrolo[2,3-b]pyridin-4-yl)-4-piperidinecarboxamide
N-(1H-pyrrolo[2,3-b]pyridin-4-yl)-1-(2-phenylethyl)-4-piperidinecarboxamide
N-(1H-pyrrolo[2,3-b]pyridin-4-yl)-1-amidino-4-piperidinecarboxamide
N-(1H-pyrrolo[2,3-b]pyridin-4-yl)-1-(3-phenylpropyl)-4-piperidinecarboxamide
N-(1H-pyrrolo[2,3-b]pyridin-4-yl)-1-benzyl-4-piperidmecarboxamide
N-(1H-pyrazolo[3,4-b]pyridin-4-yl)-1-(2-phenylethyl)-4-piperidinecarboxamide
N-(1H-pyrazolo[3,4-b]pyridin-4-yl)-1-(3-phenylpropyl)-4-piperidinecarboxamide;
N-(1H-pyrrolo[2,3-b]pyridin-4-yl)-4-(1-amino-1-methylethyl)benzamide; or
any combination thereof.

Inhibitors of ROCK are also described by International Patent Application No. PCT/AU2009/001417; International Patent Application No. PCT/GB2007/003636; Ishizaki et al, *Mol Pharmacol* 57:976-983 (2000); Narumiya et al, *Methods Enzymol* 525:273-284 (2000), each of which is specifically incorporated by reference herein in its entirety. Any of the ROCK inhibitors described in these documents can be employed in the compositions and methods described herein.

In some embodiments, the ROCK inhibitor can be Y27632.

The ROCK inhibitor(s) can be employed in the compositions and methods described herein in a variety of amounts and/or concentrations. For example, the ROCK inhibitor(s) can be employed at a concentration of about 0.001 micromolar to about 50 millimolar, or about 0.01 micromolar to about 20 millimolar in a solution. In a dry formulation, the ROCK inhibitor(s) can be present in amounts of about 0.1 mg to about 4 g, or about 0.5 mg to about 3 g, or about 1.0 mg to about 2 g, or about 1.5 mg to about 1 g.

Neuronal Differentiation Enhancers

As illustrated herein use of one or more neuronal differentiation enhancers can facilitate conversion of differentiated cells into the neuronal cell lineage. For example, experimental data described herein shows that neuronal differentiation enhancers can facilitate neuronal conversion of Ascl1/Myt11 fibroblasts to the neuronal lineage.

A variety of neuronal differentiation enhancers can be used in the compositions and methods described herein. For example, neuronal differentiation enhancers can include:

KHS2 (also known as SID 26759233, Neuropathiazol; ethyl 4-(methyl(2-phenyl-4,5-dihydrothiazol-4-yl) amino)benzoate);

basic fibroblast growth factor (bFGF), wherein human basic fibroblast growth factor is described, for example, by Abraham et al., *EMBO J.* 5:2523-2528 (1986), the contents of which are incorporated herein by reference in its entirety; and where sequence information for human basic fibroblast growth factor is available as Genbank Accession No. NP-001997.

fibroblast growth factor-8 (FGF-8; see, e.g., Gemel, J., *Genomics* 35:253-257, (1996); Yoshiura, K., *Am. J. Med. Genet.* 72: 354-362 (1997), the contents of each of which are incorporated herein by reference in its entirety); sequence information for human fibroblast growth factor 8 is available as Genbank Accession Nos. P55075, NP-149355, NP-006110, NP-149353, and NP-149354;

brain-derived neurotrophic factor (BDNF; see, e.g., Maisonpierre, P. C., *Genomics* 10: 558-568 (1991), the contents of which are incorporated herein by reference in its entirety); sequence information for human brain-derived neurotrophic factor is available as Genbank Accession No. P23560;

Sonic Hedgehog (SHH), see, e.g., Marigo, *Genomics* 28: 44-51 (1995), the contents of which are incorporated herein by reference in its entirety); sequence information for human sonic hedgehog is available as Genbank Accession No. Q15465;

N2 Supplement® (available from Gibco (Catalog No. 17502048, containing recombinant human insulin, human transferrin (iron-saturated), sodium selenite, putrescine and progesterone in Phosphate Buffered Saline); or any combination thereof.

In some embodiments, the neuronal differentiation factor is KHS2.

The amounts of neuronal differentiation factors in the compositions and methods provided herein can vary, for example, depending on the number of cells to be treated, the extent of conversion to the neuronal lineage (e.g., as assessed using neuronal cell markers), and the size and duration of the culture. Concentrations can range, for example, between 10-20 ng/mL, 20-30 ng/mL, 30-40 ng/mL, 40-50 ng/mL, 50-60 ng/mL, 60-70 ng/mL, 70-80 ng/mL, 80-90 ng/mL and 90-100 ng/mL. In a specific embodiment, 100 ng/mL bFGF, 10 ng/mL FGF-8, 100 ng/mL SHH and 10 ng/mL BDNF are used. Suitable concentrations can be determined by assaying the differentiation potential of cells having undergone the methods described herein.

Omega-3 Fatty Acids

As illustrated herein use of one or more omega-3 fatty acids can facilitate conversion of differentiated cells into the neuronal cell lineage. For example, experimental data described herein shows that omega-3 fatty acids can facilitate neuronal conversion of Ascl1/Myt1l fibroblasts to the neuronal lineage.

A variety of omega-3 fatty acids can be used in the compositions and methods described herein. For example, omega-3 fatty acids can include:
docosahexaenoic acid;
arachidonic acid;
linolenic acid;
linolenic acid;
eicosapentaenoic acid;
ethyl eicosapentaenoate (EPA-E); or
any combination thereof.

The omega-3 fatty acid(s) can be employed in the compositions and methods described herein in a variety of amounts and/or concentrations. For example, the omega-3 fatty acid(s) can be employed at a concentration of about 0.001 micromolar to about 50 millimolar, or about 0.01 micromolar to about 20 millimolar in a solution. In a dry formulation, the omega-3 fatty acid(s) can be present in amounts of about 0.1 mg to about 4 g, or about 0.5 mg to about 3 g, or about 1.0 mg to about 2 g, or about 1.5 mg to about 1 g.

A3 Adenosine Receptor Agonists

As illustrated herein use of one or more A3 adenosine receptor agonists can facilitate conversion of differentiated cells into the neuronal cell lineage. For example, experimental data described herein shows that A3 adenosine receptor agonists can facilitate neuronal conversion of Ascl1/Myt1l fibroblasts to the neuronal lineage.

Adenosine A3 receptors are G protein-coupled receptors that couple to Gi/Gq and are involved in a variety of intracellular signaling pathways and physiological functions.

A variety of A3 adenosine receptor agonists can be used in the compositions and methods described herein. For example, A3 adenosine receptor agonists can include:

IB-MECA (also known as 3-1B-Meca, N(6)-Ibamu, CF-101, CF 101, 152918-18-8, N(6)-(3-Iodobenzyl) adenosine-5'-N-methyluronamide; (2S,3S,4R,5R)-3,4-dihydroxy-5-[6-[(3-iodophenyl)methylamino]purin-9-yl]-N-ethyloxolane-2-carboxamide), with, for example, a IC50 for human A3 adenosine receptors of about 0.0012 µM;

AB-MECA (also known as N6-(4-Aminobenzyl)-N-methylcarboxamidoadenosine, 152918-26-8, [3H]AB-MECA, AC1NSJSB, A236_SIGMA, CHEMBL1256745; (2S,3S,4R,5R)-5-[6-[(4-aminophenyl)-methylamino]purin-9-yl]-3,4-dihydroxy-N-methyloxolane-2-carboxamide)

(R)-PIA (also known as L-PIA, 1-Phenylisopropyladenosine, (−)-N6-(2-Phenylisopropyl)adenosine, Phenylisopropyladenosine, L-, N6-D-Phenylisopropyladenosine), with, for example, a Ki for human A3 adenosine receptors of about 0.0012 µM;

(S)-PIA (also known as (2R,3S,4R,5R)-2-(hydroxymethyl)-5-[6-[[(2S)-1-phenylpropan-2-yl]amino]purin-9-yl]oxolane-3,4-diol, 38594-97-7; (2R,3S,4R,5R)-2-(hydroxymethyl)-5-[6-[[(2S)-1-phenylpropan-2-yl]amino]purin-9-yl]oxolane-3,4-diol), with, for example, a Ki for human A3 adenosine receptors of about 0.24 µM;

AB-NECA (N'-[6-anilino-9-[(2R,3R,4S,5R)-3,4-dihydroxy-5-(hydroxymethyl)oxolan-2-yl]purin-2-yl]-N-ethyloxamide);

CCPA (also known as 2-Chloro-N6-cyclopentyladenosine, CCPA, 37739-05-2, Adenosine, 2-chloro-N-cyclopentyl-, 2-CHLORO-N-CYCLOPENTYL-ADENOSINE, BRN 4888162; (2R,3R,4S,5R)-2-[2-chloro-6-(cyclopentylamino)purin-9-yl]-5-(hydroxymethyl)oxolane-3,4-diol)), with, for example, a Ki for human A3 adenosine receptors of about 0.038 µM;

[$^3$H]CCPA,

CGS 21680 (also known as Cgs 21680, CGS21680, CGS-21680; 3-[4-[2-[[6-amino-9-[(2R,3R,4S,5S)-5-(ethylcarbamoyl)-3,4-dihydroxyoxolan-2-yl]purin-2-yl]amino]ethyl]phenyl]propanoic acid), with, for example, an EC50 for human A3 adenosine receptors of about 0.6 µM;

[$^3$H]CGS 21680;

CGS 24012 (also known as 120442-40-2, ACMC-20mox1, AC1L1FBB, SureCN1973601, Adenosine, N-[2-(3,5-dimethoxyphenyl)-2-(2-methylphenyl)ethyl]-, CHEBI:130773, L000951; 2-[6-[[2-(3,5-dimethoxyphenyl)-2-(2-methylphenyl)ethyl]amino]purin-9-yl]-5-(hydroxymethyl)oxolane-3,4-diol);

2-chloroadenosine;

2-hexynyl-NECA (also known as Heneca, HE-NECA, 2-Hexynyl-NECA, 2-Hexynyl-5'-N-ethylcarboxamidoadenosine; (2S,3S,4R,5R)-5-(6-amino-2-hex-1-ynylpurin-9-yl)-N-ethyl-3,4-dihydroxyoxolane-2-carboxamide);

N$^6$-cyclopentyladenosine (also known as N6-Cyclopentyladenosine, Cyclopentyladenosine, SMR000058639, 41552-82-3, AC1LCWG1, SureCN120481, MLS000028368, MLS001077332, MLS002153196; (2R,3R,4S,5R)-2-[6-(cyclopentylamino)purin-9-yl]-5-(hydroxymethyl)-oxolane-3,4-diol), NECA (also known as 5'-N-Ethylcarboxamidoadenosine, N-ETHYL-5'-CARBOXAMIDO ADENOSINE, NEC; (2S,3S,4R,5R)-5-(6-aminopurin-9-yl)-N-ethyl-3,4-dihydroxyoxolane-2-carboxamide);

(R,S)-PHPNECA (also known as CHEBI:282064, (R,S)-2-phenylhydroxypropynyl-NECA, 2-(3-hydroxy-3-phenyl)propyn-1-yladenosine-5'-N-ethyluronamide; (2S,3R,4S)-5-[6-amino-2-(3-hydroxy-3-phenylprop-1-ynyl)purin-9-yl]1-N-ethyl-3,4-dihydroxyoxolane-2-carboxamide);

APNEA (also known as n-[2-(4-aminophenyl)ethyl]-9-pentofuranosyl-9h-purin-6-amine), 2-[6-[2-(4-aminophenyl)ethylamino]purin-9-yl]-5-(hydroxymethyl)oxolane-3,4-diol);

IAB-MECA (also known as (3S,4R)-5-(6-((4-aminobenzyl)amino)-9H-purin-9-yl)-3,4-dihydroxy-N-methyl-tetrahydrofuran-2-carboxamide));

Cyclopentyladenosine (also known as I-ABA, IAB-MECA, MCP-NECA, MPC-MECA, [$^3$H]NECA, PEN-ECA, AB-MECA, APNEA, CV-1674, CV-1808, cyclopentyladenosine, 2-hexynyl-NECA, metrifudil, N(6)-cyclohexyladenosine; (3R,4S,5R)-2-[6-(cyclopentylamino)purin-9-yl]-5-(hydroxymethyl)oxolane-3,4-diol);

LUF5831 (also known as 2-amino-6-(2-hydroxy-ethyl-sulfanyl)-4-(4-hydroxy-phenyl)-pyridine-3,5-dicarbonitrile);

Tecadenoson (also known as AC1L4KMO, Tecadenoson (USAN/INN), UNII-GZ1X96601Z, CVT-510, CHEMBL392149, CHEBI:502091, CID158795, DCL000313, LS-190860); or any combination thereof.

A variety of adenosine receptor agonists are described in Fredholm et al., *Pharmacological Rev* 53(4): 527-52 (2001) (which is incorporated herein by reference in its entirety). Any of the adenosine receptor agonists described above or by Fredholm can also be employed in the compositions and methods described herein.

In some embodiments, the adenosine receptor agonist is IB-MECA.

The adenosine receptor agonist(s) can be employed in the compositions and methods described herein in a variety of amounts and/or concentrations. For example, the adenosine receptor agonist(s) can be employed at a concentration of about 0.001 micromolar to about 50 millimolar, or about 0.01 micromolar to about 20 millimolar in a solution. In a dry formulation, the adenosine receptor agonist(s) can be present in amounts of about 0.1 mg to about 4 g, or about 0.5 mg to about 3 g, or about 1.0 mg to about 2 g, or about 1.5 mg to about 1 g.

L-Type Calcium Channel Blocker

As illustrated herein use of one or more L-type calcium channel blockers can facilitate conversion of differentiated cells into the neuronal cell lineage. For example, experimental data described herein shows that L-type calcium channel blocker can facilitate neuronal conversion of Ascl1/Myt11 fibroblasts to the neuronal lineage.

A variety of L-type calcium channel blockers can be used in the compositions and methods described herein. For example, L-type calcium channel blockers can include:

Nitrendipine (also known as Bayotensin, Baypress, Nidrel, Nitrendimerck, Nitregamma, Nitrendepat, Nitrendidoc, Nitrepress, Tensogradal; 5-O-ethyl 3-O-methyl-2,6-dimethyl-4-(3-nitrophenyl)-1,4-dihydropyridine-3,5-dicarboxylate);

Amlodipine (also known as Amlodis, Norvasc, Amlor, Istin, Astudal, Amlodipine maleate, AMLODIPINE BESYLATE, Amlodipine, (R)-Isomer, Amlodipine, (+-)-Isomer; 3-O-ethyl 5-O-methyl-2-(2-aminoethoxymethyl)-4-(2-chlorophenyl)-6-methyl-1,4-dihydropyridine-3,5-dicarboxylate);

Felodipine (also known as Plendil, Perfudal, Munobal, Flodil, Modip, Spiendil, Renedil, Prevex, Hydac; 5-O-ethyl 3-O-methyl-4-(2,3-dichlorophenyl)-2,6-dimethyl-1,4-dihydropyridine-3,5-dicarboxylate), with, for example, an IC50 of about 0.008 nM to about 0.023 μM;

Isradipine (also known as Lomir, DynaCirc, Isradipin, Dynacirc CR, Isrodipine, Esradin, Prescal, Clivoten, Dynacrine; 3-O-methyl 5-O-propan-2-yl-4-(2,1,3-benzoxadiazol-4-yl)-2,6-dimethyl-1,4-dihydropyridine-3,5-dicarboxylate);

Lacidipine (also known as Lacipil, Motens, 103890-78-4, GR 43659X, Lacidipinum [Latin], Lacidipino [Spanish], GR-43659X, GR 43659 X, Lacimen; diethyl-2,6-dimethyl-4-[2-[(E)-3-[(2-methylpropan-2-yl)oxy]-3-oxoprop-1-enyl]phenyl]-1,4-dihydropyridine-3,5-dicarboxylate), with, for example, an IC50 of about 0.0004 to about 0.005 μM;

Lercanidipine (also known as Lercanidipine [INN], masnidipine, 100427-26-7, Lercanil (TN), Lercanidipine (INN), AC1Q IZXR, UNH-V7XTJ4R0BH, STK639861, REC 15-2375; 5-O-[1-[3,3-diphenylpropyl(methyl)amino]-2-methylpropan-2-yl]3-O-methyl-2,6-dimethyl-4-(3-nitrophenyl)-1,4-dihydropyridine-3,5-dicarboxylate);

Nicardipine (also known as Nicardipinum [INN-Latin], Nicardipino [INN-Spanish], Nicardipine LA, Cardene IV, Cardene SR, Nicardipino, Nicardipinum; 5-O[2-[benzyl(methyl)amino]ethyl]3-O-methyl-2,6-dimethyl-4-(3-nitrophenyl)-1,4-dihydropyridine-3,5-dicarboxylate);

Nifedipine (also known as Corinfar, Procardia, Adalat, Procardia XL, Cordipin, Adalat CC, Fenihidin, Fenihidine, Citilat; dimethyl 2,6-dimethyl-4-(2-nitrophenyl)-1,4-dihydropyridine-3,5-dicarboxylate), with, for example, an IC50 of about 0.005 to about 1 μM;

Nimodipine (also known as Nimotop, Periplum, 66085-59-4, Nimodipinum [INN-Latin], Nimodipino [INN-Spanish], Nimodipinum, BAY e 9736, Nimodipino, Admon; 3-O-(2-methoxyethyl)5-O-propan-2-yl-2,6-dimethyl-4-(3-nitrophenyl)-1,4-dihydropyridine-3,5-dicarboxylate);

Nisoldipine (also known as Sular, Nisocor, Baymycard, Syscor, 63675-72-9, Nisoldipino, Nisoldipinum [INN-Latin], Nisoldipin, Zadipina; 3-O-methyl 5-O-(2-methylpropyl)-2,6-dimethyl-4-(2-nitrophenyl)-1,4-dihydropyridine-3,5-dicarboxylate), (+)isopropyl 2-methoxyethyl 4-(2-chloro-3-cyano-phenyl)-1,4-dihydro-2,6-dimethylpyridine-3,5-dicarboxylate; or any combination thereof.

In some embodiments, the L-type calcium channel blocker is Nitrendipine.

The L-type calcium channel blocker(s) can be employed in the compositions and methods described herein in a variety of amounts and/or concentrations. For example, the L-type calcium channel blocker(s) can be employed at a concentration of about 0.001 micromolar to about 50 millimolar, or about 0.01 micromolar to about 20 millimolar in a solution. In a dry formulation, the L-type calcium channel blocker(s) can be present in amounts of about 0.1 mg to about 4 g, or about 0.5 mg to about 3 g, or about 1.0 mg to about 2 g, or about 1.5 mg to about 1 g.

microRNA-124

As illustrated herein, expression of microRNA-124 (miR124) enhances the conversion of cells (e.g., starting cells) into neuronal cells.

A "miR124" or "microRNA-124" refers to a precursor of miR124 or complement thereof or a processed (i.e., mature) sequence of miR124, or a fragment of a precursor of miR124 comprising at least the processed sequence, or a complement thereof. In some embodiments, miR124 microRNA comprises a processed (mature) sequence of miR124 or a complement thereof.

Mature and precursor miR124 sequences are available, for example, in the data at www.mirbase.org. For example, a precursor sequence for human miR124 with accession number MI0000443 (ID: hsa-miR-124a-1) has the sequence shown below (SEQ ID NO:1).

```
 1   AGGCCUCUCU CUCCGUGUUC ACAGCGGACC UUGAUUUAAA
41   UGUCCAUACA AUUAAGGCAC GCGGUGAAUG CCAAGAAUGG
81   GGCUG
```

Another example of a precursor human miR124 with accession number MI0000444 (ID: hsa-miR-124a-2) has the sequence shown below (SEQ ID NO:2).

```
 1    AUCAAGAUUA GAGGCUCUGC UCUCCGUGUU CACAGCGGAC
41    CUUGAUUUAA UGUCAUACAA UUAAGGCACG CGGUGAAUGC
81    CAAGAGCGGA GCCUACGGCU GCACUUGAA
```

A mature human miR124 with accession number MIMT004591 (ID: hsa-miR-124-5p, or previous IDs: has-miR-124*), is present in the SEQ ID NO:1 sequence at nucleotides 25 to 46, and has the following sequence (SEQ ID NO:3).

```
 1         CGUGUUCACA GCGGACCUUG AU
```

A mature human miR124 (hsa-miR-124-3p) has nucleotides 62 to 81 of the SEQ ID NO:2 precursor human miR124 has accession number MIMAT0000422, and the following sequence (SEQ IU NO:4).

```
 1         UAAGGCACGC GGUGAAUGCC
```

A precursor sequence for mouse miR124 with accession number MI0000716 (ID: mmu-mir-124a-1) has the sequence shown below (SEQ ID NO:5).

```
 1    AGGCCUCUCU CUCCGUGUUC ACAGCGGACC UUGAUUUAAA
41    UGUCCAUACA AUUAAGGCAC GCGGUGAAUG CCAAGAAUGG
81    GGCUG
```

A mature mouse miR124 (mmu-miR-124-5p) with accession number MIMAT0004527 (previous ID: mmu-miR-124*), is present in the SEQ ID NO:5 sequence at nucleotides 25 to 46, and has the following sequence (SEQ ID NO:6).

```
 1         CGUGUUCACA GCGGACCUUG AU
```

A mature mouse miR124 (mmu-miR-I24-3p) with accession number MIMAT0000134 (previous IDs: mmu-miR-124a; mmu-miR-124), is present in the SEQ ID NO:5 sequence at nucleotides 62 to 81, and has the following sequence (SEQ ID NO:7).

```
 1         UAAGGCACGC GGUGAAUGCC
```

A rat precursor microRNA-124 (mo-miR-124) has accession number MI0000892 (previous ID: rno-mir-124a-3), and has the following sequence (SEQ ID NO:8).

```
 1    UGAGGGCCCC UCUGCGUGUU CACAGCGGAC CUUGAUUUAA
41    UGUCUAUACA AUUAAGGCAC GCGGUGAAUG CCAAGAGAGG
81    CGCCUCC
```

A mature rat miR124 (rno-miR-124-5p) with accession number MIMAT0004728 (previous ID: rno-miR-124*), is present in the SEQ ID NO:8 sequence at nucleotides 15 to 36, and has the following sequence (SEQ ID NO:9).

```
 1         CGUGUUCACA GCGGACCUUG AU
```

A mature rat miR124 (rno-miR-124-3p) with accession number MIMAT0000828 (previous IDs: rno-miR-124a; rno-miR-124), is present in the SEQ ID NO:8 sequence at nucleotides 53 to 72, and has the following sequence (SEQ ID NO:10).

```
 1         UAAGGCACGC GGUGAAUGCC
```

Nucleic acids encoding miR124 can be introduced into cells to facilitate conversion of cells into neuronal cells. Nucleic acid segments encoding miR124 can be inserted into or employed with any suitable expression system. The miR124 nucleic acids can be part of an expression cassette or expression vector that includes a promoter segment operably linked to the nucleic acid segment encoding the miR124. Recombinant expression is usefully accomplished using a vector. Vectors include but are not limited to plasmids, viral nucleic acids, viruses, phage nucleic acids, phages, cosmids, and artificial chromosomes. The vector can also include other elements required for transcription (and translation if a marker gene or other protein encoded segment is included in the vector). Such expression cassettes and/or expression vectors can express sufficient amounts of the miR124 microRNA to increase conversion of non-neuronal cells into neuronal cells.

Expression vectors and/or expression cassettes encoding microRNA can include promoters for driving the expression (transcription) of the microRNA. The vector can include a promoter operably linked to nucleic acid encoding a miR124 nucleic acid. Expression can include transcriptional activation, where transcription is increased above basal levels in the target cell by 10-fold or more, by 100-fold or more, such as by 1000-fold or more.

As used herein, vector refers to any carrier containing exogenous DNA. Thus, vectors are agents that transport the exogenous nucleic acid into a cell without degradation and include a promoter yielding expression of the miR124 in the cells into which it is delivered. A variety of prokaryotic and eukaryotic expression vectors suitable for carrying, encoding and/or expressing miR124 nucleic acids can be produced. Such expression vectors include, for example, pET, pET3d, pCR2.1, pBAD, pUC, and yeast vectors. The vectors can be used, for example, in a variety of in vivo and in vitro situations.

The expression cassette, expression vector, and sequences in the cassette or vector can be heterologous. The promoter and/or other regulatory segments can be heterologous to the segment encoding the miR124.

As used herein, the term "heterologous" when used in reference to a expression cassette, expression vector, regulatory sequence, promoter, or nucleic acid refers to a expression cassette, expression vector, regulatory sequence, or nucleic acid that has been manipulated in some way. For example, a heterologous promoter can be a promoter that is not naturally linked to a nucleic acid of interest, or that has been introduced into cells by cell transformation procedures. A heterologous nucleic acid or promoter also includes a nucleic acid or promoter that is native to an organism but that has been altered in some way (e.g., placed in a different chromosomal location, mutated, added in multiple copies, linked to a non-native promoter or enhancer sequence, etc.).

Heterologous nucleic acids may comprise sequences that comprise cDNA forms; the cDNA sequences may be expressed in either a sense (to produce mRNA) or anti-sense orientation (to produce an anti-sense RNA transcript that is complementary to the mRNA transcript). Heterologous coding regions can be distinguished from endogenous coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that at linked to a coding region to which they are not linked in nature.

Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors. Retroviral vectors that can be employed include those described in by Verma, I. M., Retroviral vectors for gene transfer. In MICROBIOLOGY-1985, AMERICAN SOCIETY FOR MICROBIOLOGY, pp. 229-232, Washington, (1985). For example, such retroviral vectors can include Murine Maloney Leukemia virus (MMLV), and other retroviruses that express desirable properties. Typically, viral vectors contain nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid.

A variety of regulatory elements can be included in the expression cassettes and/or expression vectors, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the miR124 nucleic acid segment. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bases in length, and they function in cis. Enhancers function to increase transcription from nearby promoters. Enhancers, like promoters, also often contain response elements that mediate the regulation of transcription. Enhancers often determine the regulation of expression.

Expression vectors used in eukaryotic host cells (e.g., animal, human or nucleated cells) can also contain sequences necessary for the termination of transcription which can affect miR124 and/or mRNA expression. For mRNA, these regions are transcribed as polyadenylated segments in the untranslated portion of the mRNA encoding tissue factor protein. The 3' untranslated regions also include transcription termination sites. The identification and use of 3' untranslated regions which include polyadenylation signals in expression constructs is well established.

The expression of miR124 from an expression cassette or expression vector can be controlled by any promoter capable of expression in prokaryotic cells or eukaryotic cells. Such promoters can include ubiquitously acting promoters, inducible promoters, or developmentally regulated promoters. Ubiquitously acting promoters include, for example, a CMV-β-actin promoter. Inducible promoters can include those that are active in particular cell populations or that respond to the presence of drugs such as tetracycline. Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. Vectors for bacterial expression include pGEX-5X-3, and for eukaryotic expression include pCIneo-CMV.

The expression cassette or vector can include a nucleic acid sequence encoding a marker product. This marker product is used to determine if the gene has been delivered to the cell and once delivered is being expressed. Preferred marker genes are fluorescent proteins, such as red fluorescent protein, green fluorescent protein, yellow fluorescent protein. The *E. coil* lacZ gene can also be employed as a marker. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern P. and Berg, P., *J. Molec. Appl. Genet.* 1:327 (1982)), mycophenolic acid, (Mulligan. R. C. and Berg, P. *Science* 209: 1422 (1980)) or hygromycin, (Sugden, B. et al., *Mol. Cell. Biol.* 5: 410-413 (1985)).

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. *Cancer Res.* 53:83-88, (1993)). Appropriate means for transfection, including viral vectors, chemical transfectants, or physico-mechanical methods such as electroporation and direct diffusion of DNA, are described by, for example, Wolff, J. A., et al., *Science*, 247, 1465-1468, (1990); and Wolff, J. A. *Nature*, 352, 815-818, (1991).

For example, the miR124 nucleic acid molecule, expression cassette and/or vector can be introduced to a cell by any method including, but not limited to, calcium-mediated transformation, electroporation, microinjection, lipofection, particle bombardment and the like. The cells can be expanded in culture and then administered to a subject, e.g. a mammal such as a human. The amount or number of cells administered can vary but amounts in the range of about $10^6$ to about $10^9$ cells can be used. The cells are generally delivered in a physiological solution such as saline or buffered saline. The cells can also be delivered in a vehicle such as a population of liposomes, exosomes or microvesicles.

The miR124 can be produced by a transgenic cell that produces exosomes or microvesicles that contain miR124. Exosomes and microvesicles mediate the secretion of a wide variety of proteins, lipids, mRNAs, and micro RNAs, interact with neighboring cells, and can thereby transmit signals, proteins, lipids, and nucleic acids from cell to cell (see, e.g., Shen et al., *J Biol Chem.* 286(16): 14383-14395 (2011); Hu et al., *Frontiers in Genetics* 3 (April 2012); Pegtel et al., *Proc. Nat'l Acad Sci* 107(14): 6328-6333 (2010); WO/2013/084000; each of which is incorporated herein by reference in its entirety.

The expression cassette(s) and/or expression vector(s) encoding the microRNA(s) can be introduced into starting cells or any cell subjected to the methods described herein. For example, the cells can be contacted with viral particles that include the expression cassettes. For example, retroviruses and/or lentiviruses are suitable for introduction of microRNAs. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid of interest are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) *Proc. Natl. Acad. Sci.* 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) *Mol. Cell. Biol.* 5:431-437); PA317 (Miller et al. (1986) *Mol. Cell. Biol.* 6:2895-2902); GRIP (Danos et al. (1988) *Proc. Natl. Acad. Sci.* 85:6460-6464). Retroviruses packaged with xenotropic envelope protein, e.g. AKR env, are capable of infecting most mammalian cell types, except murine cells. The appropriate packaging cell line may be used to ensure that the subject cells are targeted by the packaged viral particles. Suitable methods of introducing the retroviral vectors comprising expression cassettes into packaging cell lines and of collecting the viral particles that are generated by the packaging lines are well known in the art.

Starting Cells

A starting population of cells may be derived from essentially any source, and may be heterogeneous or homogeneous. The term "selected cell" or "selected cells" is also used to refer to starting cells. In certain embodiments, the cells to be treated as described herein are adult cells, including essentially any accessible adult cell type(s). In other embodiments, the cells used according to the invention are adult stem cells, progenitor cells, or somatic cells. In still other embodiments, the cells treated with any of the compositions and/or methods described herein include any type of cell from a newborn, including, but not limited to newborn cord blood, newborn stem cells, progenitor cells, and tissue-derived cells (e.g., somatic cells). In some embodiments, the starting population of cells does not include pluripotent stem cells. In other embodiments, the starting population of cells can include pluripotent stem cells. Accordingly, a starting population of cells that is reprogrammed by the compositions and/or methods described herein, can be essentially any live cell type, particularly a somatic cell type.

As illustrated herein, fibroblasts can be reprogrammed to cross lineage boundaries and to be directly converted to other cell types such as neuronal progenitor or mature functional neuronal cell types. Various cell types from all three germ layers have been shown to be suitable for somatic cell reprogramming by genetic manipulation, including, but not limited, to liver and stomach (Aoi et al., *Science* 321 (5889):699-702 (2008); pancreatic β cells (Stadtfeld et al., *Cell Stem Cell* 2: 230-40 (2008); mature B lymphocytes (Hanna et al., *Cell* 133: 250-264 (2008); human dermal fibroblasts (Takahashi et al., *Cell* 131, 861-72 (2007); Yu et al., Science 318(5854) (2007); Lowry et al., *Proc Natl Acad Sci USA* 105, 2883-2888 (2008); Aasen et al., *Nat Biotechnol* 26(11): 1276-84 (2008); meningiocytes (Qin et al., *J Biol Chem* 283(48):33730-5 (2008); neural stem cells (DiStefano et al., *Stem Cells Devel.* 18(5): (2009); and neural progenitor cells (Eminli et al., *Stem Cells* 26(10): 2467-74 (2008). Any such cells can be reprogrammed and/or programmed by use of the compositions and methods described herein.

In some embodiments the starting cells can transiently or continuously express miR124, Ascl1, Myt11, or a combination thereof during treatment or incubation with any of the compositions described herein. In other embodiments, the starting cells do not express detectable levels of miR124, Ascl1, Myt11, or any combination thereof.

The cells can be autologous or allogeneic cells (relative to a subject to be treated or who may receive the cells).

Reprogramming Methods

Starting cells are treated for a time and under conditions sufficient to convert the starting cells across lineage and/or differentiation boundaries to form neuronal progenitor cells or mature functional neuronal cells.

Cells can be incubated with a composition that contains one or more GSK3 inhibitors/WNT agonists, TGF-beta (ALK4/5/7) inhibitors, HDAC inhibitors, p300 activators, PDE4 inhibitors, adenylyl cyclase agonists, retinoic acid receptor γ agonists, 5-HT3 antagonists, metabotropic glutamate (mGlu) receptor agonists, and combinations thereof. The composition can contain at least two of the agents, or at least three of the agents, or at least four of the agents, or at least five of the agents, or at least six of the agents, or at least seven of the agents, or at least eight of the agents.

The time for conversion of starting cells into neuronal progenitor and mature neuronal cells can vary. For example, the starting cells can be incubated with the reprogramming composition until neuronal cell markers are expressed. Such neuronal cell markers can include Tuj1, Map2, NeuN, synapsins (e.g., Syn1 and Syn2), synaptophysin, synaptotagmins (e.g., Syt1, Syt4, Syt13, Syt16), NeuroD, Is11, and cholineacetyltransferase (ChAT, e.g., vascular ChAT (VChAT)).

Neuronal progenitor cells can, for example, be detected by observing expression of Tuj1, a neuron-specific class III beta-tubulin. Human β-Tubulin 3 is a 50,432 dalton structural protein (450 amino acid) expressed in neurons of the peripheral and central nervous systems. It contributes to microtubule stability in neuronal cell bodies and axons, and plays a role in axonal transport.

The starting cell(s) can also be incubated with the reprogramming composition until a more mature neuronal cell marker is expressed by the cells. For example, the starting cell(s) can be incubated with the reprogramming composition until expression of the Tau marker is observed. TAU is a neuronal microtubule-associated protein found predominantly on axons. The starting cell(s) can be incubated with the reprogramming composition until expression of the NeuN marker is observed. NeuN (neuronal nuclei) is expressed by mature (postmitotic) neurons throughout the nervous system. Similarly, the starting cell(s) can be incubated with the reprogramming composition until the more mature neuronal cell marker MAP2 is expressed by the cells. MAP2 is also a microtubule-associated protein with a role in neurogenesis.

The starting cell(s) can also be incubated with the reprogramming composition until the more mature neuronal cell marker Synapsin I is expressed by the cells. Synapsin I is a major phosphoprotein in synaptic terminals.

The time for conversion of starting cells into neuronal progenitor and mature neuronal cells can therefore vary. For example, the starting cells can be incubated with the composition under cell culture conditions for at least about 3 days, or for at least about 4 days, or for at least about 5 days, or for at least about 6 days, or for at least about 7 days, or for at least about 8 days, or for at least about 9 days, or for at least about 10 days, or for at least about 11 days, or for at least about 12 days, or for at least about 13 days, or for at least about 14 days, or for at least about 15 days, or for at least about 16 days, or for at least about 17 days, or for at least about 18 days, or for at least about 19 days.

In some embodiments, the starting cells can be incubated with the composition under cell culture conditions for about 5 days to about 35 days, or about 7 days to about 33 days, or about 10 days to about 30 days, or about 12 days to about 27 days, or about 15 days to about 25 days, or about 18 days to about 23 days.

As illustrated herein, a composition of nine chemical compounds (a GSK3 inhibitor/WNT agonist, an ALK4/5/7 inhibitor, an HDAC inhibitor, a p300 activator, a PDE4 inhibitor, an Adenylyl cyclase agonist, a retinoic acid receptor γ agonist, a 5-HT3 antagonist, and a metabotropic glutamate (mGlu) receptor agonist was sufficient to efficiently induce over 80% human fibroblasts to form Tuj1-positive cells after twenty days of incubation. Importantly, most of these Tuj cells exhibited typical neuronal morphology and many of them also expressed NeuN, a more mature neuronal marker.

The starting cells can be incubated with the reprogramming composition in a cell culture medium.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are available to those skilled in the art.

One example of a cell culture medium that can be employed is the N2B27 medium (containing 50% Neural basal medium and 50% DMEM/F12 medium supplemented with 1% GlutaMax, 1% N2 (Life Technologies), 2% B27 (Gihco), and 0.1% BSA). If more mature neuronal cells are desired the cells can be cultured within, or transferred after culture in the N2B27 medium to a maturation medium. One example of a maturation medium is the N2B27 medium that contains 0.5% Albumin, plus 20 ng ml$^{-1}$ GDNF (R&D Systems), 10 ng ml$^{-1}$ BDNF (R&D Systems), 10 ng ml−1 NT3 (R&D Systems), and 3 µM Forskolin (Tocris).

Examples of commercially available media include, but are not limited to, Dulbecco's Modified Eagle's Medium (DMEM), Minimal Essential Medium (MEM), Basal Medium Eagle (BME), RPMI 1640, Ham's F-10, Ham's F-12, a-Minimal Essential Medium (aMEM), Glasgow's Minimal Essential Medium (G-MEM), Iscove's Modified Dulbecco's Medium, or a general purpose media modified for use with pluripotent cells, such as X-VIVO (Lonza) or a hematopoeitic base media.

The starting cells can be dispersed in a cell culture medium that contains the reprogramming composition at a density that permits cell expansion. For example, about 1 to $10^{10}$ cells can be contacted with the reprogramming composition in a selected cell culture medium, especially when the cells are maintained at a cell density of about 1 to about $10^8$ cells per milliliter, or at a density of about 100 to about $10^7$ cells per milliliter, or at a density of about 1000 to about $10^6$ cells per milliliter.

Such methods can therefore be used to generate a population of neuronal cells that can be transplanted into a subject or used for experimentation.

In some embodiments, a reprogrammed population of cells can be frozen at liquid nitrogen temperatures, stored for periods of time, and then thawed for use at a later date. If frozen, a population of reprogrammed cells can be stored in a 10% DMSO, 50% FCS, 40% RPMI 1640 medium. Once thawed, the cells can be expanded by culturing the cells in an appropriate medium that can contain selected growth factors, vitamins, feeder cells, and other components selected by a person of skill in the art.

Treatment

The reprogrammed cells and compositions of compounds (with or without reprogrammed cells) that are described herein can also be employed in a method of treating a subject with a neuronal disease, condition, or injury.

Examples of diseases, conditions, and injuries that can be treated using the reprogrammed cells and compositions (containing any of the compounds described herein with or without reprogrammed cells include Amyotrophic lateral sclerosis (ALS), Alzheimer's disease, Parkinson's disease, multiple sclerosis, Primary lateral sclerosis (PLS), Progressive bulbar palsy, Pseudobulbar palsy, Progressive muscular atrophy, Spinal muscular atrophy (SMA), including Type I (also called Werdnig-Hoffmann disease), Type II, Type III (Kugelberg-Welander disease), Fazio-Londe disease, Huntington's disease, Kennedy's disease also known as progressive spinobulbar muscular atrophy, hereditary spastic paraplegia (HSP), congenital SMA with arthrogryposis, Post-polio syndrome (PPS), traumatic spinal cord injury, progressive pseudobulbar palsy, progressive muscular atrophy, postpolio syndrome, stroke, head trauma, spinal cord injury, and the like.

Diseases and conditions that can be treated include those that occur as a consequence of genetic defect, physical injury, environmental insult or conditioning, bad health, obesity and other disease risk factors commonly known by a person of ordinary skill in the art.

Efficacy of treatment can be monitored by clinically accepted criteria and tests, which include for example, using Electromyography (EMG), which is used to diagnose muscle and nerve dysfunction and spinal cord disease, and measure the speed at which impulses travel along a particular nerve. EMG records the electrical activity from the brain and/or spinal cord to a peripheral nerve root (found in the arms and legs) that controls muscles during contraction and at rest. One can also monitor efficacy of treatment using a nerve conduction velocity study to measure electrical energy to test the nerve's ability to send a signal, as well as laboratory screening tests of blood, urine, as well as magnetic resonance imaging (MRI), which uses computer-generated radio waves and a powerful magnetic field to produce detailed images of body structures including tissues, organs, bones, and nerves to detect and monitor degenerative disorders. In some embodiments, efficacy of treatment can also be assessed by a muscle or nerve biopsy, which can help confirm nerve disease and nerve regeneration. A small sample of the muscle or nerve is removed under local anesthetic and studied under a microscope. The sample may be removed either surgically, through a slit made in the skin, or by needle biopsy, in which a thin hollow needle is inserted through the skin and into the muscle. A small piece of muscle remains in the hollow needle when it is removed from the body. In some embodiments, efficacy of treatment can also be monitored by a transcranial magnetic stimulation to study areas of the brain related to motor activity.

Administration of Reprogrammed Cells

Reprogrammed cells generated as described herein can be employed for tissue reconstitution or regeneration in a human patient or other subjects in need of such treatment. The cells are administered in a manner that permits them to graft or migrate to a diseased or injured tissue site and to reconstitute or regenerate the functionally deficient area. Devices are available that can be adapted for administering cells, for example, into the spinal cord or other parts of the central or peripheral nervous system.

Reprogrammed cells can be administered to reconstitute the neuronal cell population in the spinal cord, brain, or at an alternative desired location. The cells may be administered to a recipient by local injection, or by systemic injection. In some embodiments, the cells can be administered parenterally by injection into a convenient cavity or by intramuscular injection.

Many cell types are capable of migrating to an appropriate site for regeneration and differentiation within a subject. To determine the suitability of cell compositions for therapeutic administration, the cells can first be tested in a suitable animal model. At one level, cells are assessed for their ability to survive and maintain their phenotype in vivo. Cells can also be assessed to ascertain whether they migrate to diseased or injured sites in vivo, or to determine an appropriate number of cells to be administered. Cell compositions can be administered to immunodeficient animals (such as nude mice, or animals rendered immunodeficient chemically or by irradiation). Tissues can be harvested after a period of regrowth, and assessed as to whether the administered cells or progeny thereof are still present, are alive, and/or have migrated to desired or undesired locations.

Injected cells can be traced by a variety of methods. For example, cells containing or expressing a detectable label (such as green fluorescent protein, or beta-galactosidase) can readily be detected. The cells can be pre-labeled, for example, with BrdU or [$^3$H] thymidine, or by introduction of an expression cassette that can express green fluorescent protein, or beta-galactosidase. Alternatively, the reprogrammed cells can be detected by their expression of a cell marker that is not expressed by the animal employed for testing (for example, a human-specific antigen). The presence and phenotype of the administered population of reprogrammed cells can be assessed by fluorescence microscopy (e.g., for green fluorescent protein, or beta-galactosidase), by immunohistochemistry (e.g., using an antibody against a human antigen), by ELISA (using an antibody against a human antigen), or by RT-PCR analysis using primers and hybridization conditions that cause amplification to be specific for human polynucleotides.

A number of animal models of motor neuron diseases are available for such testing, for example as the S0D1(G93A) mutant mouse and SMA (B6.129-Smn1$^{tm1Jme\ J}$) mouse models from Jackson laboratories.

A reprogrammed population of cells can be introduced by injection, catheter, implantable device, or the like. A population of reprogrammed cells can be administered in any physiologically acceptable excipient or carrier that does not adversely affect the cells.

A population reprogrammed cells can be supplied in the form of a pharmaceutical composition. Such a composition can include an isotonic excipient prepared under sufficiently sterile conditions for human administration. For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. The choice of the cellular excipient and any accompanying constituents of the composition that includes a population of reprogrammed cells can be adapted to optimize administration by the route and/or device employed.

A composition that includes a population of reprogrammed cells can also include or be accompanied by one or more other ingredients that facilitate engraftment or functional mobilization of the reprogrammed cells. Suitable ingredients include matrix proteins that support or promote adhesion of the reprogrammed cells, or complementary cell types, such as glial and/or muscle cells. In another embodiment, the composition may include physiologically acceptable matrix scaffolds. Such physiologically acceptable matrix scaffolds can be resorbable and/or biodegradable.

The population of reprogrammed cells generated by the methods described herein can include low percentages of non-neuronal cells (e.g., fibroblasts). For example, a population of reprogrammed cells for use in compositions and for administration to subjects can have less than about 90% non-neuronal cells, less than about 85% non-neuronal cells, less than about 80% non-neuronal cells, less than about 75% non-neuronal cells, less than about 70% non-neuronal cells, less than about 65% non-neuronal cells, less than about 60% non-neuronal cells, less than about 55% non-neuronal cells, less than about 50% non-neuronal cells, less than about 45% non-neuronal cells, less than about 40% non-neuronal cells, less than about 35% non-neuronal cells, less than about 30% non-neuronal cells, less than about 25% non-neuronal cells, less than about 20% non-neuronal cells, less than about 15% non-neuronal cells, less than about 12% non-neuronal cells, less than about 10% non-neuronal cells, less than about 8% non-neuronal cells, less than about 6% non-neuronal cells, less than about 5% non-neuronal cells, less than about 4% non-neuronal cells, less than about 3% non-neuronal cells, less than about 2% non-neuronal cells, or less than about 1% non-neuronal cells of the total cells in the cell population.

Pharmaceutical Compositions

The invention also relates to compositions containing one or more of the following chemical agents: a GSK3 inhibitor, a WNT agonist, a TGF-beta inhibitor, an ALK4/5/7 inhibitor, an HDAC inhibitor, a p300 activator, a PDE4 inhibitor, an Adenylyl cyclase agonist, a retinoic acid receptor γ agonist, a 5-HT3 antagonist, a metabotropic glutamate (mGlu) receptor agonist, a ROCK inhibitor, a neuronal differentiation enhancer, an omega-3 fatty acid, an A3 adenosine receptor agonist, and/or an L-type calcium channel blocker. For example, the composition can contain at least two of the agents, or at least three of the agents, or at least four of the agents, or at least five of the agents, or at least six of the agents, or at least seven of the agents, or at least eight of the agents, or at least nine of the agents, or at least ten of the agents, or at least eleven of the agents, or at least twelve of the agents, or at least thirteen of the agents. The compositions can also contain reprogrammed cells.

The compositions of the invention can be pharmaceutical compositions. In some embodiments, the compositions can include a pharmaceutically acceptable carrier. By "pharmaceutically acceptable" it is meant a carrier, diluent, excipient, and/or salt that is compatible with the other ingredients of the formulation, and not deleterious to the recipient thereof.

In some embodiments, the composition is a cell reprogramming composition.

The compositions can contain any of the agent(s) or compound(s) described herein in an amount sufficient to reprogram a cell into a neuronal cell type. For example, the compositions can contain any of the agent(s) or compound (s) described herein in an amount sufficient to induce a cell to express Tuj1, and/or in an amount sufficient to induce a cell to express Tau, and/or in an amount sufficient to induce a cell to express NeuN, and/or in an amount sufficient to induce a cell to express MAP2, and/or in an amount sufficient to induce a cell to express Synapsin. The cell contacted or treated by the compositions (whether in vitro or in vivo) can be any of the starting cells described herein. For example, the cell can be a non-neuronal cell and/or a differentiated cell.

In some embodiments, the therapeutic compositions are administered in a "therapeutically effective amount." Such a therapeutically effective amount is an amount sufficient to obtain the desired physiological effect, e.g., treatment of a condition, disorder, disease and the like or reduction in symptoms of the condition, disorder, disease and the like. For example, the therapeutic agents can be administered to treat a condition, disorder, or disease such Alzheimer's disease, Parkinson's disease, amyotrophic lateral sclerosis (ALS; Lou Gehrig's disease), multiple sclerosis, hereditary spastic paraplegia (HSP), primary lateral sclerosis, Huntington's disease, progressive pseudobulbar palsy, progressive muscular atrophy, progressive bulbar palsy, postpolio syndrome, stroke, head trauma, spinal cord injury, and the like.

To achieve the desired effect(s), the composition can be formulated in single or divided dosages. For example, a GSK3 inhibitor, a WNT agonist, a TGF-beta inhibitor, an ALK4/5/7 inhibitor, an HDAC inhibitor, a p300 activator, a PDE4 inhibitor, an Adenylyl cyclase agonist, a retinoic acid receptor γ agonist, a 5-HT3 antagonist, a metabotropic glutamate (mGlu) receptor agonist, a ROCK inhibitor, a neuronal differentiation enhancer, an omega-3 fatty acid, an A3 adenosine receptor agonist, and/or an L-type calcium channel blocker can present in the composition in amounts specified above or in dosages of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to the combination of compounds chosen for administration, the disease, the weight, the physical condition, the health, and the age of the mammal. Such factors can be readily determined by the clinician employing animal models or other test systems that are available in the art.

Reprogrammed cells can be included in the compositions in varying amounts depending upon the disease or injury to be treated. For example, the compositions can be prepared in liquid form for local or systemic administration containing about $10^3$ to about $10^{12}$ reprogrammed cells, or about $10^4$ to about $10^{10}$ reprogrammed cells, or about $10^5$ to about $10^8$ reprogrammed cells. One or more of the following types of compounds can also be present in the composition with the cells: a GSK3 inhibitor, a WNT agonist, a TGF-beta inhibitor, an ALK4/5/7 inhibitor, an HDAC inhibitor, a p300 activator, a PDE4 inhibitor, an Adenylyl cyclase agonist, a retinoic acid receptor γ agonist, a 5-HT3 antagonist, a metabotropic glutamate (mGlu) receptor agonist, a ROCK inhibitor, a neuronal differentiation enhancer, an omega-3 fatty acid, an A3 adenosine receptor agonist, and/or an L-type calcium channel blocker.

Administration of the composition, or contacting cell(s) with the composition may be in a single dose, in multiple doses, in a continuous or intermittent manner, depending, for example, upon the recipient's physiological condition, whether the purpose of the administration is in response to traumatic injury or for more sustained therapeutic purposes, and other factors known to skilled practitioners. The administration or contacting of the compounds and compositions of the invention may be essentially continuous over a preselected period of time or may be in a series of spaced doses. Both local and systemic administration is contemplated.

To prepare the composition, the compounds are synthesized and/or the cells are generated, and the components are purified as necessary or desired. The compounds, cells, and/or other agents can be suspended in a pharmaceutically acceptable carrier. If the composition contains only compounds, without cells, the composition can be lyophilized. These compounds and cells can be adjusted to an appropriate concentration, and optionally combined with other agents. The absolute weight of a given compound and/or other agent included in a unit dose can vary widely. For example, about 0.01 to about 2 g, or about 0.1 to about 500 mg, of at least one compound can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the compounds can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

It will be appreciated that the amount of compounds and cells for use in treatment will vary not only with the particular carrier selected but also with the route of administration, the nature of the condition being treated and the age and condition of the patient. Ultimately, the attendant health care provider may determine proper dosage. A pharmaceutical composition may be formulated with the appropriate ratio of each compound in a single unit dosage form for administration with or without cells. Cells can be separately provided and either mixed with a liquid solution of the compound composition, or administered separately.

The compounds can also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

One or more suitable unit dosage forms containing the compounds and/or the reprogrammed cells can be administered by a variety of routes including parenteral (including subcutaneous, intravenous, intramuscular and intraperitoneal), intracranial, intraspinal, oral, rectal, dermal, transdermal, intrathoracic, intrapulmonary and intranasal (respiratory) routes.

The compositions of the invention may be prepared in many forms that include aqueous solutions, suspensions, tablets, hard or soft gelatin capsules, and liposomes and other slow-release formulations, such as shaped polymeric gels. However, administration of cells often involves parenteral or local administration in an aqueous solution. Similarly, compositions containing cells and/or compounds can be administered in a device, scaffold, or as a sustained release formulation.

Thus while compositions containing only compounds can be administered in an oral dosage form, compositions containing cells are administered locally or systemically as non-oral formulations. When compositions contain only compounds, those compositions can be formulated as an oral dosage form so that the compounds are released into the stomach for quick absorption or in the intestine after passing through the stomach. Different types of formulating procedures are described in U.S. Pat. No. 6,306,434 and in the references contained therein.

Liquid pharmaceutical compositions may be in the form of, for example, aqueous or oily suspensions, solutions, emulsions, syrups or elixirs, dry powders for constitution with water or other suitable vehicles before use. Such liquid pharmaceutical compositions may contain conventional additives such as suspending agents, emulsifying agents, non-aqueous vehicles (which may include edible oils), or preservatives.

Compounds and/or cells can be formulated for parenteral administration (e.g., by injection, for example, bolus injection or continuous infusion) and may be presented in unit dosage form in ampoules, pretilled syringes, small volume infusion containers or multi-dose containers with an added preservative. The pharmaceutical compositions can take the form of suspensions, solutions, or emulsions in oily or aqueous vehicles, and can contain formulatory agents such as suspending, stabilizing and/or dispersing agents. Suitable carriers include saline solution, phosphate buffered saline, and other materials commonly used in the art.

The compositions can also contain other ingredients such as agents useful for treatment of neuronal diseases and injuries, such as, for example, riluzole, ceftriaxone, lithium, xaliproden, pioglitazone, pyridostigmine, seligiline, RNA interference (RNAi) nucleic acids for reducing ALS susceptibility, Alzheimer's symptoms, or for reducing expression of mutated genes (e.g., RNAi of mutant SOD1 genes, or RNAi for any of the mutant NFH, dynactin, vesicular binding protein or ALSIN genes), neurotrophic factors (e.g., IGF-1, EPO, CTNF, BDNF, VEGF), anti-oxidative agents such as HIF-loc, amino acids, creatine, and other agents or stem cells, e.g, embryonic stem cells used for the treatment of motor neuron diseases. Additional agents can also be included such as antibacterial agents, antimicrobial agents, anti-viral agents, biological response modifiers, growth factors; immune modulators, monoclonal antibodies and/or preservatives. The compositions of the invention may also be used in conjunction with other forms of therapy.

Supplementary factors can be included in the compositions and/or in a cell culture media containing any of the compositions, compounds or agents described herein. Examples of such supplementary factors include bone morphogenic protein (BMP)-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, brain derived neurotrophic factor, ciliary neutrophic factor, cytokine-induced neutrophil chemotactic factor 1, cytokine-induced neutrophil chemotactic factor $2\alpha$, cytokine-induced neutrophil chemotactic factor $2\beta$, $\beta$ endothelial cell growth factor, endothelin 1, epidermal growth factor, epithelial-derived neutrophil attractant, fibroblast growth factor (FGF) 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor (acidic), fibroblast growth factor (basic), growth related protein, growth related protein $\alpha$, growth related protein $\beta$, growth related protein $\gamma$, heparin binding epidermal growth factor, hepatocyte growth factor, insulin-like growth factor I, insulin-like growth factor II, insulin-like growth factor binding protein, keratinocyte growth factor, leukemia inhibitory factor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, pre-B cell growth stimulating factor, stem cell factor, transforming growth factor a, transforming growth factor $\beta$, transforming growth factor $\beta1$, transforming growth factor 01.2, transforming growth factor 132, transforming growth factor $\beta3$, latent transforming growth factor $\beta1$, transforming growth factor $\beta$ binding protein I, transforming growth factor $\beta$ binding protein II, transforming growth factor $\beta$ binding protein III, and vascular endothelial growth factor.

Exemplary cytokines can be included such as interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN), IFN-γ, tumor necrosis factor (TNF), TNF1, TNF2, TNF-α, macrophage colony stimulating factor (M-CSF), granulocyte-monocyte colony stimulating factor (GM-CSF), granulocyte colony stimulating factor (G-CSF), megakaryocyte colony stimulating factor (Meg-CSF)-thrombopoietin, stem cell factor, and erythropoietin. Chemokines can also be included such as IP-10 and Stromal Cell-Derived Factor 1α.

Exemplary hormones contemplated for inclusion in the compositions and/or cell culture media described herein can include, but are not united to, steroid hormones and peptide hormones, such as insulin, somatostatin, growth hormone, hydrocortisone, dexamethasone, 3,3',5-Triiodo-L-thyronine, and L-Thyroxine.

Kits

A variety of kits are described herein that include any of the compositions, compounds and/or agents described herein. The compounds and/or agents described herein can be packaged separately into discrete vials, bottles or other containers. Alternatively, any of the compounds and/or agents described herein can be packaged together as a single composition, or as two or more compositions that can be used together or separately. The compounds and/or agents described herein can be packaged in appropriate ratios and/or amounts to facilitate conversion of selected cells across differentiation boundaries to form neuronal cells.

A kit is described herein for culture of cells in vitro that can include any of the compositions, compounds and/or agents described herein, as well as instructions for using those compositions, compounds and/or agents. Some kits can include a cell culture medium or a variety of cell culture media that includes any of the compositions, compounds and/or agents described herein. The kits can include one or more sterile cell collection devices such as a swab, skin scrapping device, a needle, a syringe, and/or a scalpel. The kits can also include antibodies for detection of neuronal cell markers such as antibodies against Tuj1, Tau, NeuN, MAP2, Synapsin, or any combination thereof. The antibodies can be labeled so that a detectable signal can be observed when the antibodies form a complex with the neuronal cell marker(s).

The instructions can include guidance for culturing cells for a time and under conditions sufficient to convert a selected cell across differentiation boundaries and into the neuronal lineage. For example, the instructions can describe amounts of the compositions, compounds and/or agents described herein to add to cell culture media, times sufficient to convert cells to the neuronal lineage, maintenance of appropriate cell densities for optimal conversion, and the like. For example, the instructions can describe procedures for rehydration or dilution of the compositions, compounds and/or agents described herein. When a kit provides a cell culture medium containing some of the compositions, compounds and/or agents described herein, the instructions can describe how to add other compounds and/agents. The instructions can also describe how to convert the selected cells to neuronal progenitor cells or to mature neuronal cells.

The instructions can also describe procedures for detecting neuronal cell markers by use of the antibodies against those markers so that the extent of conversion and/or differentiation can be assessed.

Another kit is also described herein that includes any of the compositions, compounds and/or agents described herein for therapeutic treatment of a subject. The kit can include any of the compositions, compounds and/or agents described herein, as well as instructions for administering those compositions, compounds and/or agents. Such instructions can provide the information described throughout this application. The kit can also include cells. For example, the kit can include chemically induced neuronal cells that have been treated by the methods described herein and that are ready for administration.

The cells, compositions and/or compounds can be provided within any of the kits in a delivery device. Alternatively a delivery device can be separately included in the kit(s), and the instructions can describe how to assemble the delivery device prior to administration to a subject. The delivery device can provide a scaffold for cell growth and/or a matrix for controlled release of any of the compositions, compounds and/or agents described herein.

Any of the kits can also include syringes, catheters, scalpels, sterile containers for sample or cell collection, diluents, pharmaceutically acceptable carriers, and the like.

The kits can provide other factors such as any of the supplementary factors described herein for the compositions in the preceding section.

Definitions

As used herein, the term "neuronal cell" refers to a cell of a neuronal lineage. Examples of neuronal cells include, but are not limited to, neurons, astrocytes, oligodendrocytes, and neural precursor cells.

As used herein, the term "mature neuron" refers to a differentiated neuron. In some embodiments, a neuron is said to be a mature neuron if it expresses one or more markers of mature neurons, e.g., microtubule-associated protein 2 (MAP2) and Neuronal Nuclei (NeuN).

As used herein, the term "functional neuron" refers to a differentiated neuron that is able to send or receive electrical signals. In some embodiments, a neuron is said to be a functional neuron if it exhibits electrophysiological properties (e.g., if the neuron produces excitatory postsynaptic currents, which are indicative of functional synapses, and/or produces whole-cell currents and/or neurotransmitter receptor-mediated currents) and/or if it expresses one or more markers of functional neurons, e.g., Synapsin, vesicular GABA transporter (VGAT), vesicular glutamate transporter (VGLUT), and gamma-aminobutyric acid (GABA).

As used herein, a "differentiated non-neuronal cell" may refer to a cell that is not able to differentiate into all cell types of an adult organism (i.e., is not a pluripotent cell), and which is of a cellular lineage other than a neuronal lineage (e.g., a hematopoietic lineage or a connective tissue lineage). Differentiated cells include, but are not limited to, multipotent cells, oligopotent cells, unipotent cells, progenitor cells, and terminally differentiated cells. In particular embodiments, a less potent cell is considered "differentiated" in reference to a more potent cell.

As used herein, a cell that differentiates into a mesodermal, ectodermal or endodermal lineage defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoietic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to pleurigenic cells, and hepatogenic cells, that give rise to the lining of the intestine, and cells that give rise to pancreogenic and splanchogenic cells.

A "somatic cell" is a cell forming the body of an organism. Somatic cells include cells making up organs, skin, blood, bones and connective tissue in an organism, but not germ cells.

Cells can be from, e.g., human or non-human mammals. Exemplary non-human mammals include, but are not limited to, mice, rats, cats, dogs, rabbits, guinea pigs, hamsters, sheep, pigs, horses, bovines, and non-human primates. In some embodiments, a cell is from an adult human or non-human mammal. In some embodiments, a cell is from a neonatal human, an adult human, or non-human mammal.

As used herein, the term "totipotent" means the ability of a cell to form all cell lineages of an organism. For example, in mammals, only the zygote and the first cleavage stage blastomeres are totipotent.

As used herein, the term "pluripotent" means the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm.

As used herein, the term "multipotent" refers to the ability of an adult stem cell to form multiple cell types of one lineage. For example, hematopoietic stem cells are capable of forming all cells of the blood cell lineage, e.g., lymphoid and myeloid cells.

As used herein, the term "oligopotent" refers to the ability of an adult stem cell to differentiate into only a few different cell types. For example, lymphoid or myeloid stem cells are capable of forming cells of either the lymphoid or myeloid lineages, respectively.

As used herein, the term "unipotent" means the ability of a cell to form a single cell type. For example, spermatogonial stem cells are only capable of forming sperm cells.

As used herein, the term "direct reprogramming" or "transdifferentiation" refers to the generation of a cell of a certain lineage (e.g., a neuronal cell) from a different type of cell (e.g., a fibroblast cell) without an intermediate process of de-differentiating the cell into a cell exhibiting pluripotent stem cell characteristics.

A "microRNA" or "miRNA" refers to a non-coding nucleic acid (RNA) sequence that binds to complementary nucleic acid sequences (e.g., mRNAs) and negatively regulates the expression of the target nucleic acid (mRNA) at the post-transcriptional level. A microRNA is typically processed from a "precursor" miRNA having a double-stranded, hairpin loop structure to a "mature" form. Typically, a mature microRNA sequence is about 19-25 nucleotides in length.

As used herein, the terms "subject" or "patient" refers to any animal, such as a domesticated animal, a zoo animal, or a human. The "subject" or "patient" can be a mammal like a dog, cat, bird, livestock, or a human. Specific examples of "subjects" and "patients" include, but are not limited to, individuals with a neuronal disease or disorder, and individuals with neuronal disorder-related characteristics or symptoms.

As used herein, the term "neuronal disorder" or a "neuron disorder" refers to disorders of the nerves of the brain, spinal cord, or peripheral nervous system, including, but not limited to neurodegenerative/neurological disorders such as progressive deterioration of the nerves in the spinal cord and/or brain. Examples of neuron disorders include, but are not limited to, Alzheimer's disease, Parkinson's disease, amyotrophic lateral sclerosis (ALS; Lou Gehrig's disease), multiple sclerosis, hereditary spastic paraplegia (HSP), primary lateral sclerosis, Huntington's disease, progressive pseudobulbar palsy, progressive muscular atrophy, progressive bulbar palsy, postpolio syndrome, stroke, head trauma, spinal cord injury, and the like.

As used herein, the phrase "symptoms of neuron disorder" and "characteristics of neuron disorder" include, but are not limited to, lower extremity weakness, bladder disturbance, impaired position sense in the legs, and neurologic deficits, such as a decrease in the function of the brain, spinal cord, muscles, and/or nerves, for example, inability to speak, decreased sensation, loss of balance, weakness, cognitive dysfunction, visual changes, abnormal reflexes, and problems walking.

The following non-limiting Examples illustrate some of the experimental work involved in developing the invention.

EXAMPLE 1

Materials and Methods

This Example describes some of the materials and methods used in the development of the invention.

Lentiviral Constructs and Viral packaging

Doxycycline inducible plasmids pAscl1-TetO-FUW, pBrn2-TetO-FUW, and pMyt11-TetO-FUW were a kind gift from Marius Wernig (Stanford University). FUW-rtTA was purchased from Addgene. The pLemir-miR124 vector carrying miR124/IRES-RFP was purchased from Open Biosystems. miR124 is the most abundant microRNA in the mammalian central nervous system, it is significantly upregulated in differentiating and mature neurons, and it modulates the activity of major anti-neuronal differentiation factors. RFP is red fluorescent protein, used as a marker for miR124 expression. Plasmids for viral packaging were extracted by using ENDOFREE® Plasmid Maxi Kit (QIAGEN). Viral packaging was performed in 293T cells as previously described by Lin et al. (*Nat Methods* 6: 805-808 (2009).

Cell Culture, Infection, and Compound Treatment

Mouse Tau-EGFP MEFs or CF1 mouse embryonic fibroblasts (MEFs) were prepared and expanded as previously described by Vierbuchen et al. (*Nature* 463, 1035-1041 (2010)). Human foreskin fibroblasts (hF2097/CRL-2097 cells from the ATCC, or hFF cells from the Wernig lab/ Stanford University) were cultured in DMEM containing 10% FBS, non-essential amino acids, glutamax, sodium pyruvate, beta-mercaptoethanol and 5 mM HEPES (all from Invitrogen). For all the experiments, cells of early passage number (P2-P4 for mouse induction or P4-P8 for human induction) were used. In particular, $1 \times 10^6$ fibroblasts were seeded on 100 mm dishes. When cell confluence reached about 80%, the lentiviral particles were added for overnight infection. The infected fibroblasts were dissociated by trypsin and plated into different types of plates coated with Matrigel, including 6-well plates with $2 \times 10^5$ cells per well, 24-well plates with $5 \times 10^4$ cells per well, 384-well plates with $4 \times 10^3$ cells per well. The infected cells were cultured overnight in N2B27 medium (containing 50% Neural basal medium and 50% DMEM/F12 medium supplemented with 1% GlutaMax, 1% $N_2$, 2% B27, and 0.1% BSA) before changing to compound induction medium containing N2B27 medium plus Doxycycline (2.0 µg ml$^{-1}$, Sigma), and one or the other of the following chemical cocktails:

STRC2: 5 µM SB431542, 50 nM TSA, 5 µM Rolipram, 3 µM CHIR99021 and 5 µM CTPB; or 9C: 5 µM SB431542, 1 µM MS275, 5 µM Rolipram, 3 µM CHIR99021, 5 µM CTB, 3 µM Forskolin, 1 µM TDMB, 2 µM CD1530 and 5 µM ACPD After 7 days of compound treatment, cells were cultured in neuronal maturation medium (N2B27 medium, 0.5% Albumin, plus 20 ng ml$^{-1}$ GDNF (R&D Systems), 10 ng ml$^{-1}$ BDNF (R&D Systems), 10 ng ml$^{-1}$ NT3 (R&D Systems), and 3 µM Forskolin (Tocris)) until they were fixed for immunostaining. For the generation of compound induced neurons (CiN), hF2097 cells were treated with 9C induction medium plus the above cytokines for about 20 to about 30 days.

High-Throughput Compound Screening

Infected Tau-EGFP MEFs in 150-mm dishes were dissociated by trypsinization and plated to 384-well plates with $4 \times 10^3$ cells per well in 50 µl of N2B27 medium plus 2.0 µg ml$^{-1}$ doxycycline by using Multi-drop (Thermo Fisher). Fifty nanoliters of compounds from a collection of known drugs (~3,000) were added to each well of infected cells by using BioMek (BD). After 3 days of compound treatment, 20 µl N2B27 media were added to each well to keep the medium volume at 55-60 µl. The total period of compound treatment is 7 days. After that, medium was replaced with neuronal maturation medium for another 7 days. The cells were then fixed for immunostaining on Day 14. The high-throughput imaging was performed by using InCell 2000. Finally, the screening result was analyzed by InCell Workstation 2000.

Immunostaining

Primary antibodies used included: mouse anti-Tuj1 (Covance, 1:1000), Rabbit anti-MAP2 (Millipore, 1:500), mouse anti-NeuN (Millipore, 1:100), rabbit anti-Synapsin1 (Millipore, 1:1000), mouse anti-GAD65 (Millipore, 1:500), rabbit anti-vGLUT1 (Synaptic Systems, 1:1000), and rabbit anti-GlutR2&3 (Millipore, 1:500). Alexa-488- and Alexa-555-conjugated secondary antibodies were purchased from Invitrogen. Immunostaining was performed as previously described by Lin et al. (*Nat Methods* 6: 805-808 (2009). Cells were counterstained with DAPI to identify nuclei.

Time-Lapse Experiment

Human foreskin fibroblasts (hFFs) with the miR124-RFP/Brn2 construct were seeded onto Geltrex-coated 24-well plate at the cell density of $5 \times 10^4$ per well in the N2B27 medium. After 6 hours, when miR124-RFP/Brn2 containing hFFs attached to the plate, the medium was changed into compound induction medium (N2B27+STRC2+doxycycline). The imaging was performed on InCell 2000. The images of STRC2-miR124-RFP/Brn2 cells were taken every 10 minutes. Then the series of pictures taken from 65 to 100 hour were converted to a movie file (AVI) by using the software, Ulead GIF Animator 5.

Primary Neuronal Culture

Hippocampi from embryonic day 19 (E19) rats or postnatal day 0 (P0) mice were digested in Hanks' Balanced Salt Solution (HBSS) containing trypsin/EDTA (Gibco) for 25 min at 37° C., washed in trypsin free HBSS and triturated in DMEM containing 10% FBS. The cells were then plated in DMEM/FBS at the density of 120,000 cells per 12 mm poly-D-lysine-coated coverslip. After two hours, the neurons were washed twice and flooded with serum-free Neurobasal medium containing 2% B27 and 1% GlutaMAX.

Electrophysiology

Twenty-four hours after viral transduction, infected cells were trypsinized and plated on poly-D-lysine and laminin coated glass coverslips (12 mm) or Geltrex coated plastic coverslips (12 mm) without primary neuronal culture media and then cultured in neuronal maturation medium for the times indicated in the figure legends. The external bath solution for whole cell patch clamp recordings contained (in mM) 140 NaCl, 5 KCl, 2 $CaCl_2$, 2 $MgCl_2$, 20 HEPES, and 10 glucose, pH 7.4. Action potentials were recorded by current-clamp while sodium and potassium currents were recorded under voltage clamp. The internal pipette solution contained (in mM): 123 K-gluconate, 10 KCl, 1 MgCl2, 10 HEPES, 1 EGTA, 0.1 $CaCl_2$, 1 MgATP, 0.3 $Na_4GTP$ and 4 glucose, pH 7.2. For current clamp experiments, currents were injected to keep membrane potentials around −65 mV, and action potentials were elicited by stepwise current injections.

For synaptic functional evaluation, the internal solution contained (in mM): $CsMeSO_3$ 132, CsCl 5, NaCl 4, $MgCl_2$2, HEPES 10, EGTA 5, Mg-ATP 5, $Na_4GTP$ 0.3, and QX-314 5. Spontaneous EPSCs were recorded at −64 mV (GABA reversal potential ~−63 mV) and IPSCs at 0 mV. The identities of these responses were further confirmed by use of the AMPA receptor antagonist NBQX (10 µM, Tocris) and the $GABA_A$ receptor antagonist picrotoxin (50 µM, Sigma). Tetrodotoxin (TTX) was purchased from Abcam.

Statistical Analysis

Each experiment presented in the figures is representative of at least two independent experiments. Data were presented as mean±SEM and Student's t-test was applied for comparison. Statistical significance (p value) is indicated by the use of star symbols (*), e.g. p<0.05(*), p<0.01(), and p<0.001(*). All graphical data presented was prepared using GraphPad Software.

EXAMPLE 2

Reprogramming of Fibroblasts into Neuronal Cells

This Example demonstrates that fibroblasts can be redirected to become neuronal cells without genetic manipulation.

In a previous study, the combination of three transcription factors (i.e., Ascl1, Brn2 and Myt1l-BAM) was shown to effectively convert mouse embryonic fibroblasts (MEFs) into mature neurons (Vierbuchen et al., *Nature* 463, 1035-1041 (2010).

Figure 1B:
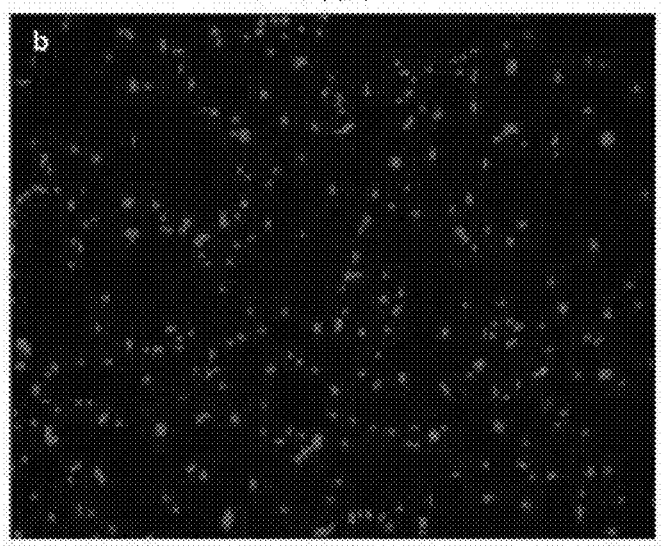
Figure 1C:
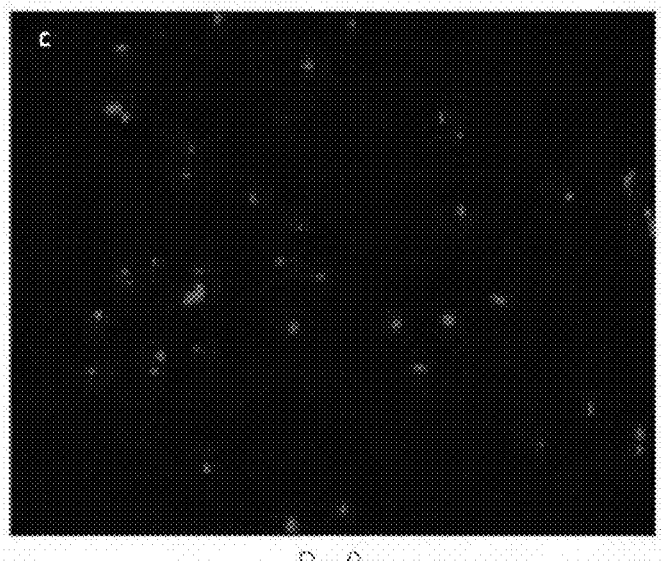

To identify small molecules that may ultimately induce neuronal reprogramming of fibroblasts with a single transcription factor, or even without any exogenous genetic factors, a step-wise screening strategy was devised, where a neuronal reprogramming baseline (i.e., a context with minimally sufficient exogenous genetic factors) was first used to screen reprogramming enabling and enhancing small molecules, followed by testing combinations of those identified compounds to further reduce genetic factors. To establish the screening baseline for neuronal reprogramming of MEFs, the neuronal induction was examined using Tau-EGFP knock-in reporter MEF cells (Tau expression serves as a mature neuronal marker) with additional βIII-tubulin immunostaining (as an earlier neuronal marker) under one-factor (Ascl1, Brn2, or Myt1l) and two-factor (Ascl1/Myt1l, Ascl1/Brn2, or Brn2/Myt1l) conditions in a fixed reprogramming time of 14 days. Consistent with the previous study, among one-factor conditions, only Ascl1 could induce a few cells expressing βIII-tubulin 14 days after induction (FIG. 1). However, those βIII-tubulin-expressing cells exhibited non-neuronal morphologies (e.g., still fibroblast-like, FIG. 2) and did not have other neuronal markers and properties, confirming that Ascl1 alone is not sufficient to induce the neuronal conversion. Among the 2-factor conditions, only the Ascl1/Myt1l condition is sufficient to convert mouse embryonic fibroblasts into neuron-like cells, which exhibited characteristic neuronal morphology and Tau expression (FIGS. 2-3). Consequently, the Ascl1/Myt1l condition was used as the baseline for chemical screening.

To conduct the chemical screening, Tau-EGFP mouse embryonic fibroblasts were used that were transduced with an Ascl1/Myt1l coding region that was under control of tet operator. These cells were plated at 4,000 cells/well in 384-well plates containing chemically defined N2B27 media. After overnight incubation, the cells were treated for seven days with doxycycline to induce Ascl1/Myt1l expression and also contacted with individual compounds selected from a drug collection containing over 3000 compounds. The media was then replaced with compound-free standard neuronal media. Cells were fixed at day 14 then analyzed for Tau-EGFP expression and neuronal morphology by high content imaging (FIG. 4A and FIG. 3).

Several primary hits were further confirmed in a dose-dependent manner in larger well format. Compounds identified by this screen to induce Tau-EGFP expression and a neuronal morphology included CHIR99021 (GSK3 inhibitor), SB431542 (ALK4/5/7 inhibitor), Y27632 (ROCK inhibitor), KHS2 (neuronal differentiation enhancer), TSA (HDAC inhibitor), DHA (an omega-3 fatty acid), CD1530 (RARγ receptor agonist), IB-MECA (A3 adenosine receptor agonist), Nitrendipine (L-type calcium channel blocker), ACPD (mGlu receptor agonist), TDMB (Tropanyl-3,5-dimethylbenzoate, 5-HT3 antagonist), CTPB (p300 activator), and Rolipram (PDE4 inhibitor).

Figure 4D:
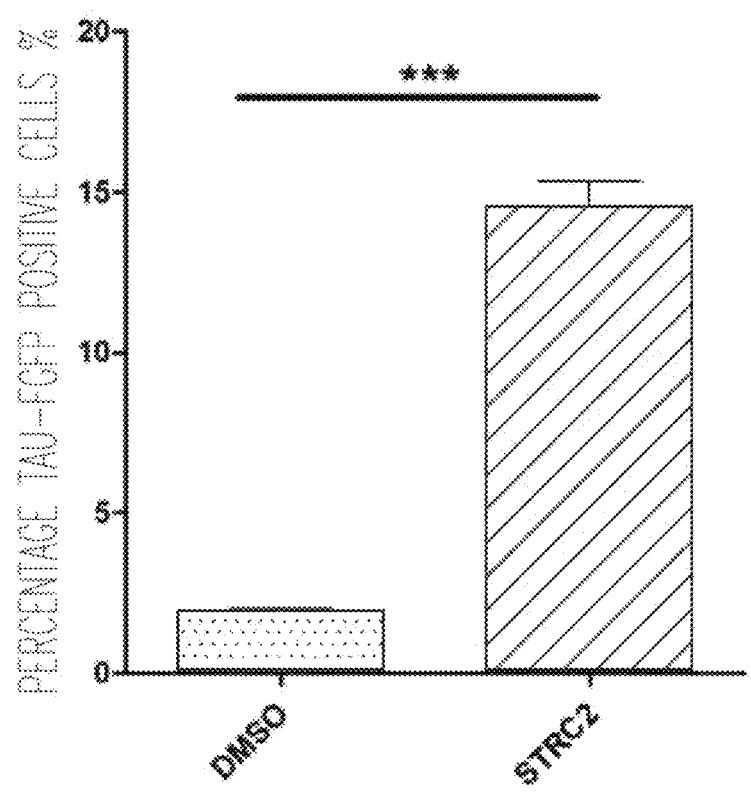
Figure 4E:
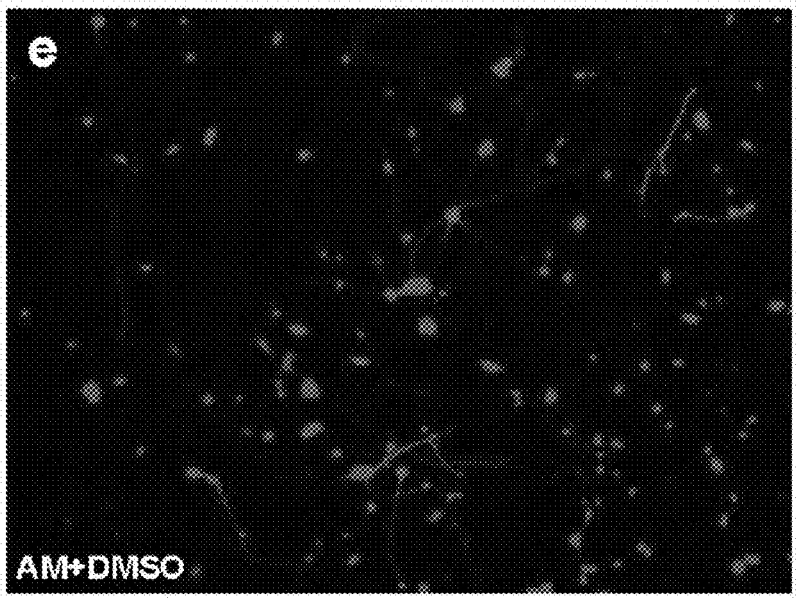
FIG. 4E-4F illustrate Tuj1 expression in Ascl1-Myt1l-expressing cells treated with either DMSO (control) or STRC2 on day 14. Bar 50 µm.
Figure 4F:
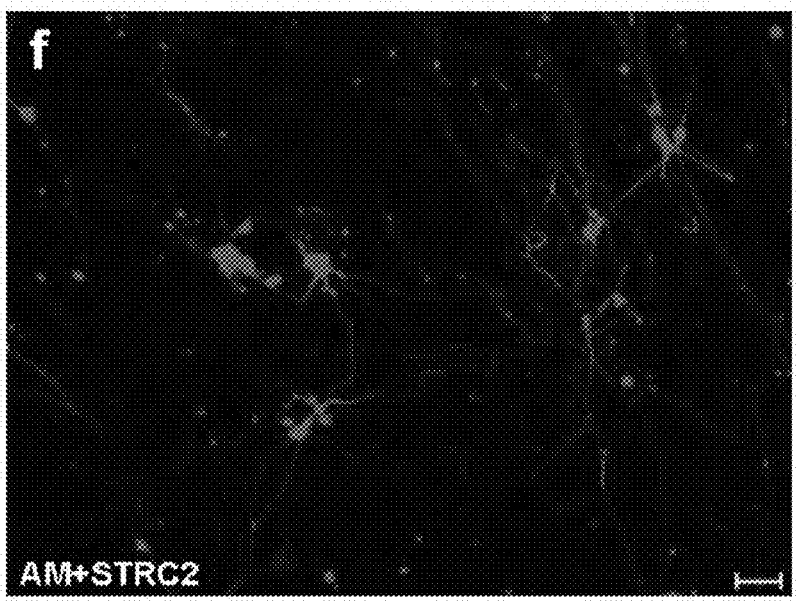
Figure 4G:
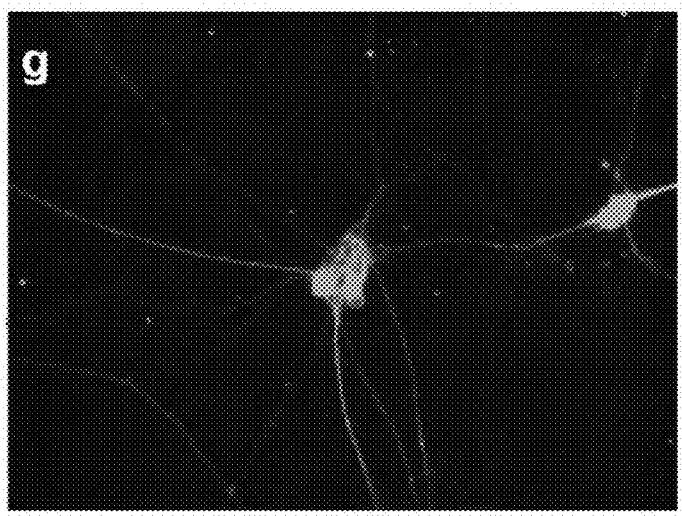
FIGS. 4G-4O show that the STRC2-treated cells expressed neuronal markers by day 12.

Subsequent examination of various combinations of these compounds led to the establishment of a cocktail of five small molecules (i.e., SB431542, TSA, Rolipram, CHIR99021, and CTPB, hereinafter referred to as "STRC2") as the most efficient condition to promote neuronal reprogramming in cells expressing Ascl1 and Myt1l. In comparison to the baseline condition with only Ascl1/Myt1l expression, addition of the STRC2 cocktail enhanced the reprogramming efficiency by 4-fold as indicated by the numbers of Tau-EGFP expressing cells (FIG. 4B-4D). In addition, these STRC2-treated Ascl1/Myt1l cells also exhibited more mature neuronal properties such as more highly branched neurites (FIG. 4E-4F).

Figure 4H:
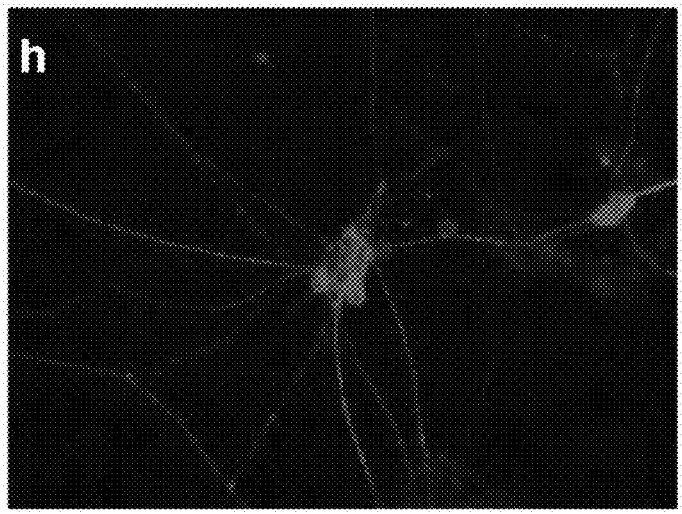
Figure 4I:
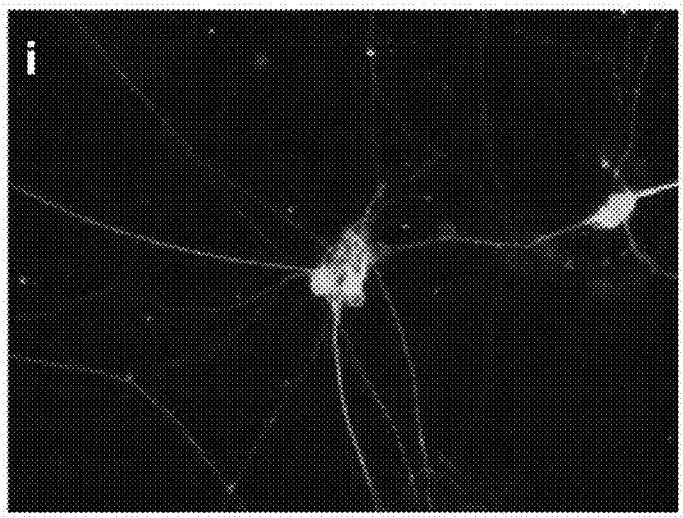
Figure 4J:
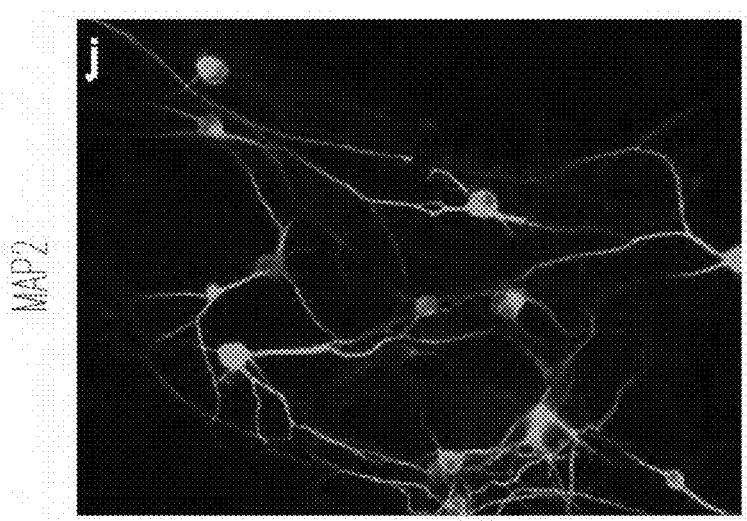
Figure 4K:
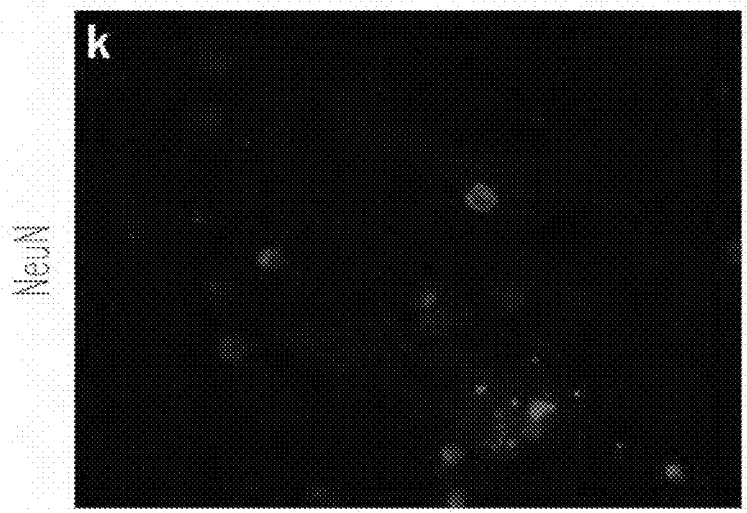
Figure 4L:
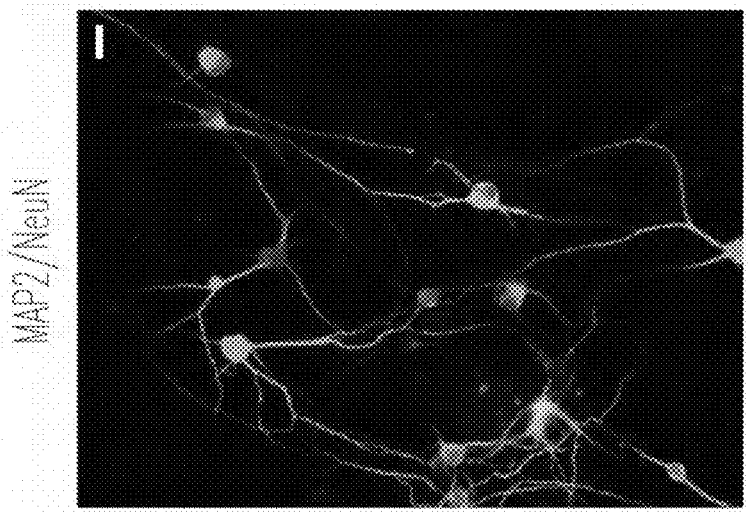
Figure 4M:
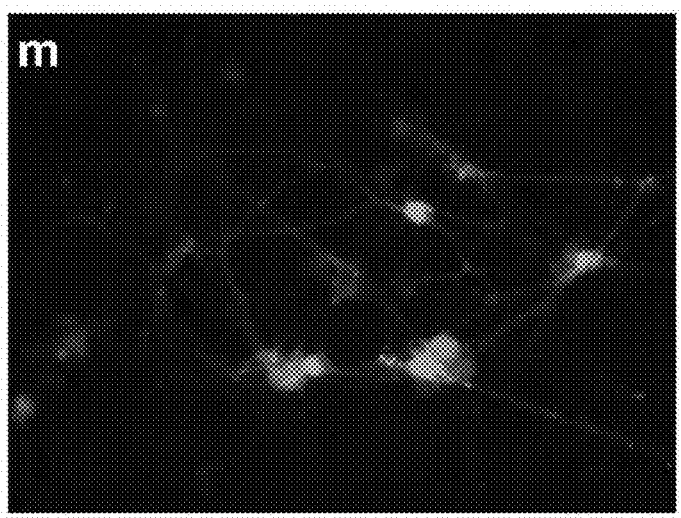
Figure 4N:
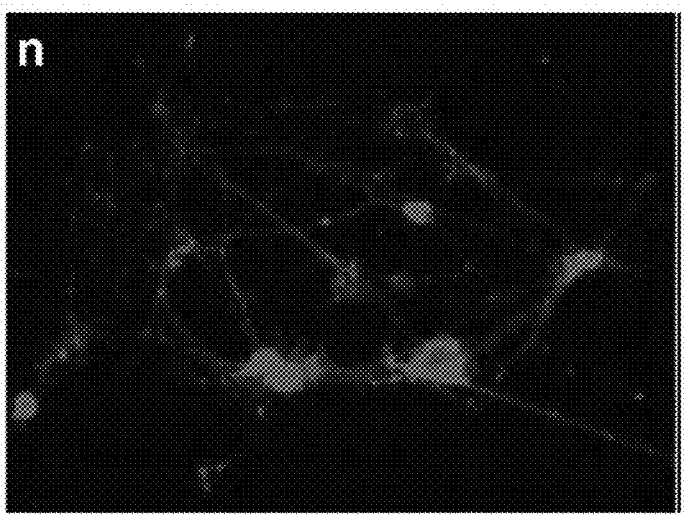
Figure 4O:
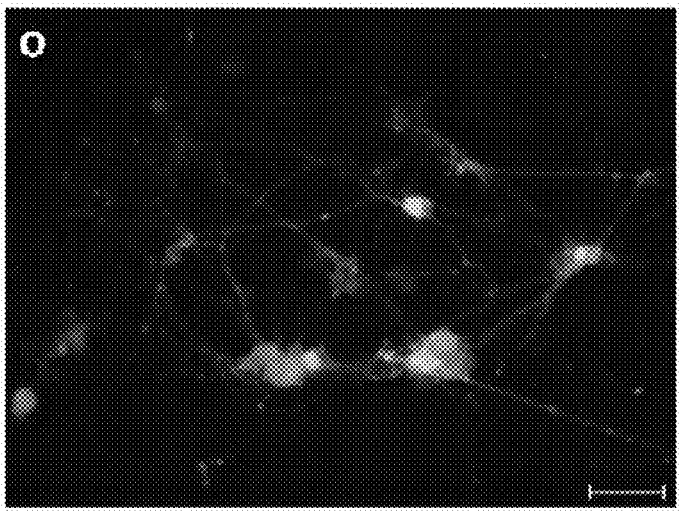
Figure 5A:
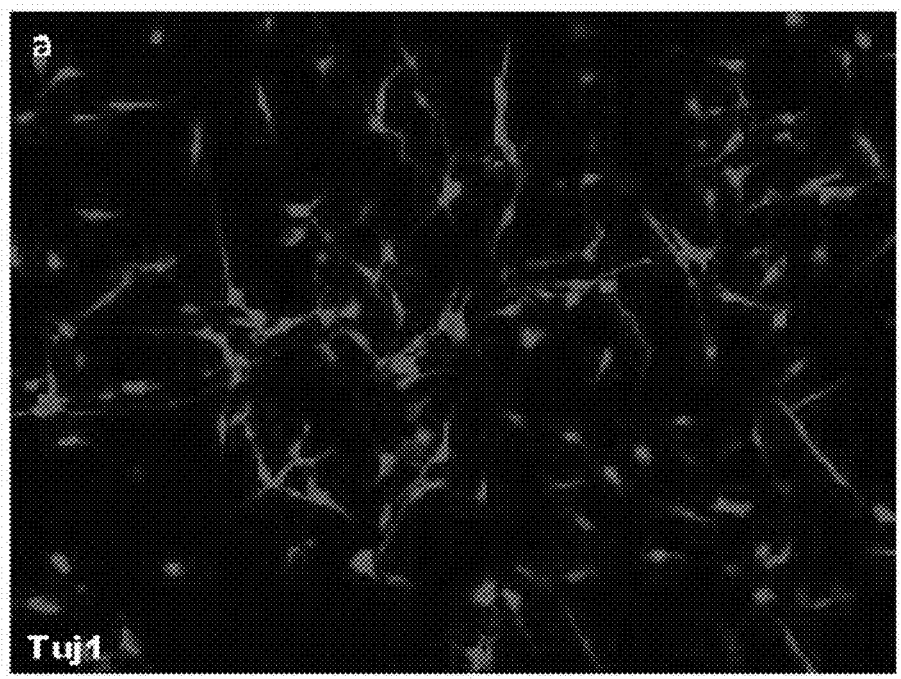
FIGS. 5A-5B illustrate that Ascl1/Myt1l-expressing cells expressed Tuj1 after 3 days of STRC2 treatment.
Figure 5B:
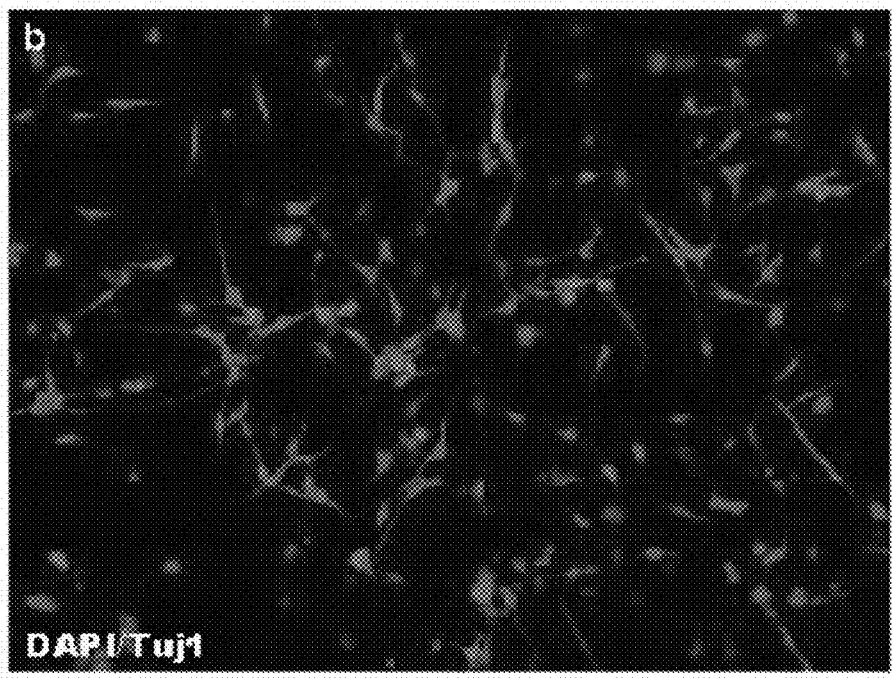
Figure 6A:
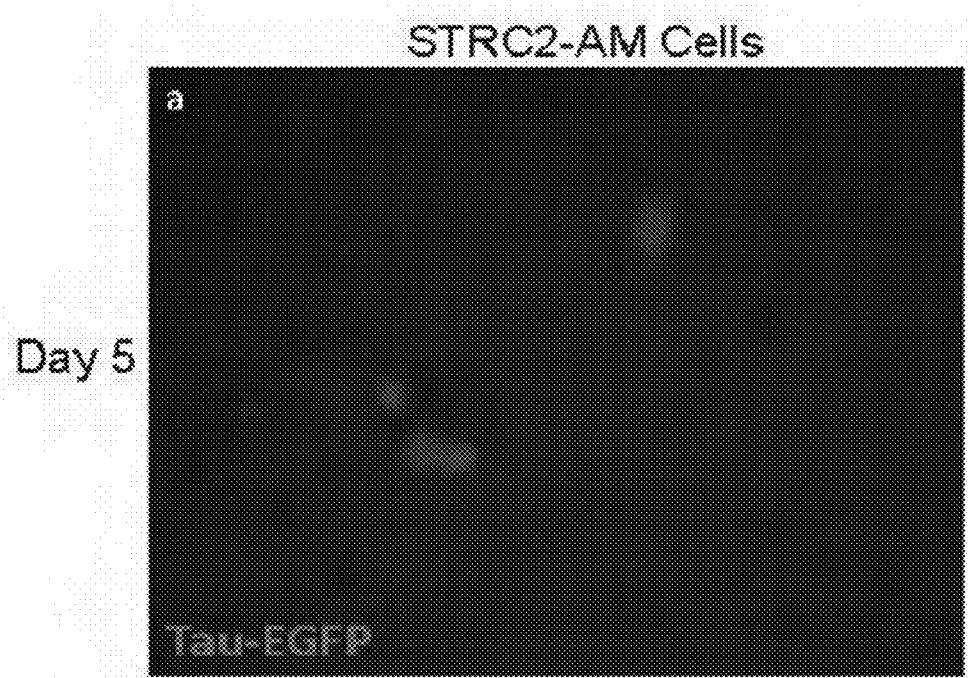
FIG. 6A-6F illustrates Tau-EGFP expression in STRC2-treated Ascl1/Myt1l-expressing cells and in STRC2-treated Ascl1-expressing cells at different time points.
Figure 6B:
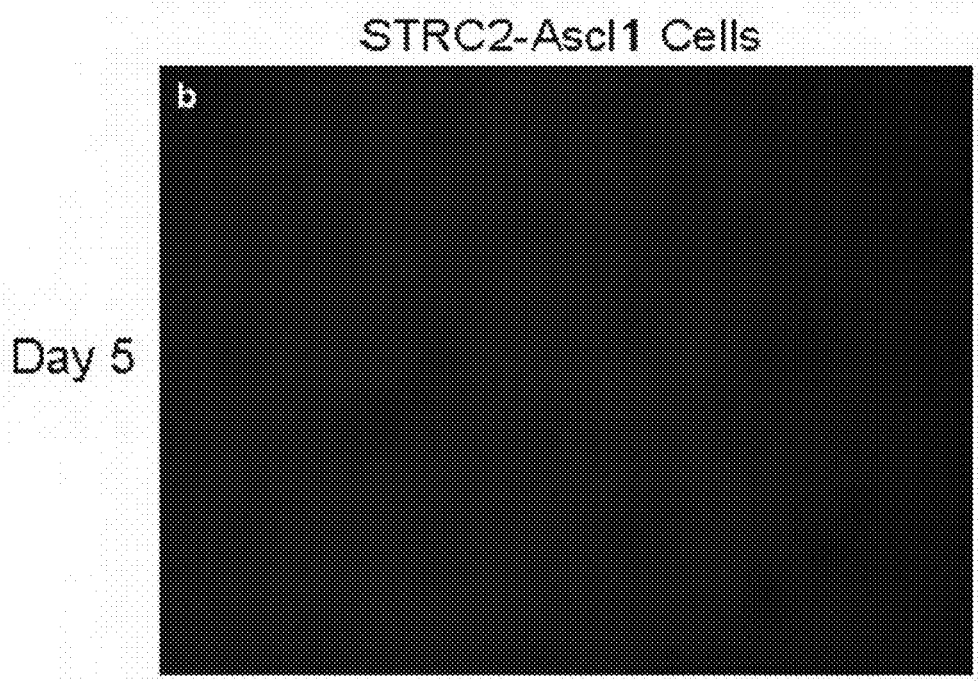
Figure 6C:
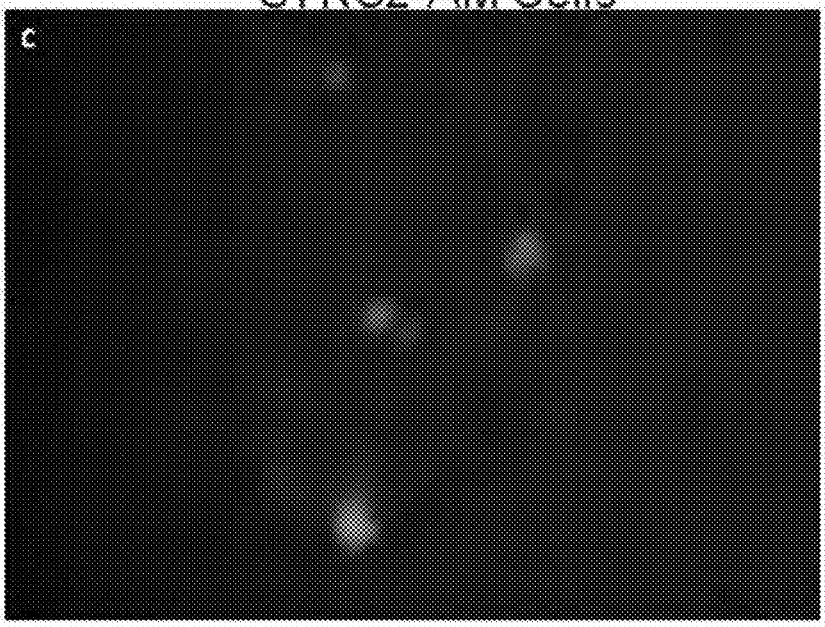
Figure 6D:
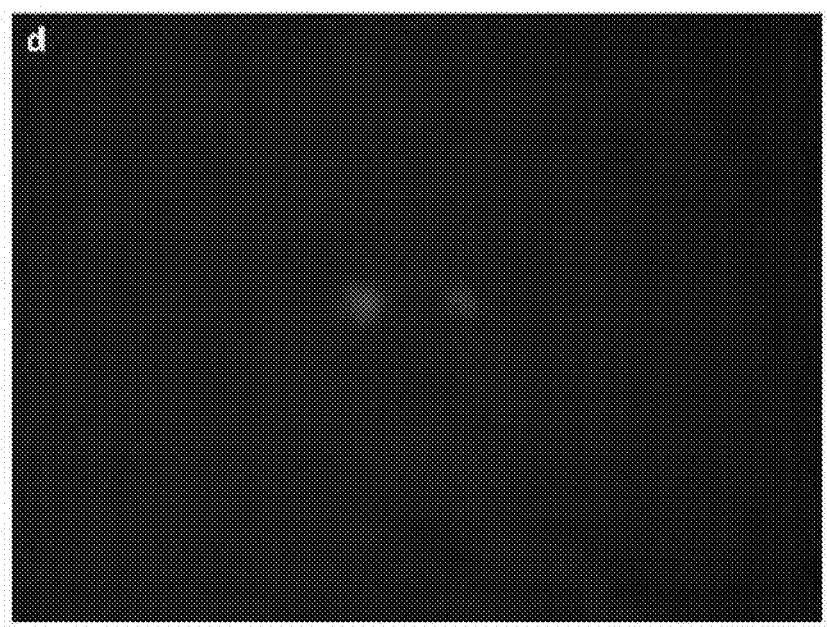
Figure 6E:
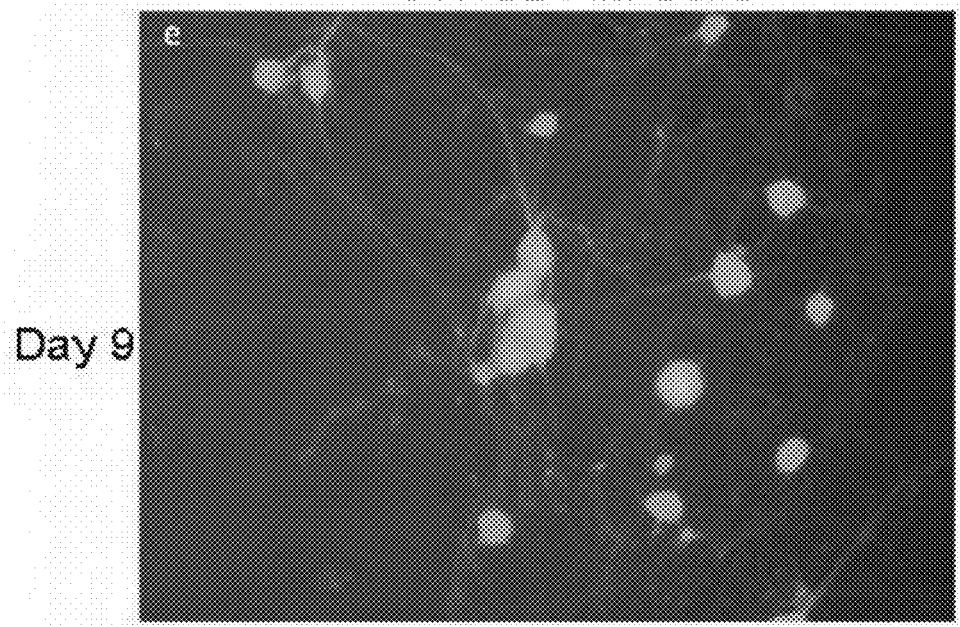
Figure 6F:
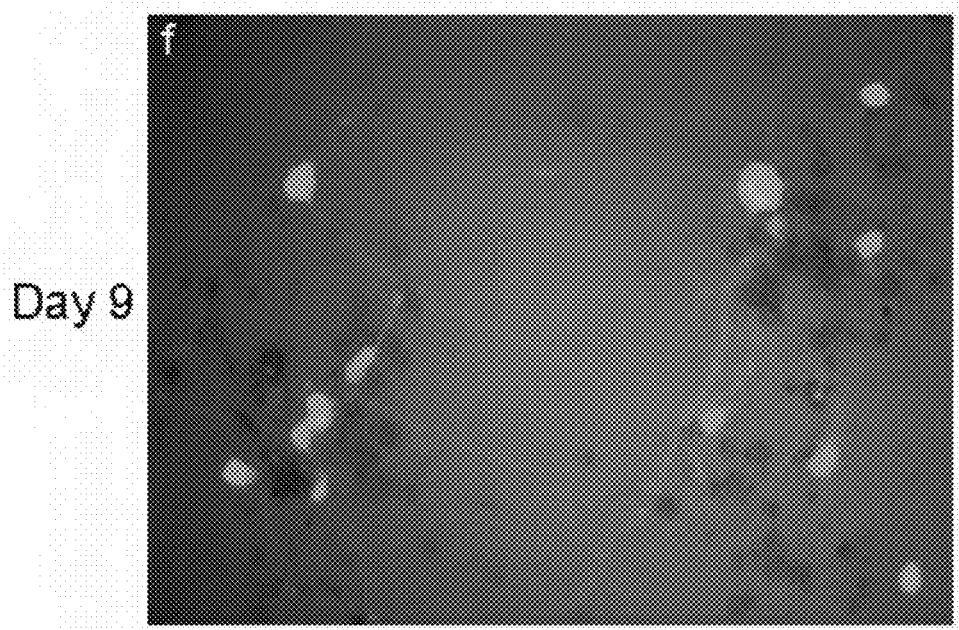

To further characterize STRC2-enhanced neuronal reprogramming after Ascl1/Myt1l expression, live cell imaging of cell morphology and Tau-EGFP expression was recorded over the course of reprogramming and additional neuronal markers were examined at different time points by immunocytochemistry. Remarkably, it was found that even within 2-3 days of STRC2 treatment, more than 50% of the MEF cells started to undergo dramatic morphological changes and exhibit small, compact cell bodies with mono- or bipolar projections and βIII-tubulin expression (FIG. 5). Tau-EGFP positive neurons appeared with characteristic neuronal morphology, consisting of multiple neurite extensions and elaborate branching as early as 9 days after Ascl1/Myt1l induction with STRC2 treatment (FIG. 6). In 12 days, most of Ascl1/Myt1l cells also expressed additional mature neuronal markers, including βIII-tubulin, MAP2, NeuN, and Synapsin I (a marker indicative of synapse formation) (FIGS. 4G, 4J, 4K, and 4N). Markers for neuronal subtypes, including vGlut1 (glutamatergic neuronal subtype) and GAD65 (GABAergic neuronal subtype) can be detected in STRC2-Ascl1/Myt1l cells as well (FIG. 4H, 4M).

To functionally characterize Ascl1/Myt1l-induced neuronal cells under the STRC2 condition, the electrophysiological properties were examined. From EGFP positive STRC2-Ascl1/Myt1l neuronal cells 12 days after induction, average membrane potential of $-53.67 \pm 2.698$ mV and input resistance of $436.5 \pm 56.13$ MΩ was recorded (Table 1), which are similar to that of typical mature neurons (i.e. $-65$ mV and 300 MΩ for mouse mature neurons).

TABLE 1

Properties of Cells Over Time

| Cell Type | $R_m$ (MΩ) ±SEM | $C_m$ (pF) ±SEM | $V_{rest}$ (mV) ±SEM | AP % | Trains % | sEPSC % | sIPSC % |
|---|---|---|---|---|---|---|---|
| Ascl1 Day 12 (n = 13) | 666.31 ± 71.47 | 15.29 ± 1.270 | −48.92 ± 1.936 | 76.92 | 61.53 | 7.69 | 0.00 |
| Ascl1 Day 18 (n = 12) | 495.83 ± 62.66 | 26.58 ± 3.639 | −52.5 ± 1.215 | 100.00 | 83.33 | 33.33 | 0.00 |
| Ascl1 + Myt1l Day 12 (n = 22) | 436.5 ± 56.13 | 29.43 ± 3.872 | −53.67 ± 2.698 | 81.81 | 81.81 | 18.18 | 0.00 |
| Ascl1 + Myt1l Day 18 (n = 13) | 309.77 ± 23.62 | 27.06 ± 3.437 | −55.4 ± 4.202 | 100.00 | 100.00 | 46.20 | 7.69 |
| miB- Day 6 (n = 19) | 1235.06 ± 194.0 | 41.89 ± 3.190 | −26.76 ± 2.265 | 89.50 | 73.68 | 0.00 | 0.00 |

Figure 4P:
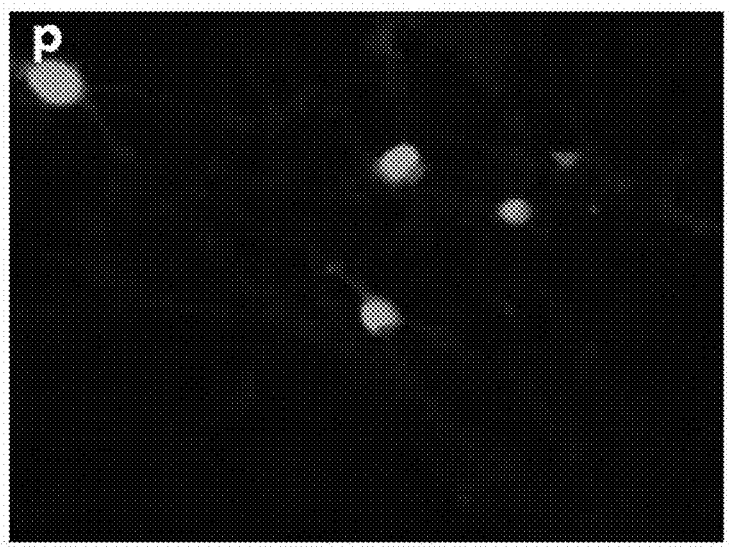
FIG. 4P illustrates that Tau-EGFP positive, Ascl1-Myt1l cells form after 12 days of STRC2 treatment, as visualized by live imaging.
Figure 4Q:
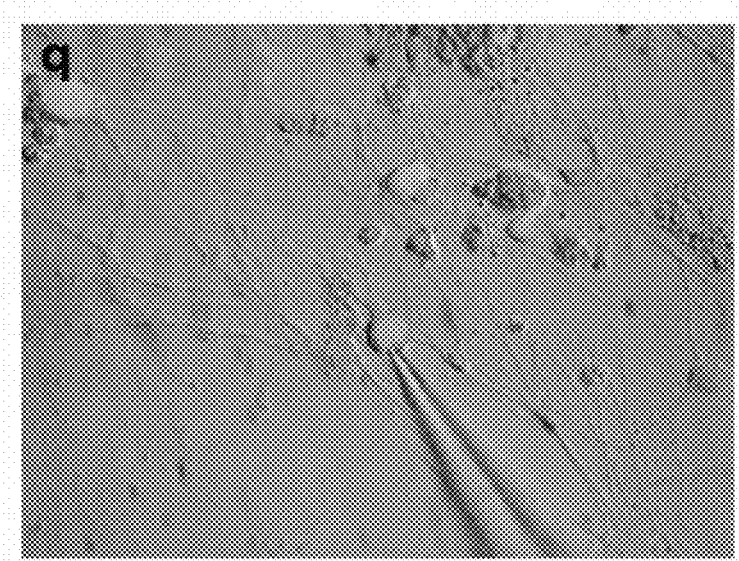
FIG. 4Q shows patch clamp of one of the same cells shown in FIG. 4P.
Figure 4R:
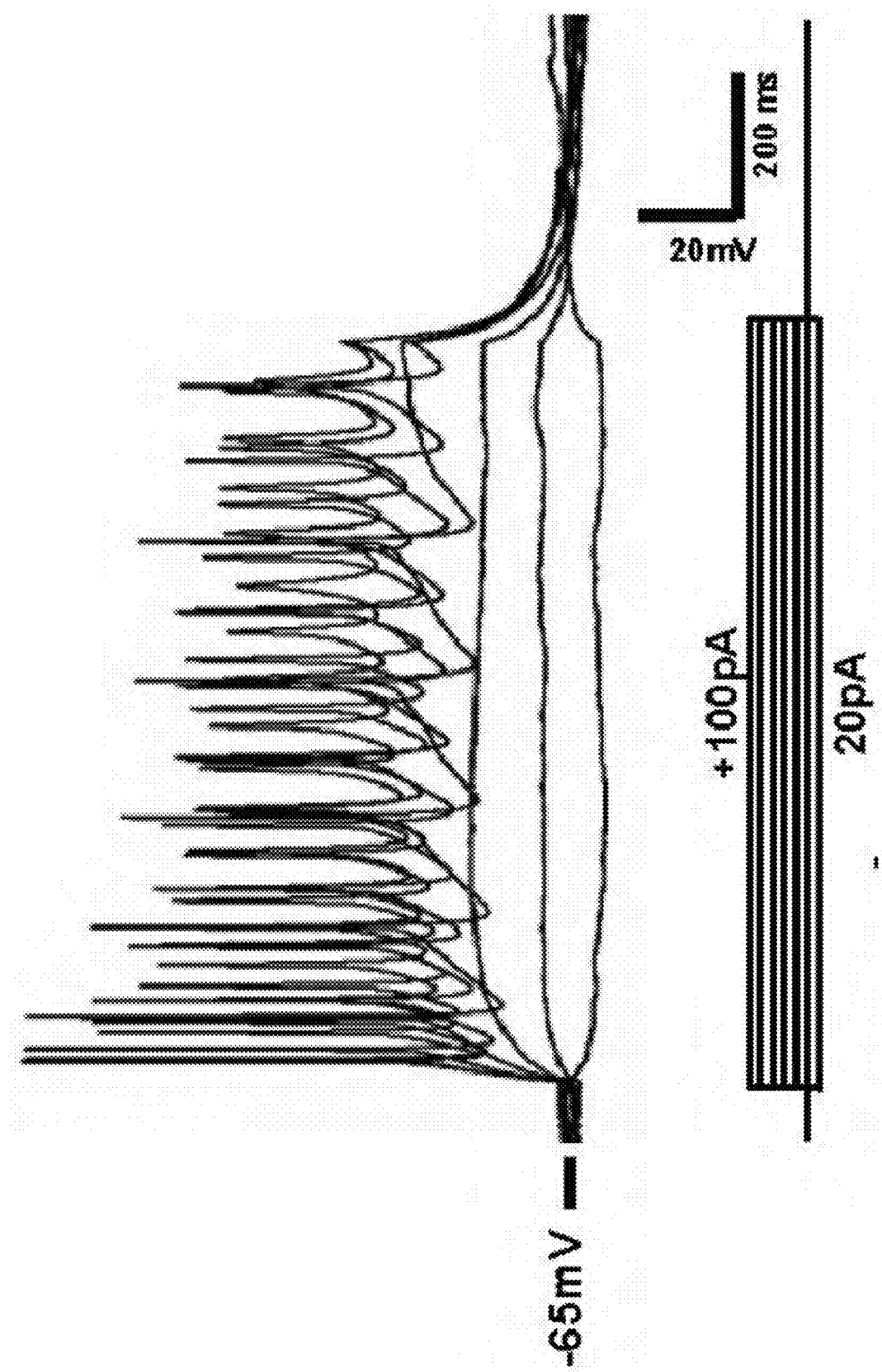
FIG. 4R shows trains of action potentials (APs) that were evoked by step-wise increase of holding current of the patch clamped cell shown in FIG. 4R.
Figure 4S:
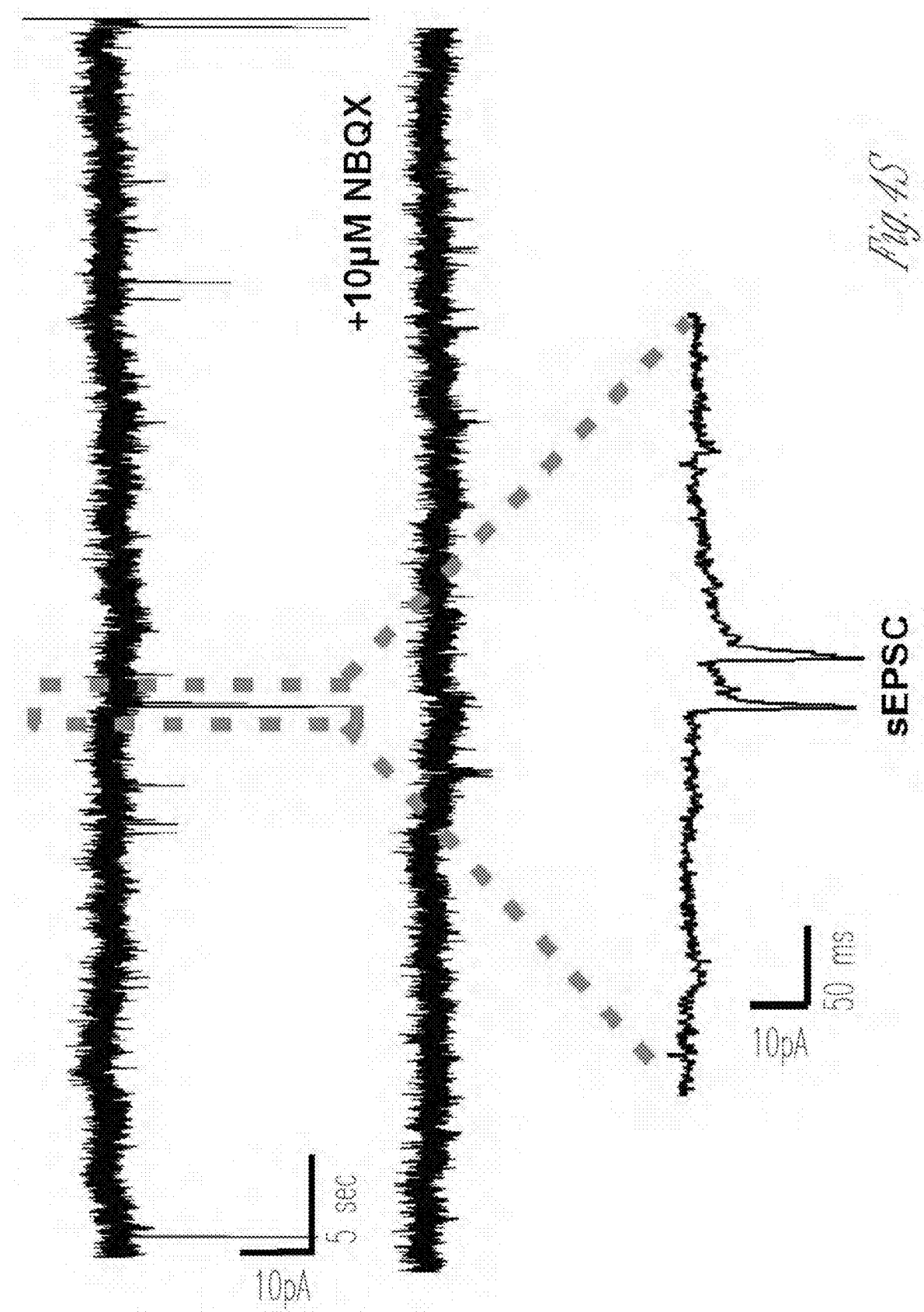
FIG. 4S shows spontaneous excitatory postsynaptic current (sEPSC) (Vm=−70 mV) exhibited by the Ascl1/Myt1l cells after STRC2 treatment.
Figure 4T:
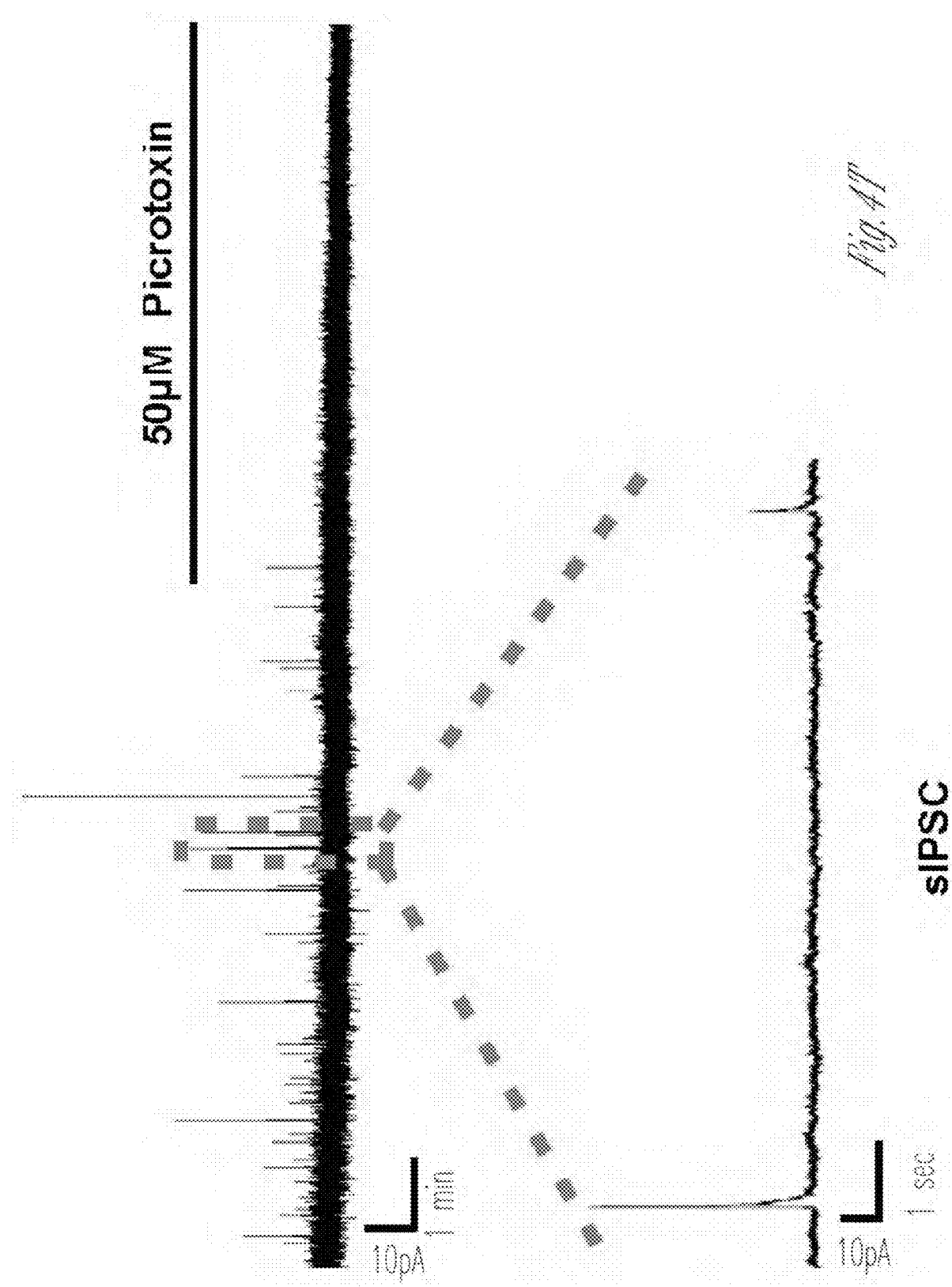

When depolarizing current steps were injected into these cells, action potentials could be readily detected in all the analyzed EGFP positive neurons and trains of action potential could be readily detected in most of the these neurons (18 out of 22 recorded neurons). The recorded cells were further analyzed by voltage clamp and showed typical fast-inactivating sodium currents and outward potassium currents (FIG. 4P-4R). In addition, the STRC2-Ascl1/Myt1l cells exhibited spontaneous excitatory postsynaptic current (sEPSC), which were blocked by specific AMPA receptor antagonist NBQX (FIG. 4S) and inhibitory postsynaptic currents (sIPSCs) (FIG. 4T) that could be subsequently blocked by the $GABA_A$ receptor antagonist picrotoxin (PTX), indicating that these cells had formed functional synapses and been integrated into a functional network. Taken together, MEF cells can be rapidly and efficiently converted to mature and functional neurons by the treatment of STRC2 and Ascl1/Myt1l induction.

Experiments were then performed to ascertain whether the STRC2 cocktail could truly substitute neuronal transcription factors and enable reprogramming with a single factor, Ascl1 alone, which on its own does not generate any neurons at all even starting with large number of fibroblasts and after extended culture. Therefore, if it works, the STRC2 condition would represent a true enabling condition, rather than simply enhancing a permissive reprogramming condition. Unprecedented results were observed where the activation of Tau-EGFP reporter started in some of the Ascl1-tranduced MEFs as early as 7 days after STRC2 treatment (FIG. 6).

Figure 7A:
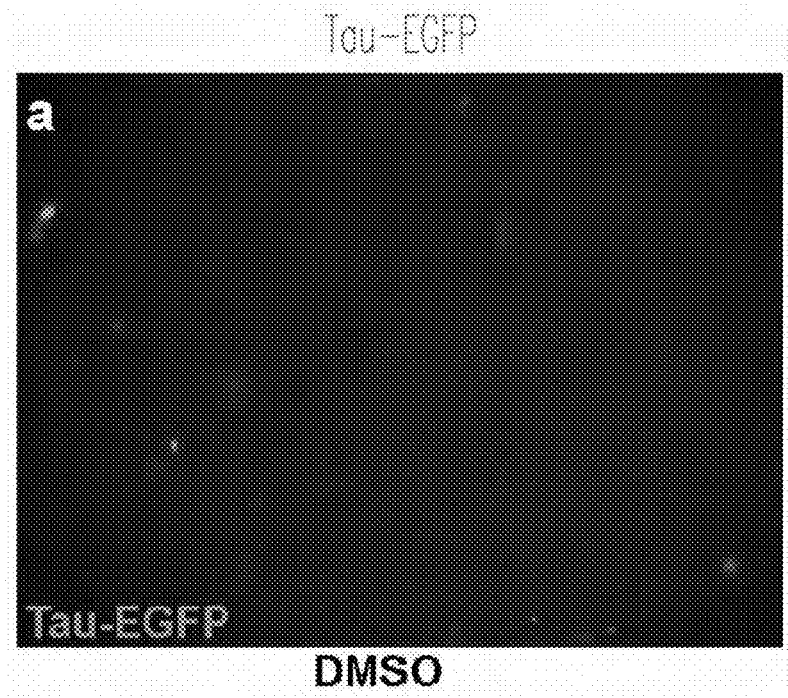
Figure 7B:
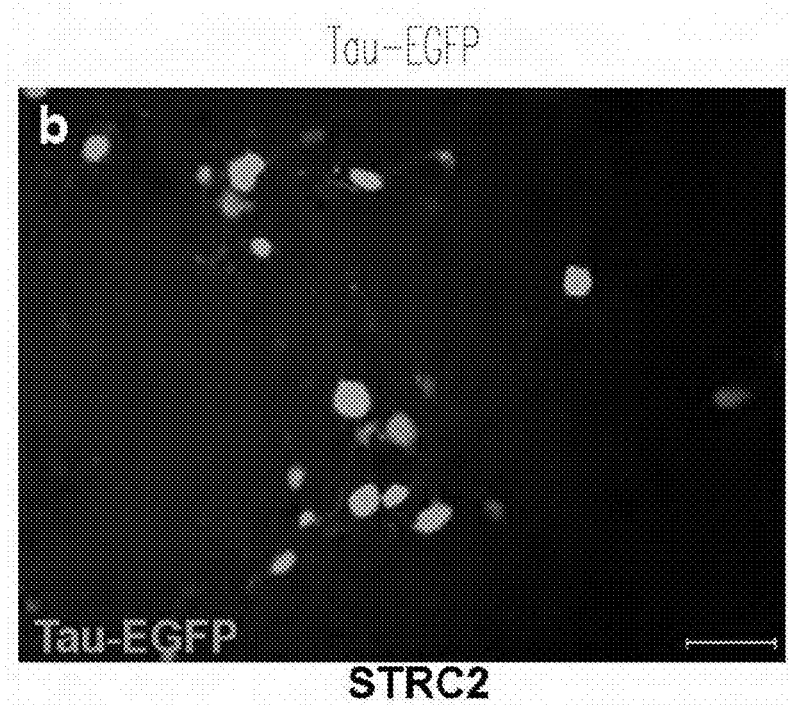
Figure 7C:
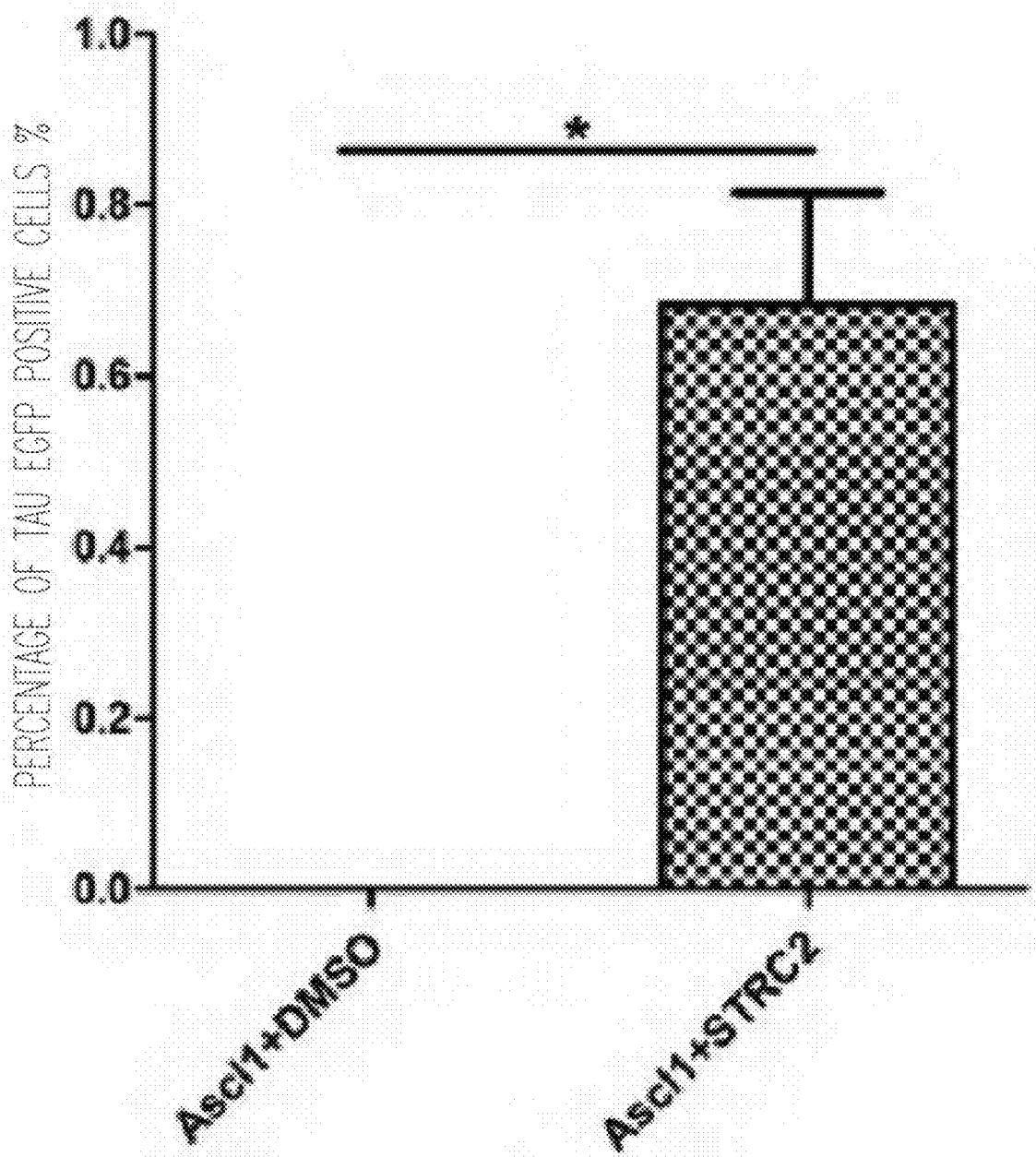
Figure 7D:
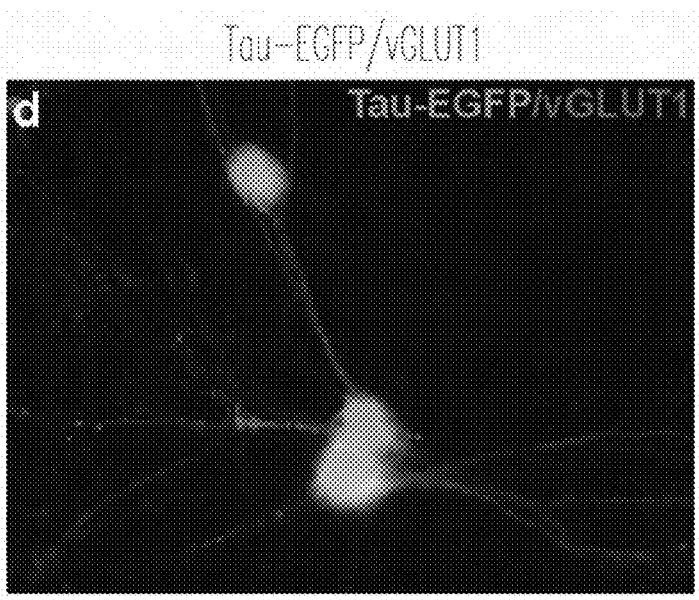
Figure 7E:
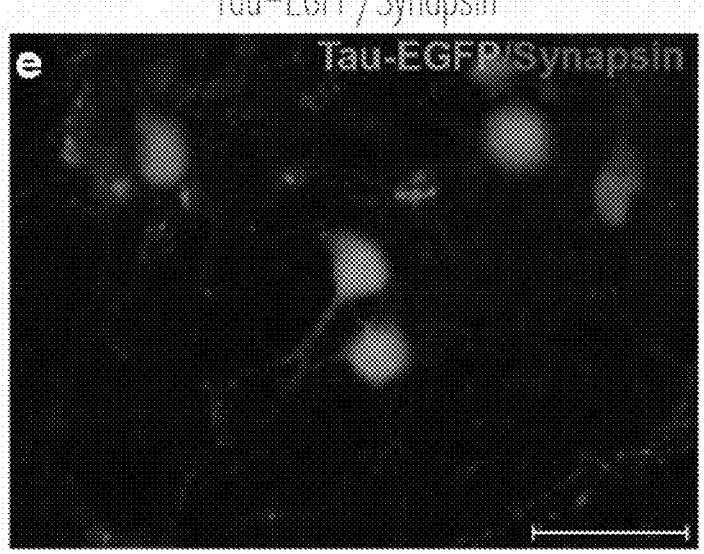
Figure 7F:
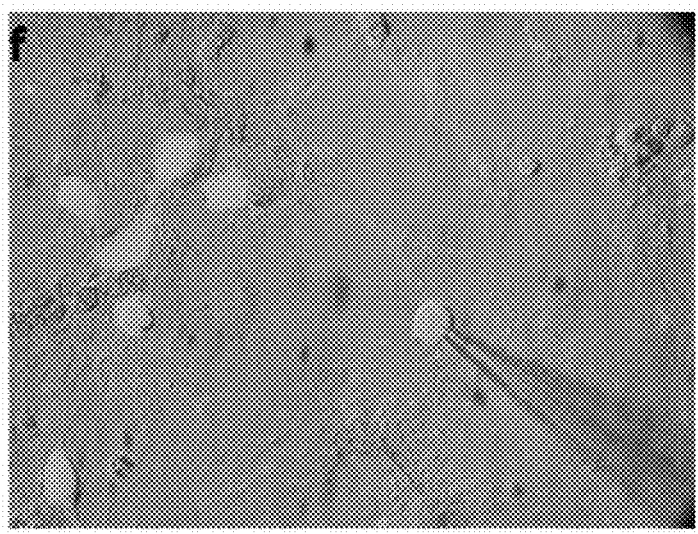
Figure 7B:
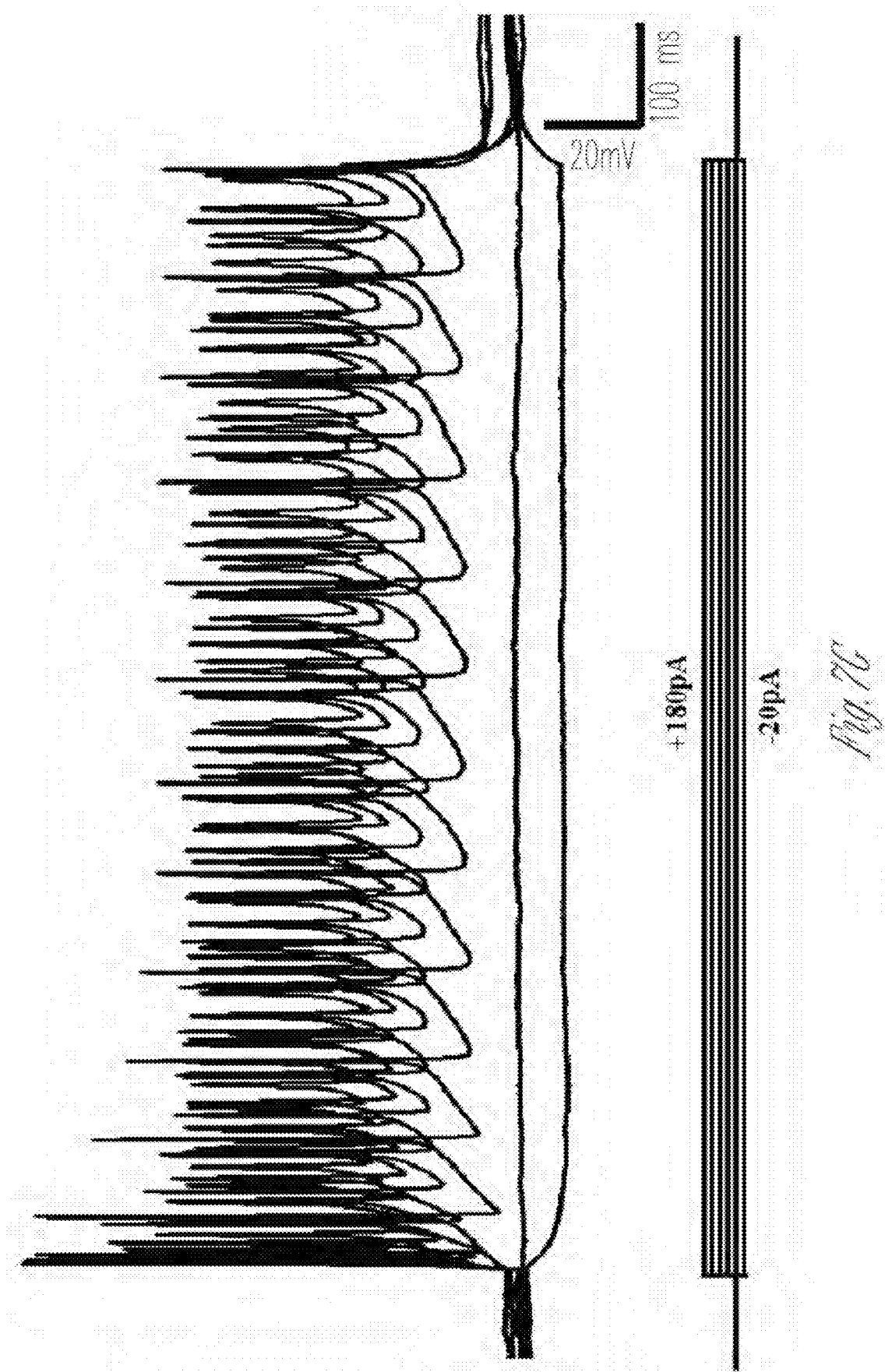
Figure 7H:
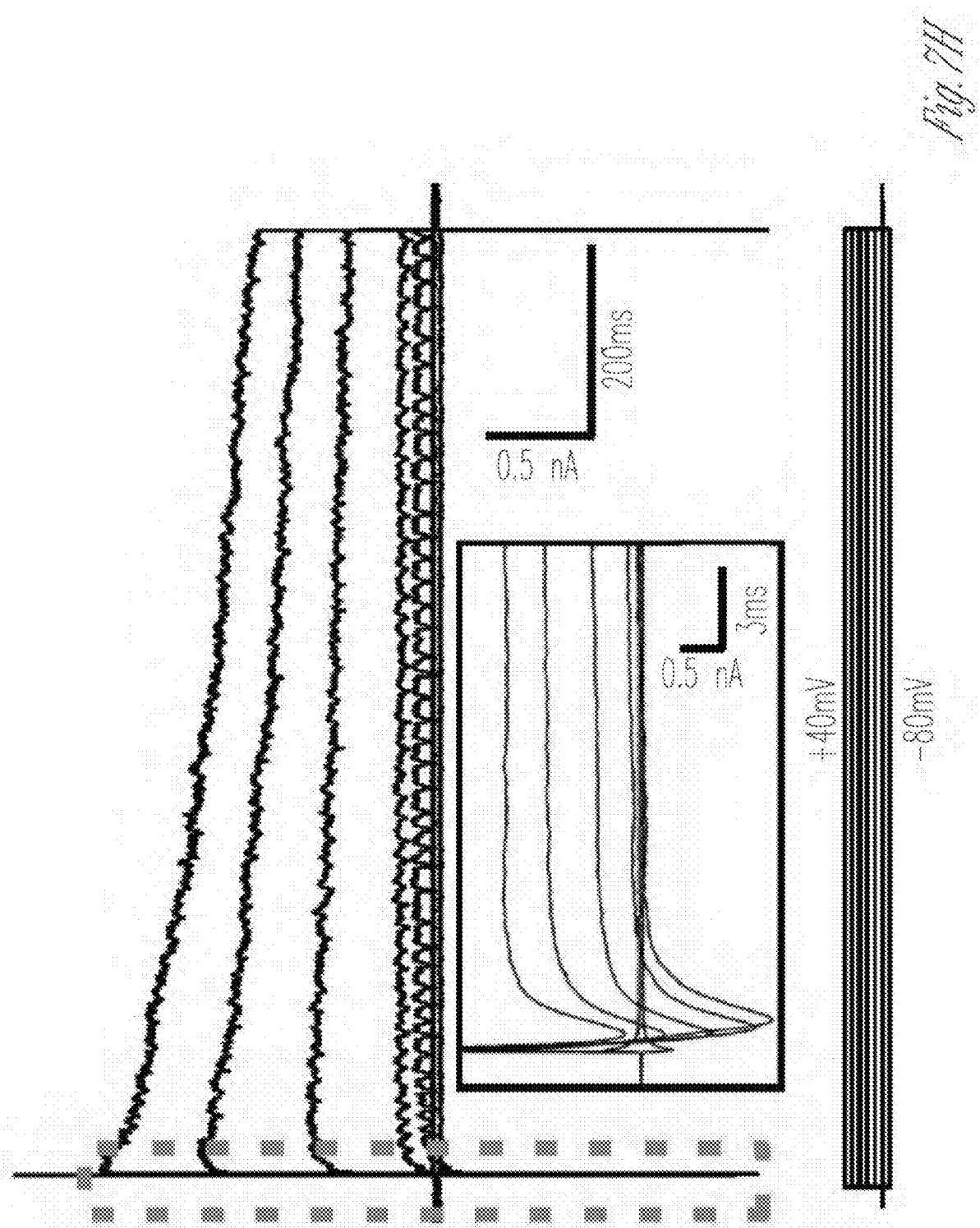
Figure 71:
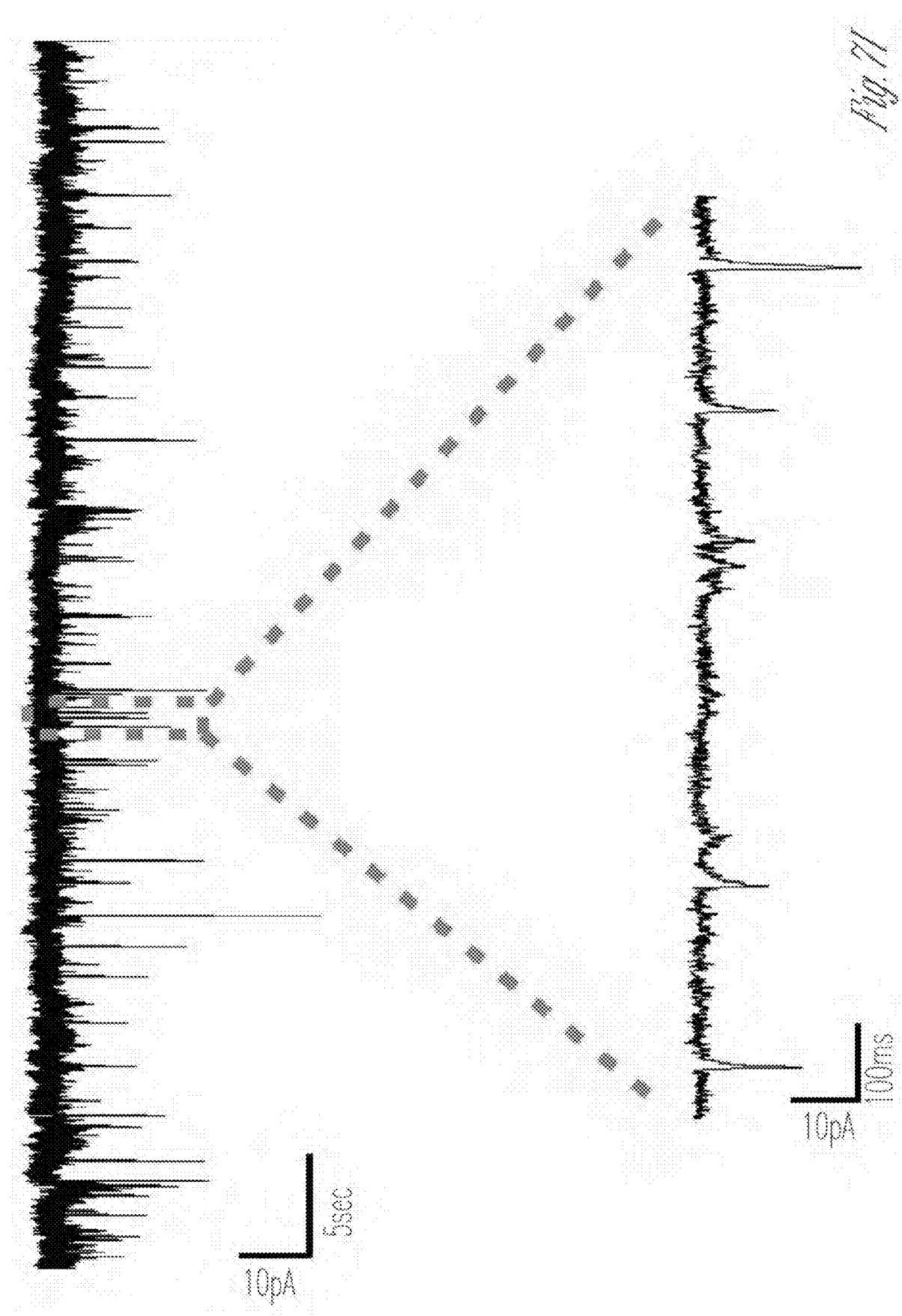
Figure 7J:
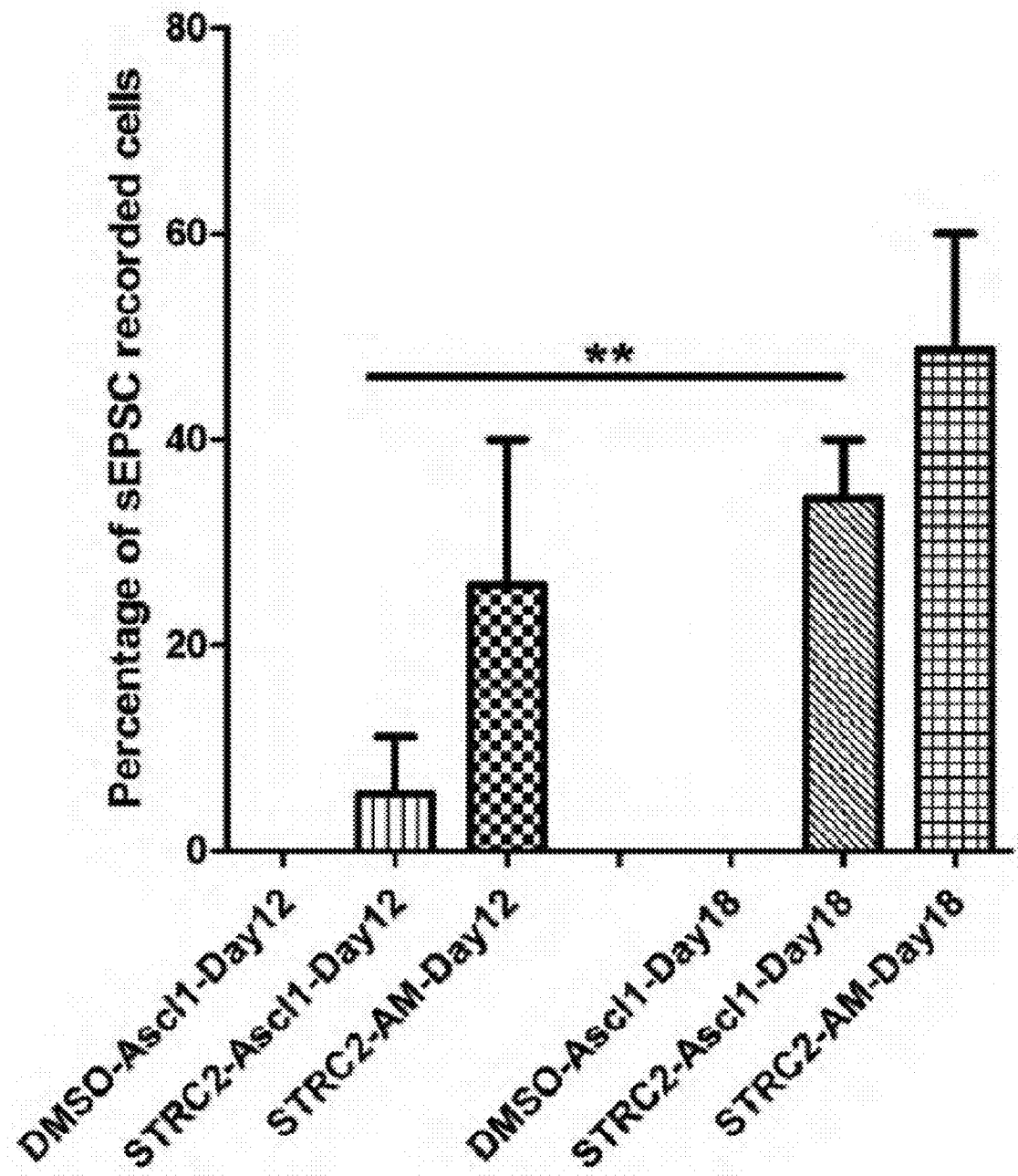
Figure 8A:
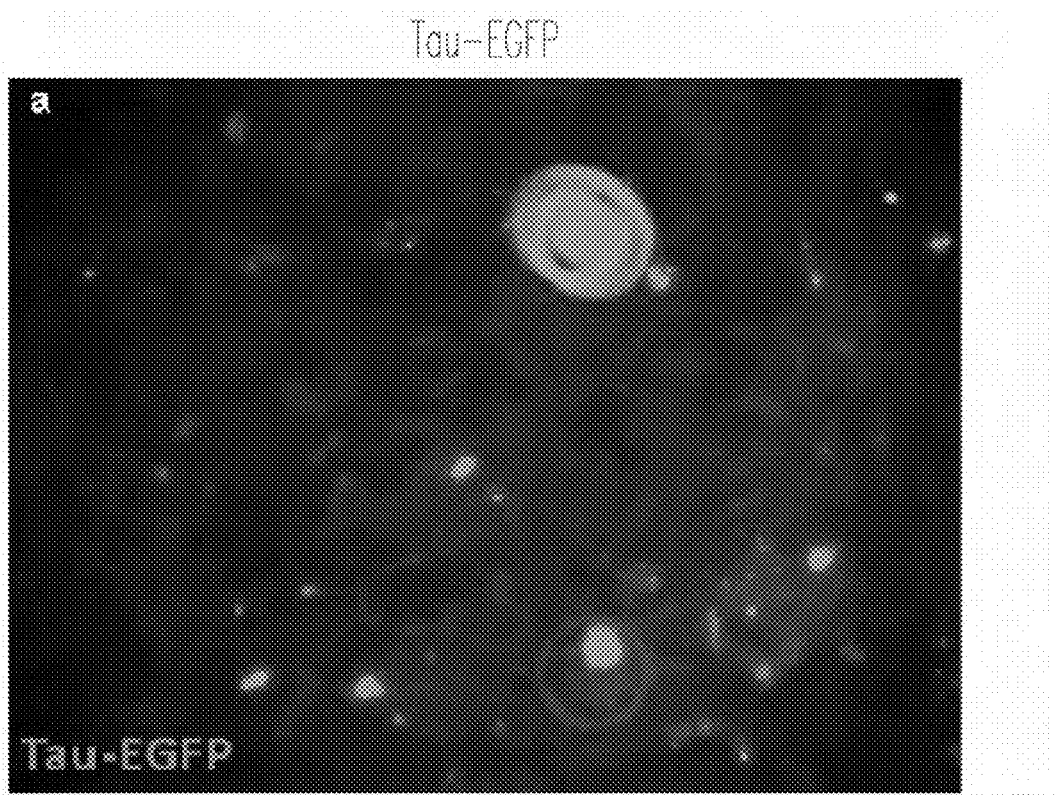
FIG. 8A-8B illustrate that STRC2 can also enable Ascl1-MEFs to be fully reprogrammed.
Figure 8B:
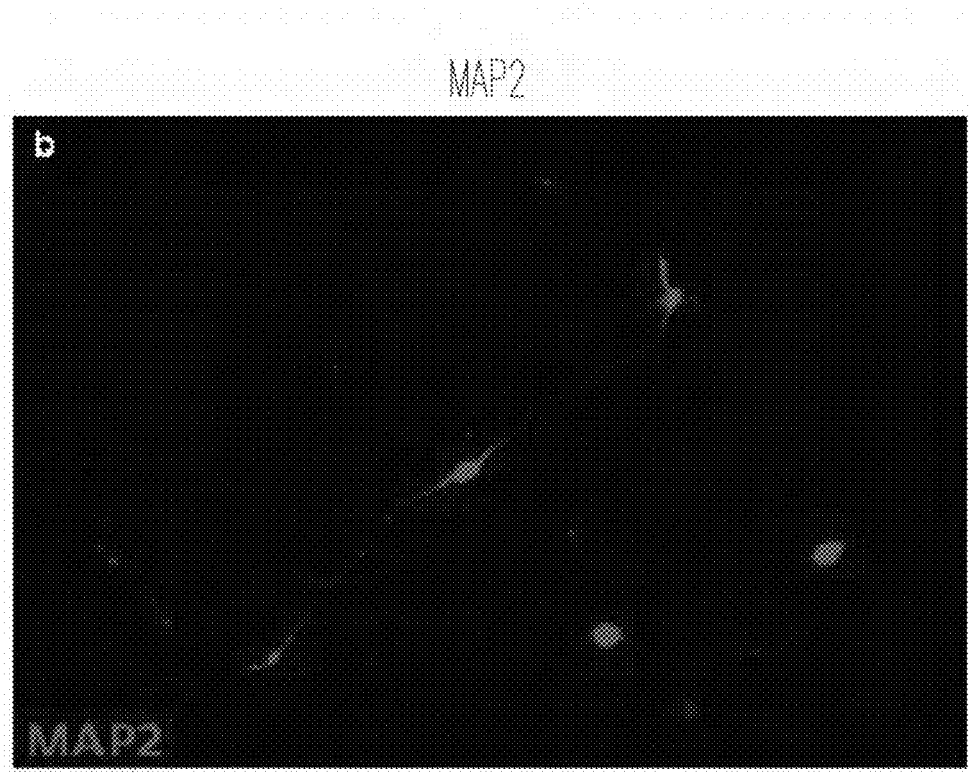
Figure 9A:
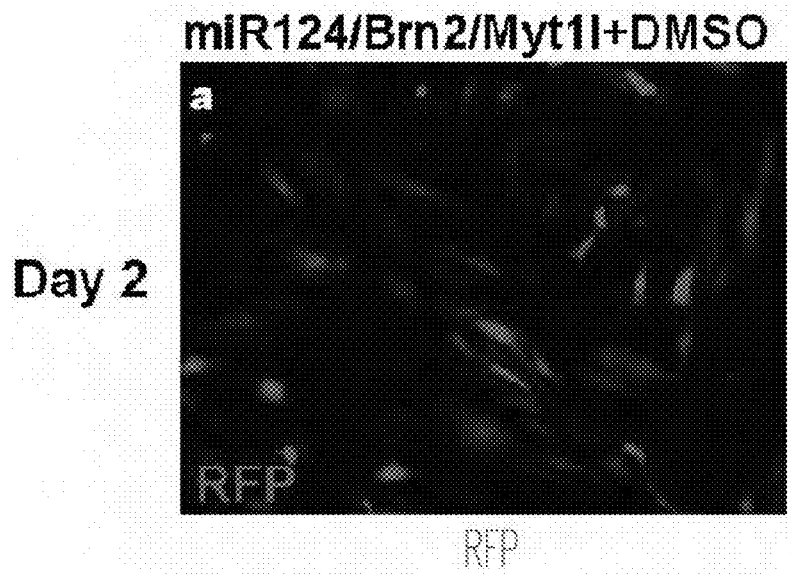
Figure 9B:
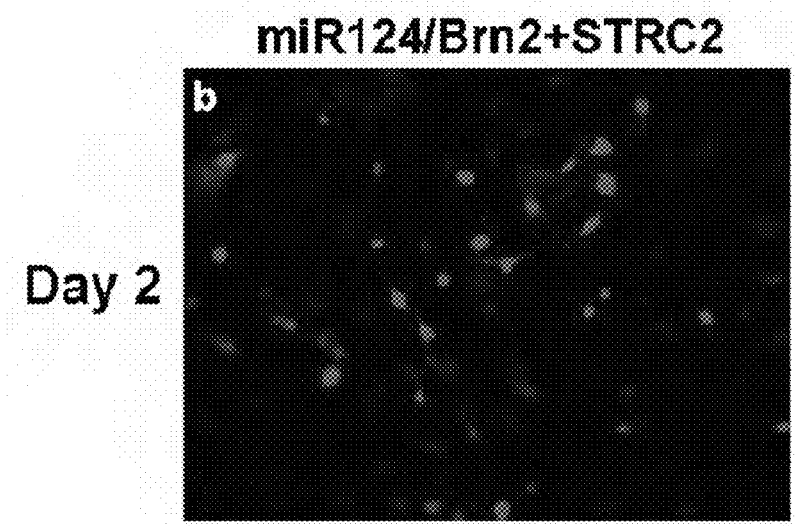
Figure 9C:
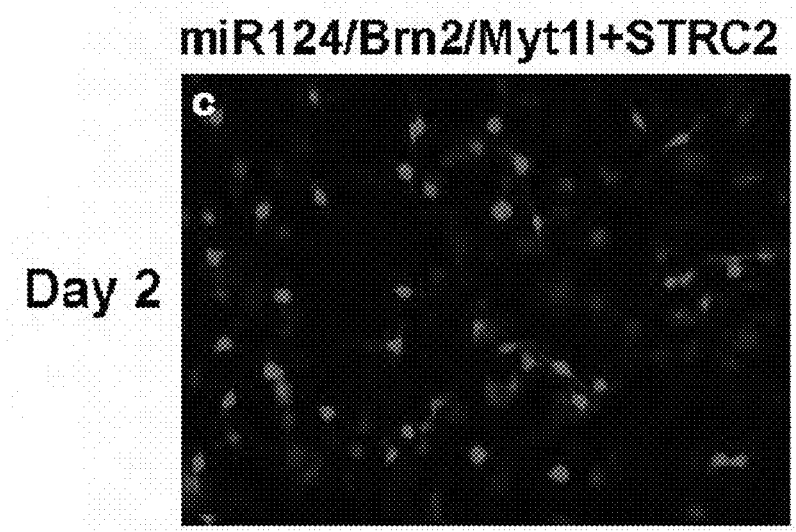
Figure 9G:
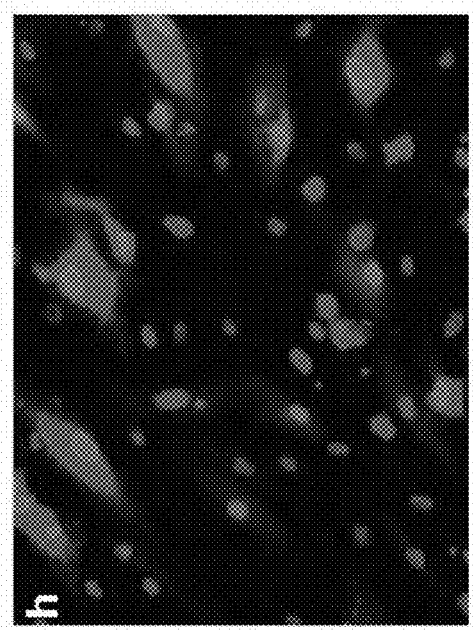
FIGS. 9G and 9H show that no MAP2-positive cell was found in DMSO-treated miR124-RFP/Brn2 human foreskin fibroblasts (hFFs) on day 6. In contrast.
Figure 9H:
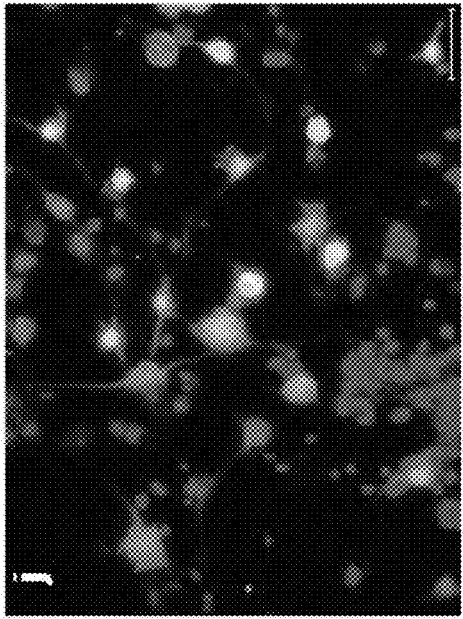
Figure 9G:
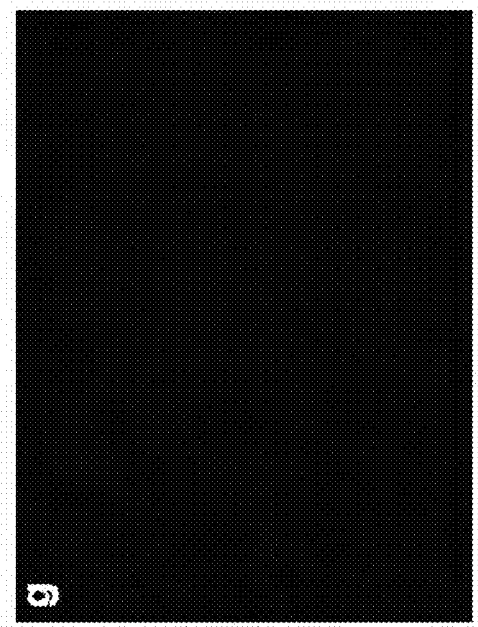
Figure 9I:
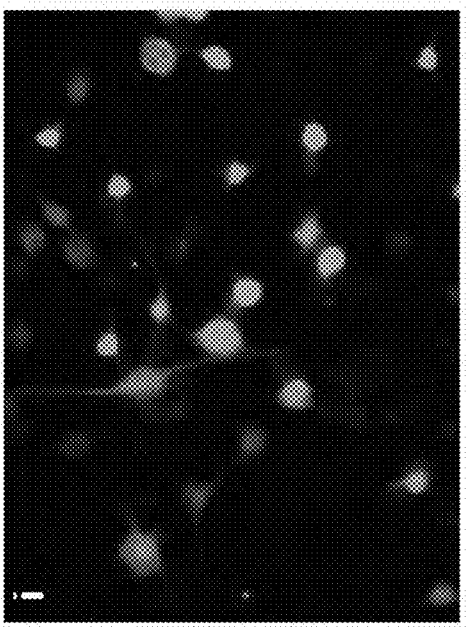
Figure 9K:
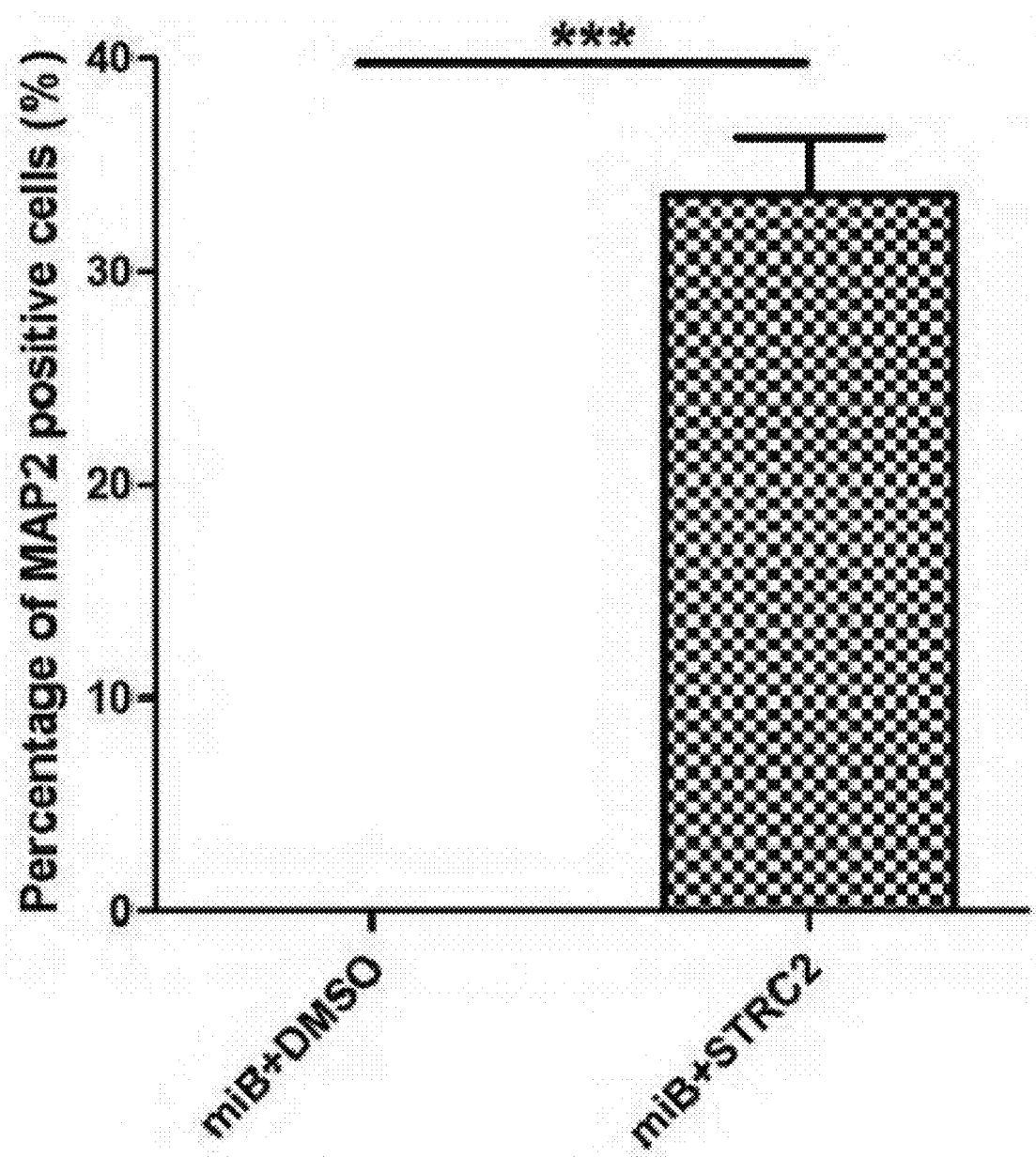
FIG. 9K graphically illustrates the percentage of MAP2 positive cells after DMSO and STRC2 treatment for 6 days as analyzed using Student's t-test (p value=0.000239).
Figure 9L:
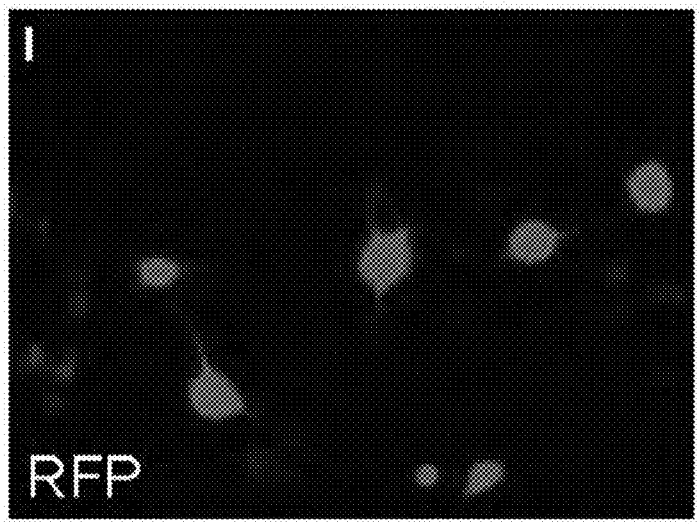
FIGS. 9L-9T show that miR124-RFP/Brn2 cells, which express RFP, also expressed various other neuronal markers after 6 days of STRC2 treatment, including Tuj1 (FIG. 9M-9N), NeuN (FIG. 9P-9Q), and Synapsin I (FIG. 9S-9T). Bar, 50 µm.
Figure 9M:
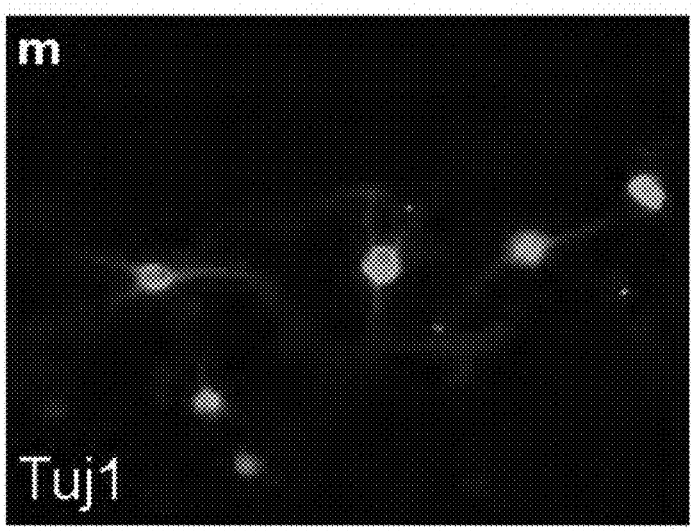
Figure 9N:
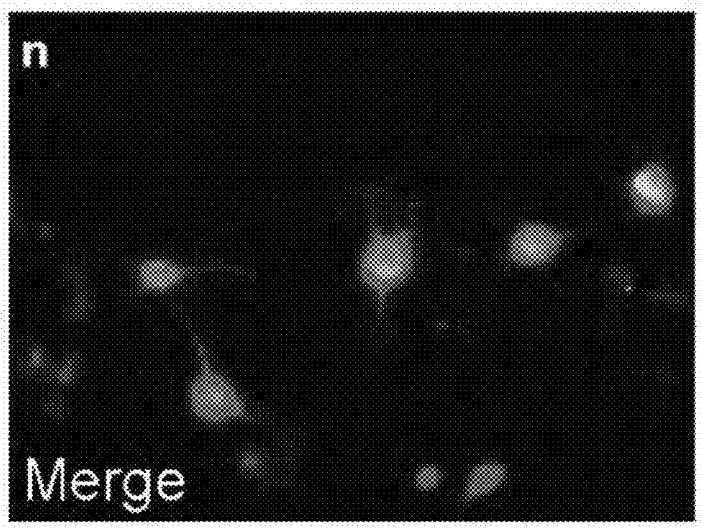
Figure 9O:
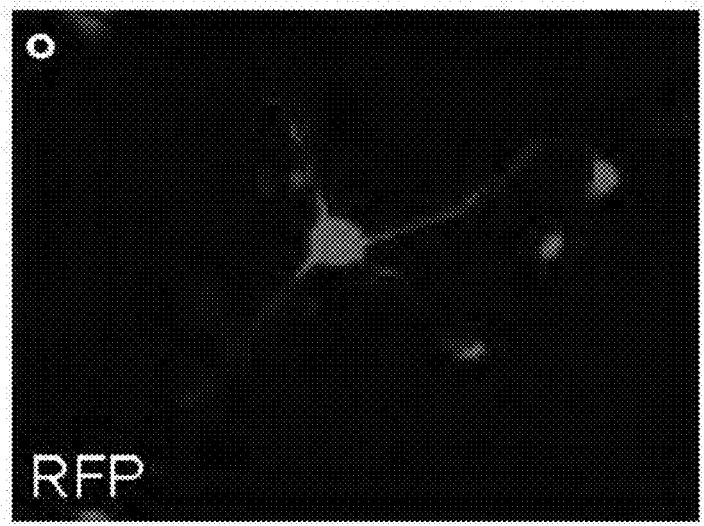
Figure 9P:
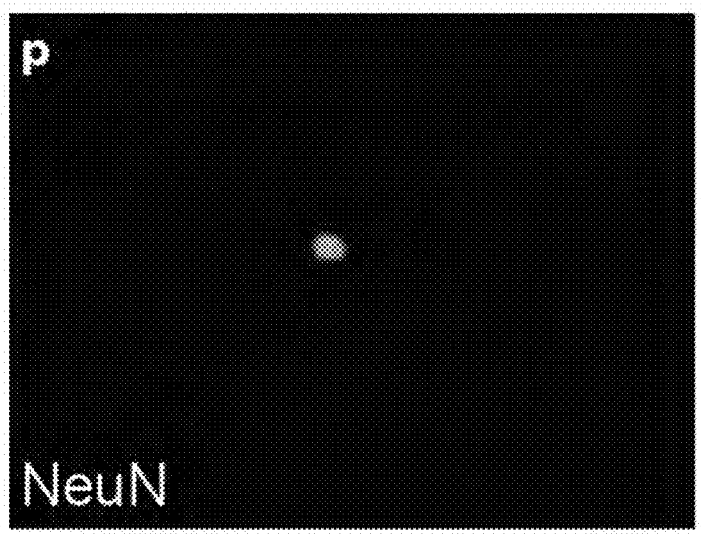
Figure 9Q:
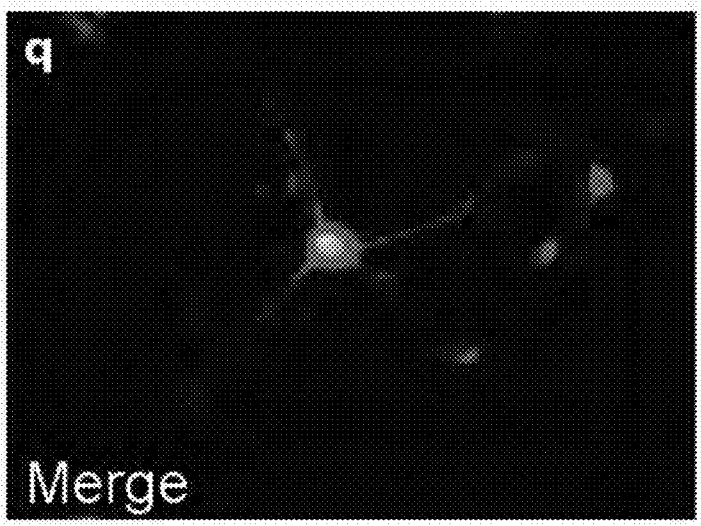
Figure 9R:
Figure 9S:
Figure 9T:
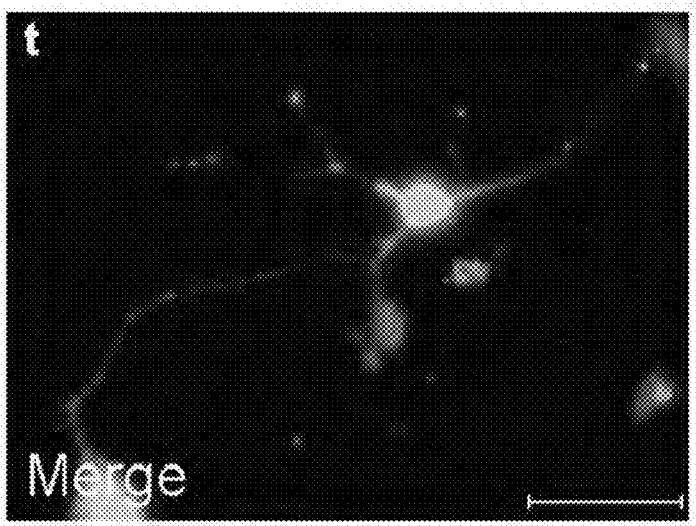
Figure 10A:
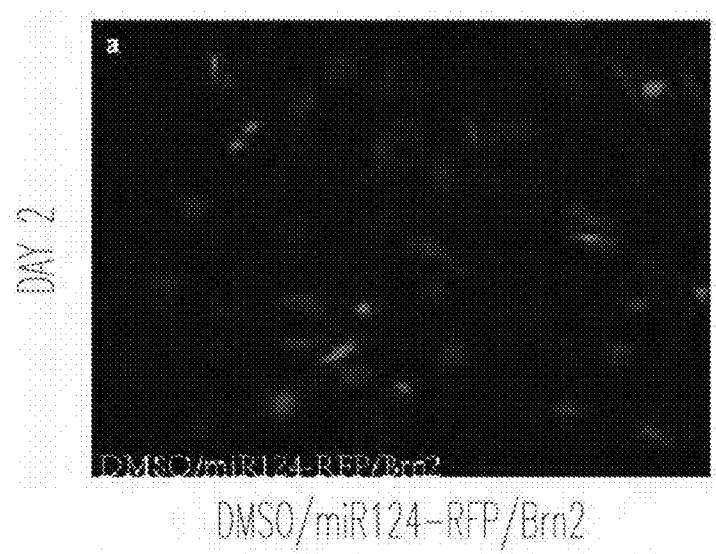
FIG. 10A-10F illustrate that SB431542 and CHIR99021 (the SC condition) is not as effective as the STRC2 condition after two days for converting miR124-RFP/Brn2 human fibroblasts to neuron-like cells.
Figure 10B:
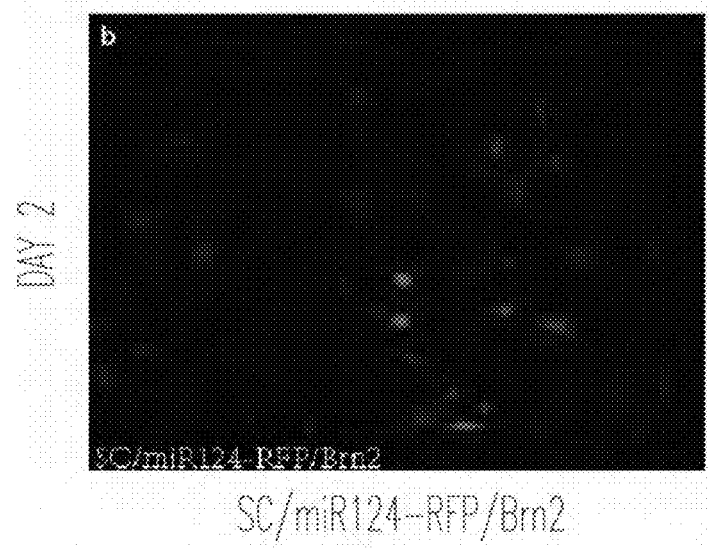
Figure 10C:
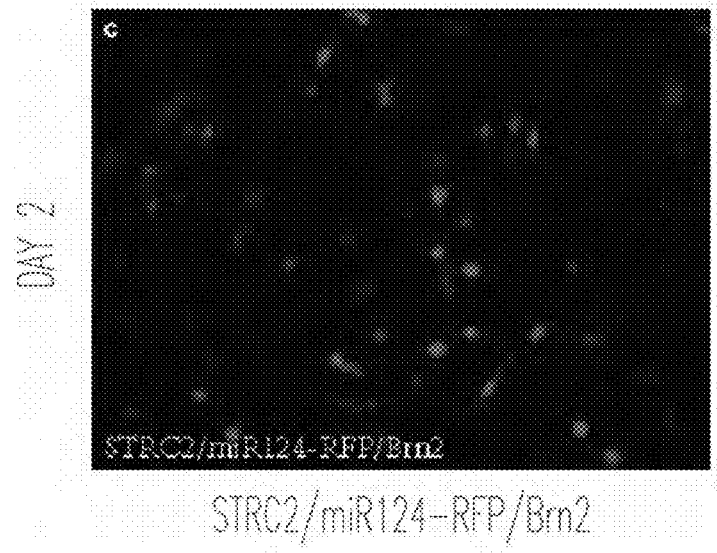
Figure 10D:
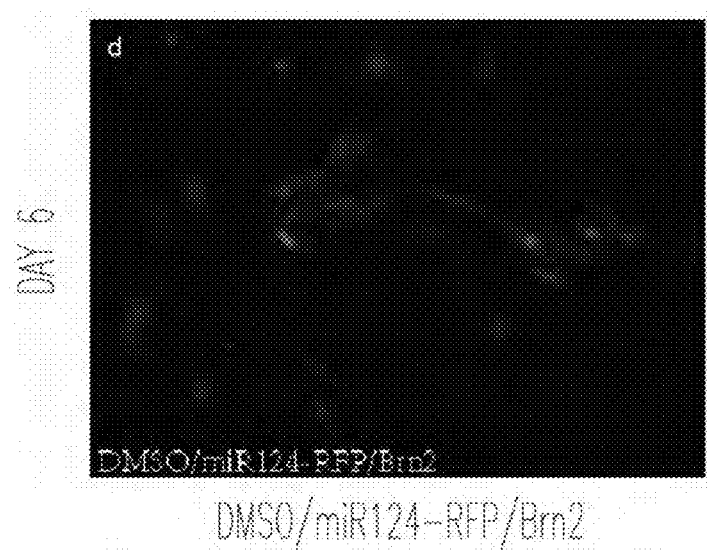
Figure 10E:
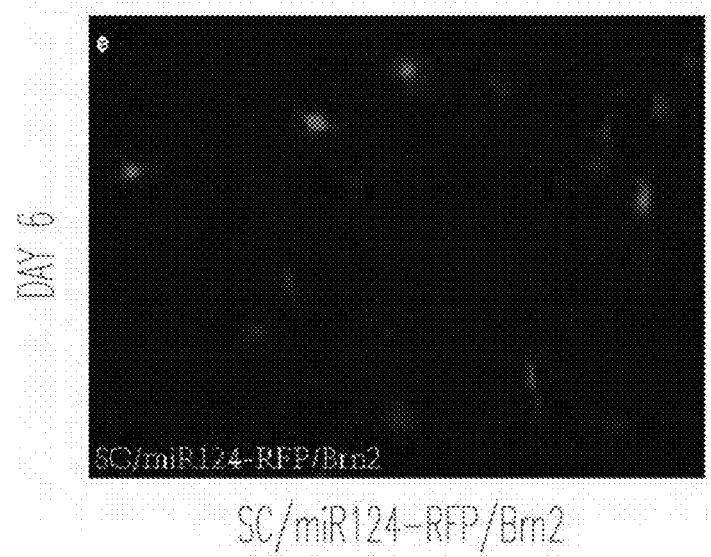
Figure 10F:
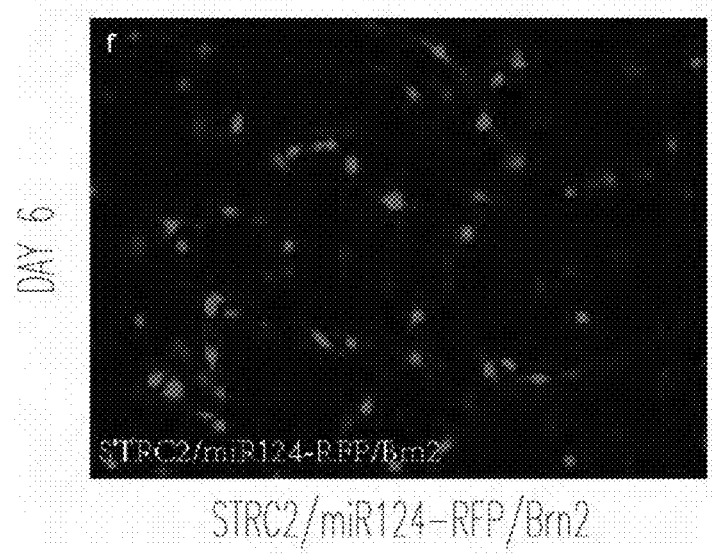

About 0.6% STRC2-Ascl1 cells were Tau-EGFP positive and exhibited characteristic neuronal morphology and expressed MAP2 in 10 days after induction, whereas again Ascl1 cells treated with DMSO did neither express Tau- EGFP nor exhibit typical neuronal morphology (FIG. 7A-79, 8A-8B). When induction was extended for total 18 days, induced neurons under the STRC2-Ascl1 condition exhibited fully mature neuronal phenotype with more elaborate neuronal branching, expression of vGlut1 and Synapsin I (FIG. 7D-7E). Consistently, STRC2-Ascl1 cells exhibited trains of action potentials upon injection of depolarizing current steps 18 days after reprogramming treatment (FIG. 7F-7G). In addition, these cells showed fast-inactivating sodium current and outward potassium current under voltage clamp (FIG. 7H). Most strikingly, up to 10% of STRC2-Ascl1 cells displayed sEPSCs on day 12 and more than 30% of STRC2-Ascl1 cells displayed sEPSCs on day 18 (FIG. 7J). In contrast such maturity was never seen in Ascl1 reprogrammed cells even after 18 days of induction (FIG. 7I-2J). Collectively, those results confirmed that STRC2 can fully substitute for Brn2/Mytl1 and enable reprogramming of fibroblast cells into functional mature neurons by a single factor, Ascl1.

In contrast to the mouse system, reprogramming human fibroblasts into mature neurons takes much longer time. In previous studies, about 35 days would be required to generate fully mature neurons from human neonatal fibroblasts using the factors Brn2/Ascl1/Myt1l/NeuroD2 (Pang et al., Nature 476, 220-223 (2011). About 25 days would be required to generate fully mature neurons from human neonatal fibroblasts using miR124-RFP/Brn2/Mytl1 (Ambasudhan et al., Cell Stem Cell 9, 113-118 (2011), and about 42 days are needed with the reported cocktail of three small molecules (CHIR99021, SB431542, and LDN193189) in the presence of Ascl1/Ngn2 (Ladewig et al., Nature Methods 575-578 (2012)).

Human foreskin fibroblasts (hFFs) transformed with inducible expression cassettes that encoded various transcription factors were used to ascertain whether neuronal reprogramming would occur and/or would be accelerated when mixed with the STRC2 cocktail. In addition to modification to express one or both of the Brn2 and Mytl1 transcription factors, some of the human fibroblasts were modified to express (upon induction) miR124, which is the most abundant microRNA in the mammalian central nervous system, and which modulates the activity of major anti-neuronal differentiation factors.

Remarkably, cells exhibiting characteristic neuronal morphology began to appear as early as two days after miR124-RFP/Brn2/Mytl1 or even miR124-RFP/Brn2 induction with STRC2 treatment (FIG. 9A-F). It is worth noting that as previously reported, combination of only miRNA and one transcription factor (i.e., miR124/Brn2) does not generate any neurons from human fibroblasts. Therefore, incubation with the STRC2 cocktail enabled neuronal reprogramming of human fibroblasts transduced with miR124/Brn2. In addition, neuronal reprogramming in miR124-RFP/Brn2 cells was not observed after treatment with SB431542 and CHIR99021 (SC condition) (FIG. 10), suggesting that the addition of TSA, CTPB, and Rolipram to the SC cocktail facilitates neuronal reprogramming of miR124-RFP/Brn2 cells.

Figure 12A:
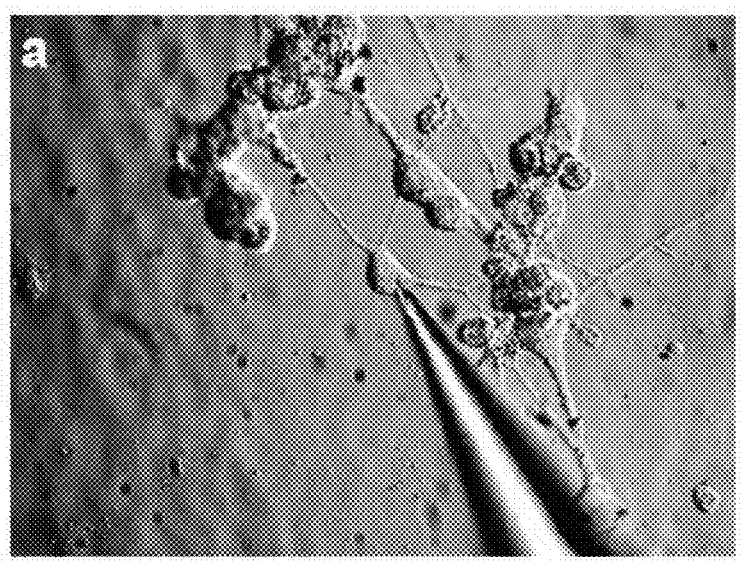
FIG. 12A-12P demonstrate that STRC2-treated miR124-RFP/Brn2 cells exhibited characteristics of mature neurons.
Figure 12B:
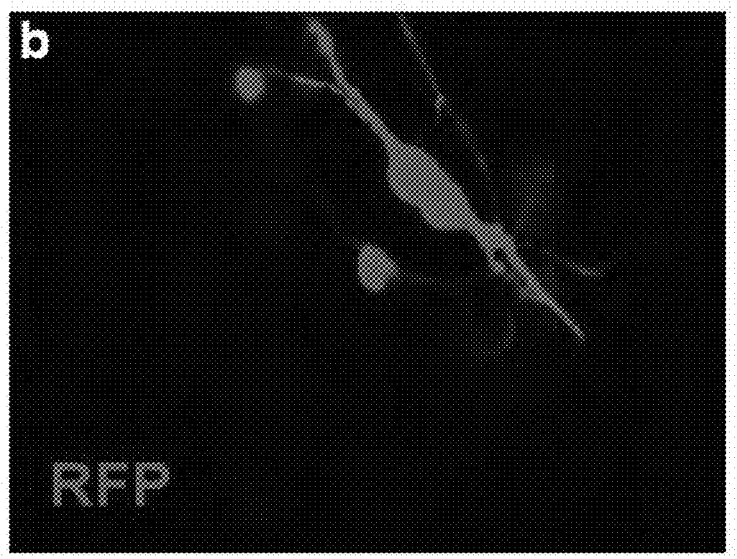
FIG. 12B shows that the cell shown in FIG. 12A expresses red fluorescent protein, indicating that the cell expresses microRNA124.
Figure 12C:
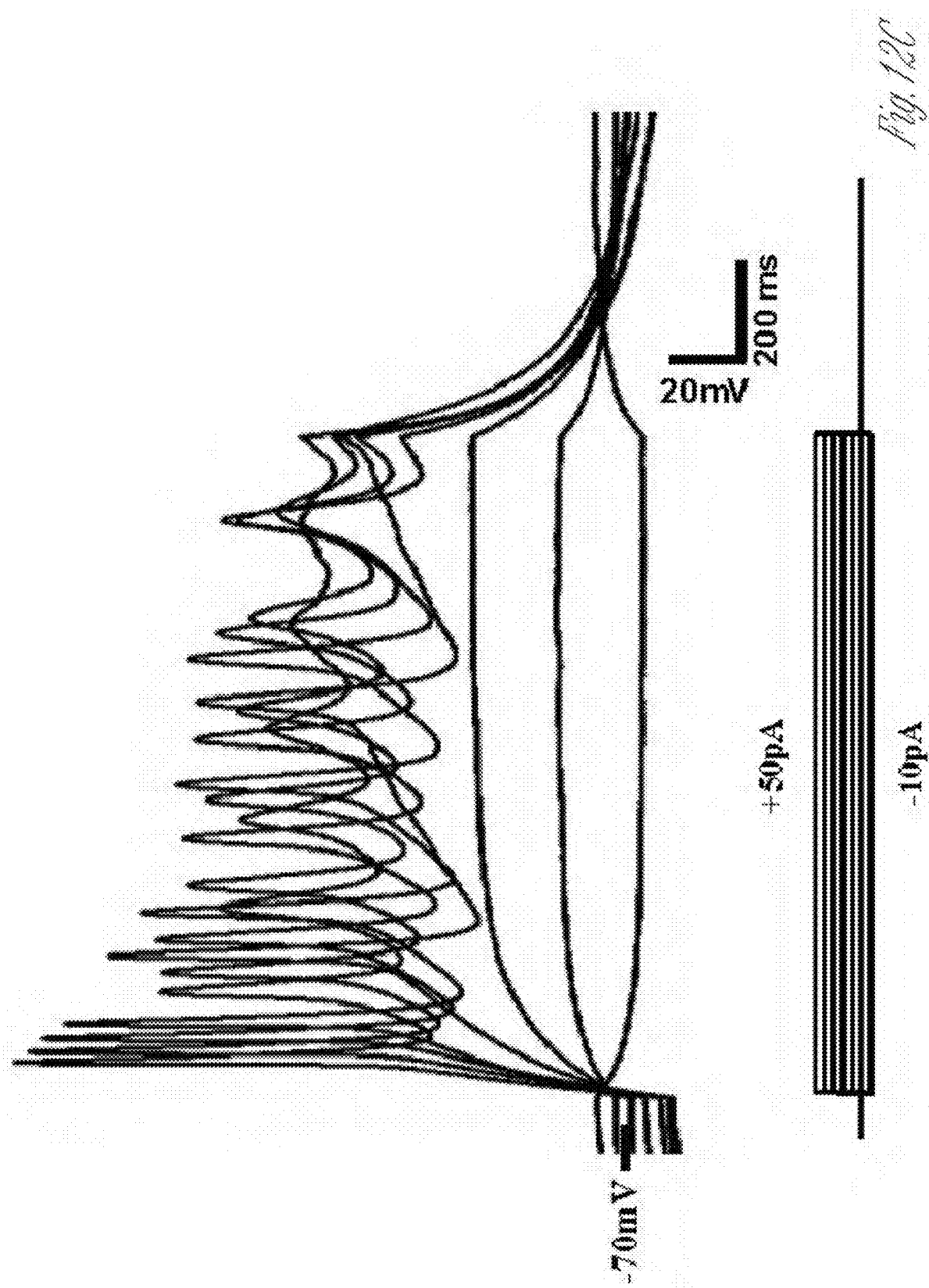
FIG. 12C-12D shows action potential trains exhibited by the RFP-positive miR124-RFP/Brn2 cell shown in FIG. 12A after treatment with STRC2 for 6 days, as recorded by patch clamp. Action Potential trains were recorded after current application (+80 pA) and were abolished by application of 1 µM tetrodotoxin (TTX).
Figure 12D:
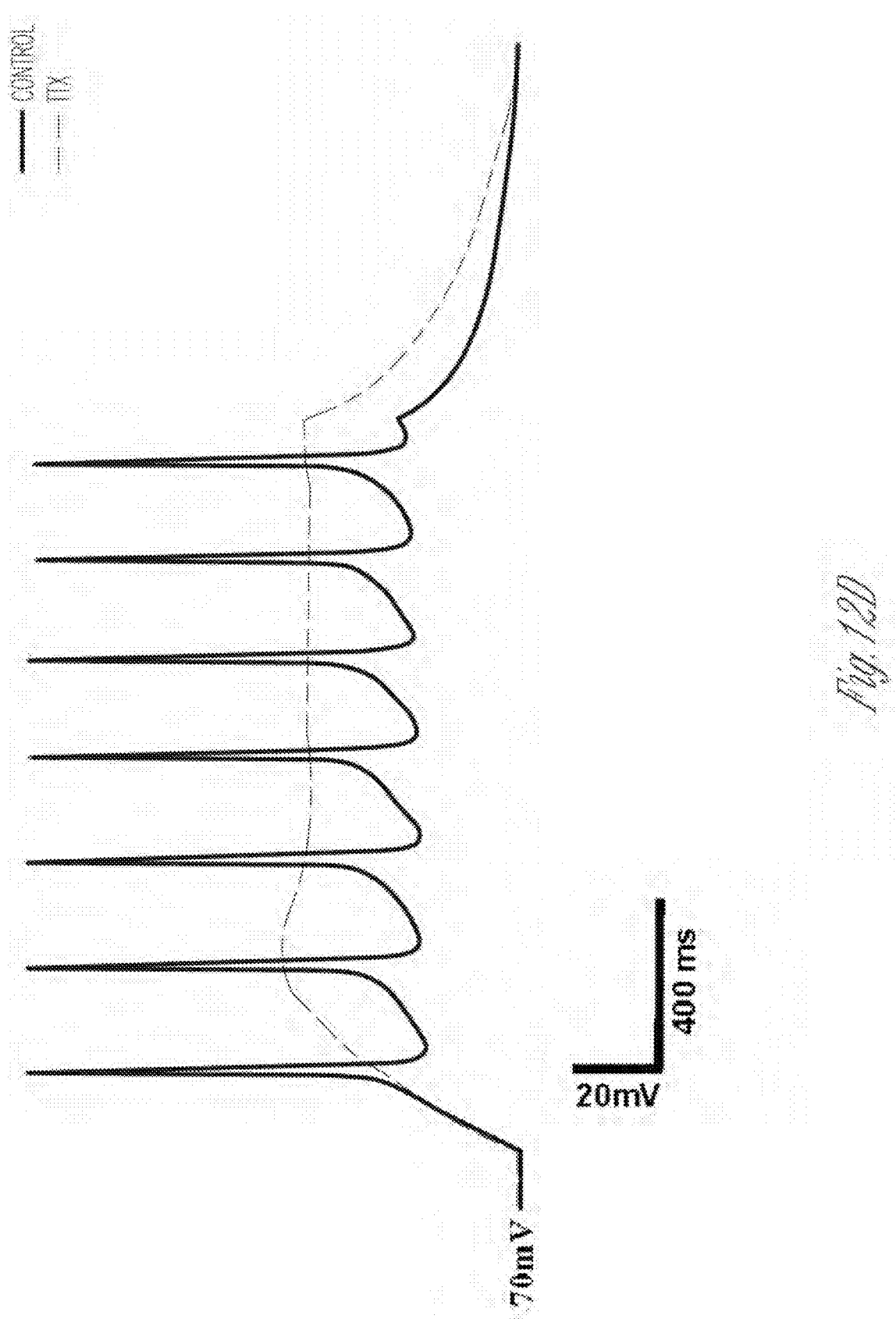
Figure 12E:
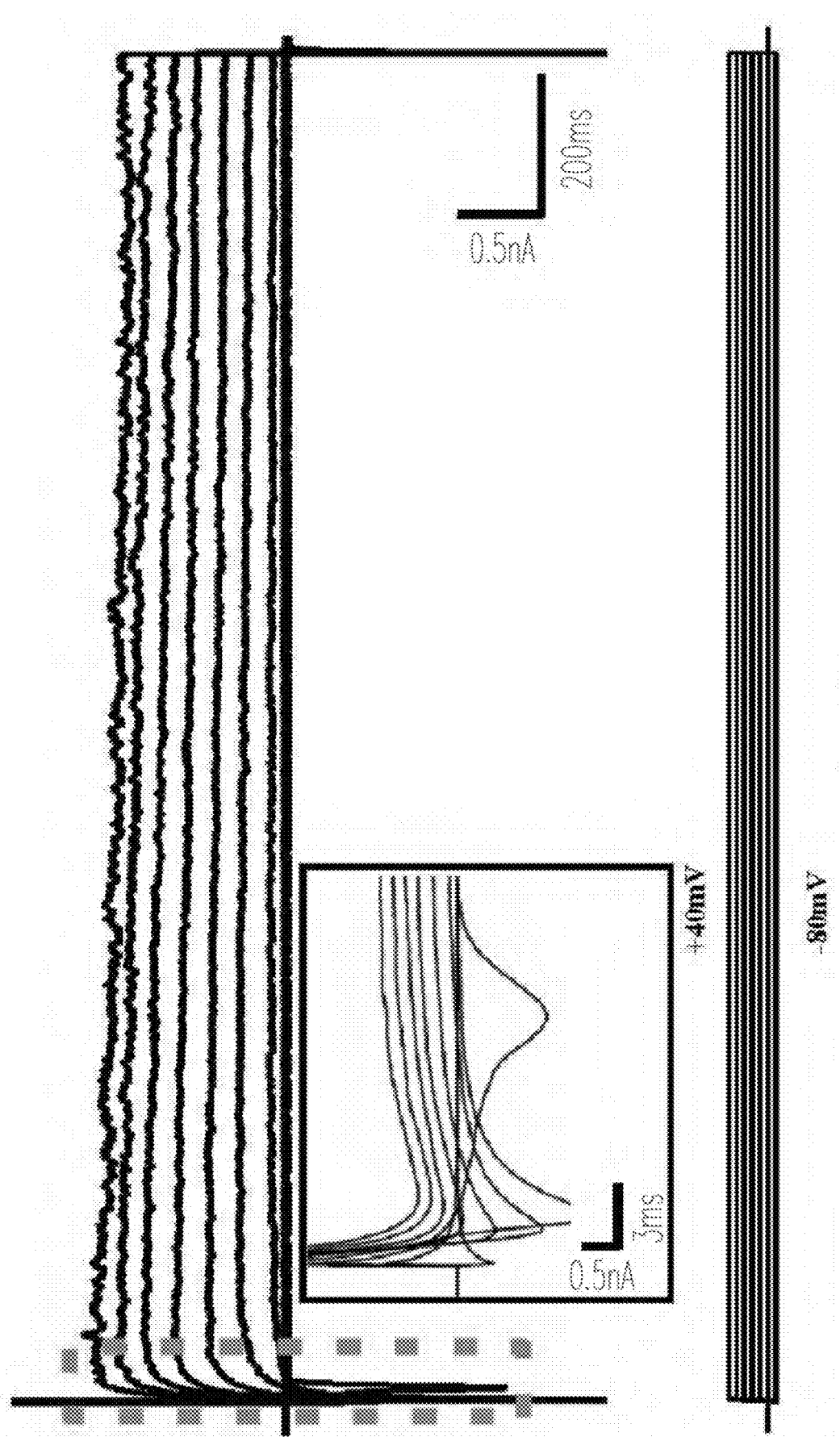
FIG. 12E illustrates that the recorded cells exhibited typical action current and slow-onset potassium current after a step-wise increase of depolarization.
Figure 12F:
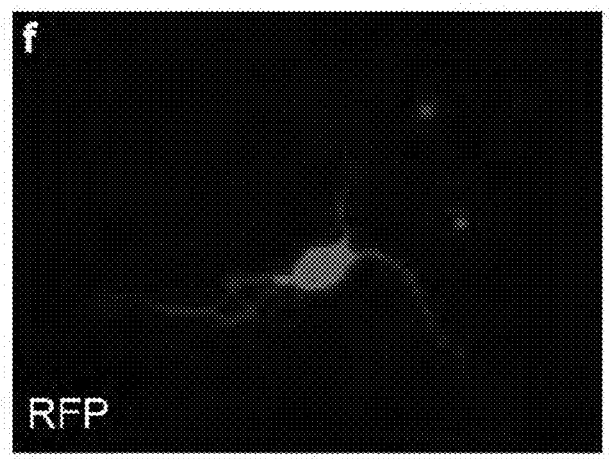
FIG. 12F-12K show that STRC2-treated miR124-RFP/Brn2 cells expressed markers for glutamatergic subtype neurons vGlut1, GlutR2, and GlutR3 after 12 days of induction. Bar, 50 µm.
Figure 12G:
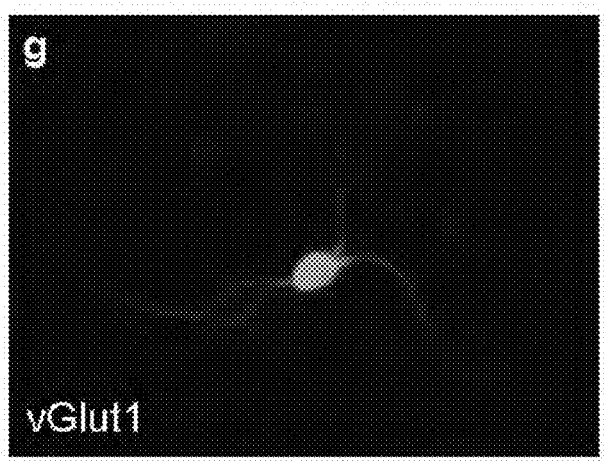
Figure 12H:
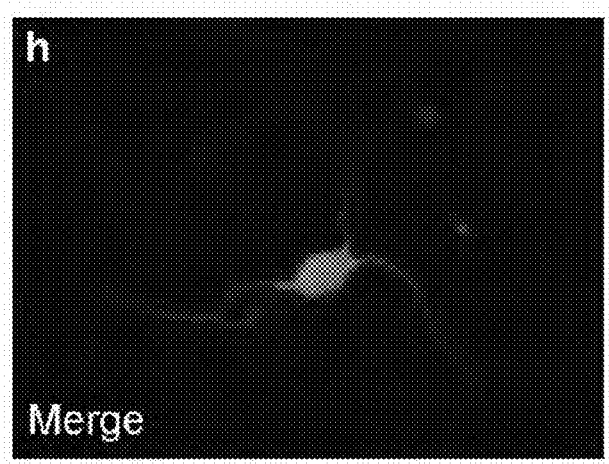
Figure 12I:
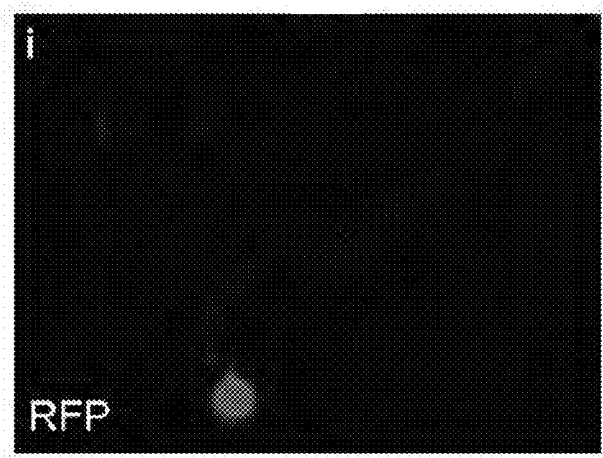
Figure 12J:
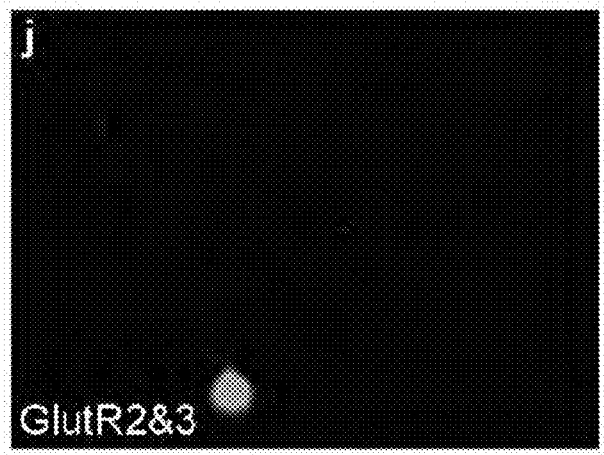
Figure 12K:
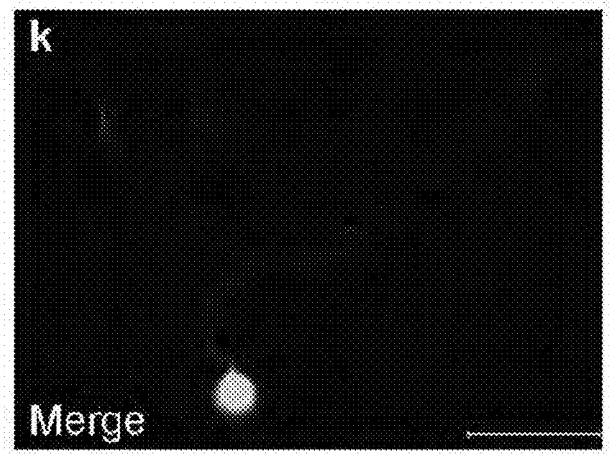
Figure 12L:
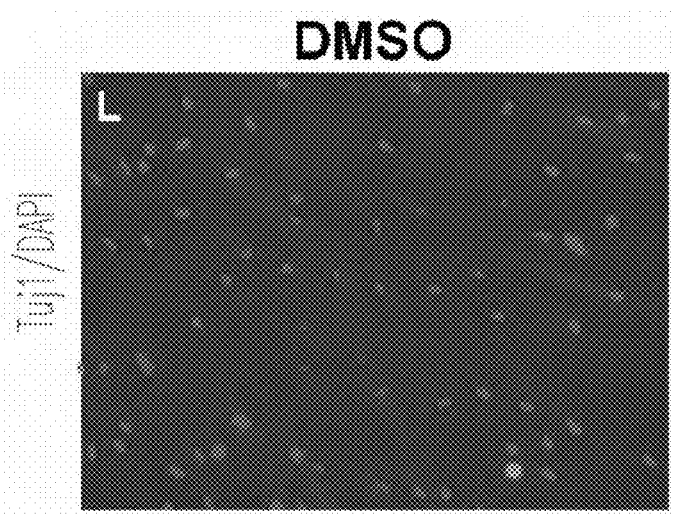
Figure 12M:
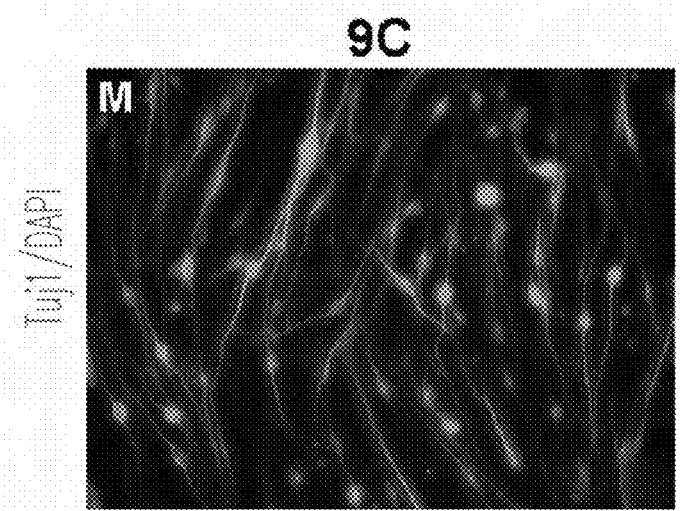
Figure 12N:
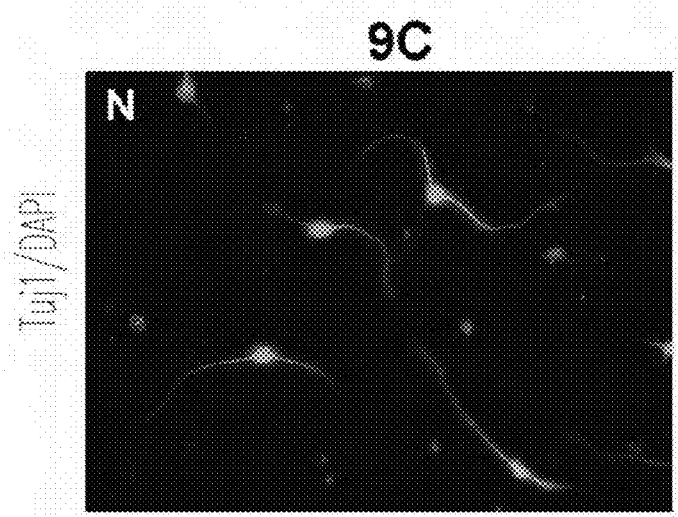
Figure 12O:
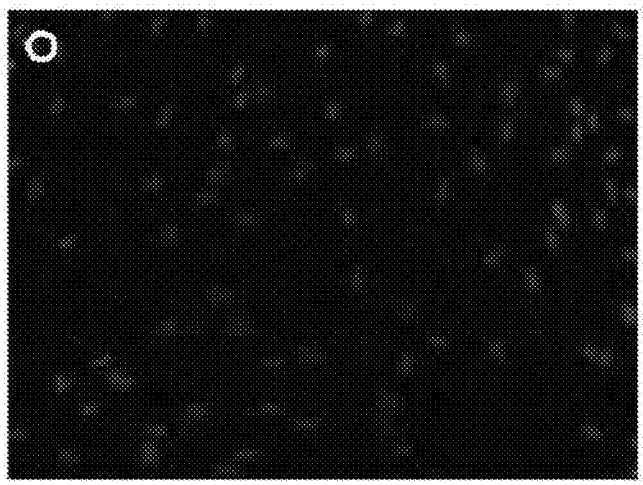
Figure 12P:
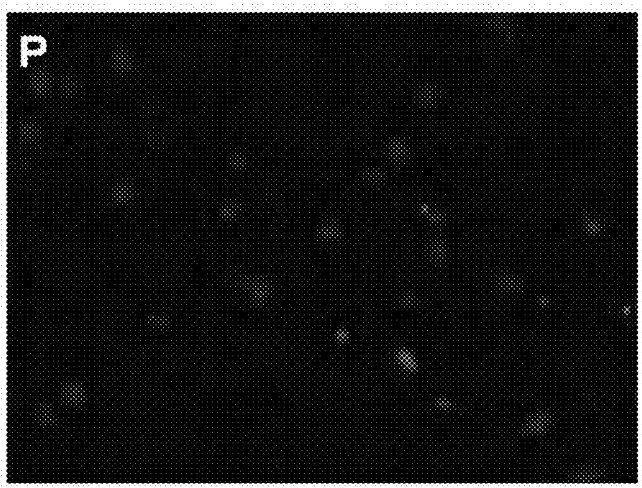

A time-lapse experiment showed that the most drastic period of neuronal conversion for a large percentage of miR124-RFP/Brn2-STRC2 treated cells occurred over the 35 hours, from about 65 hours to 100 hours (FIG. 11A-11D). In contrast, in the control conditions without STRC2 treatment, MAP2 positive neuronal cells did not appear until day 25 in miR124-RFP/Brn2/Mytl1-induced culture and never showed up at all in miR124-RFP/Brn2-induced culture. After 6 days of STRC2 treatment, more than 30% RFP positive cells (miR124-RFP/Brn2 cells) were converted to MAP2 positive cells with characteristic neuronal morphology, whereas DMSO-treated miR124-RFP/Brn2 cells neither expressed MAP2 nor exhibited neuronal morphology (FIG. 9G-9K). In addition, these STRC2/miR124/Brn2 induced neurons displayed a mature neuron phenotype, expressing other typical neuronal markers, including βIII-tubulin, NeuN, and Synapsin I (FIG. 9I-9T). To further characterize the induced neurons, RFP positive cells were recorded on Day 6 after treatment using a patch clamp (FIG. 12A-12B). Trains of action potentials (FIG. 12C), which could be abolished by the addition of 1 µM TTX (FIG. 12D), and fast inactivating sodium current (FIG. 4E) were readily recorded from over 70% of recorded cells (Table 1). Furthermore, ICC analysis detected glutamatergic neuronal subtype in STRC2/miR124-RFP/Brn2 condition 12 days after induction, including vGlut1 and GlutR2&3, which suggested that these cells were mature glutamatergic neurons (FIG. 12F-4K).

To investigate whether small molecules can convert human fibroblasts to functional neuronal cells in absence of transcription factors or microRNAs, the STRC2 conditions were further optimized for human neonatal fibroblasts (hF2097 cells) and a new chemical condition (9C) was developed, which included nine compounds: CHIR99021 (GSK3 inhibitor), SB431542 (ALK4/5/7 inhibitor), MS275 (HDAC1 inhibitor), CTB (p300 activator), Rolipram (PDE4 inhibitor), Forskolin (Adenylyl cyclase agonist), CD1530 (RARγ receptor agonist), TDMB (Tropanyl-3,5-dimethyl-benzoate, 5-HT3 antagonist), and ACPD (mGlu receptor agonist).

As shown in FIGS. 12L-12P, compared with DMSO treatment, the 9C condition can efficiently induce over 80% human fibroblasts into Tuj1-positive cells by day 20. Importantly, most of these Tuj1-positive cells exhibit typical neuronal morphology and some of them also expressed NeuN, a more mature neuronal marker, indicating that the 9C cocktail can convert non-neuronal cells into neurons.

EXAMPLE 3

Conversion of Fetal Lung Fibroblasts into Neuronal Cells

This Example shows that other types of cells can be converted to neuronal cells using the 9C cocktail.
Methods
Another type of human fibroblasts, fetal lung fibroblasts (CCL-171 cells), were tested to determine whether the 9C composition could convert these cells to neuronal cells. The 9C composition contained CHIR99021 (GSK3 inhibitor), SB431542 (ALK4/5/7 inhibitor), MS275 (HDAC1 inhibitor), CTB (p300 activator), Rolipram (PDE4 inhibitor), Forskolin (Adenylyl cyclase agonist), CD1530 (RARγ receptor agonist), TDMB (Tropanyl-3,5-dimethylbenzoate, 5-HT3 antagonist), and ACPD (mGlu receptor agonist).

Figure 13F:
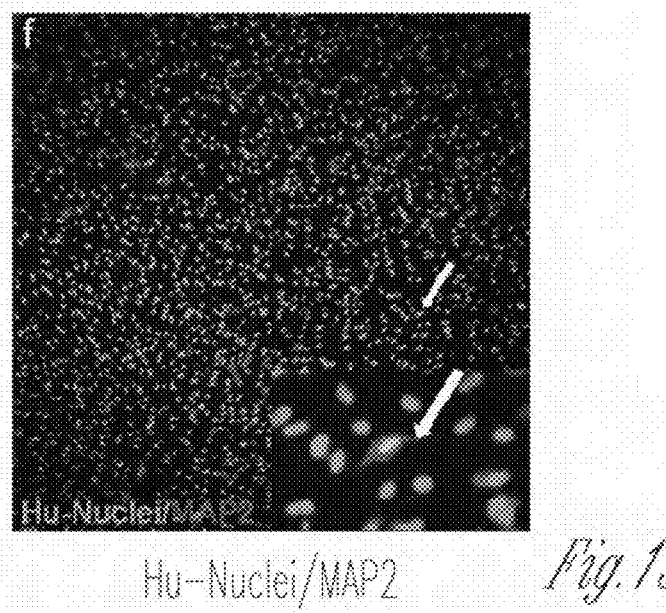
Figure 13G:
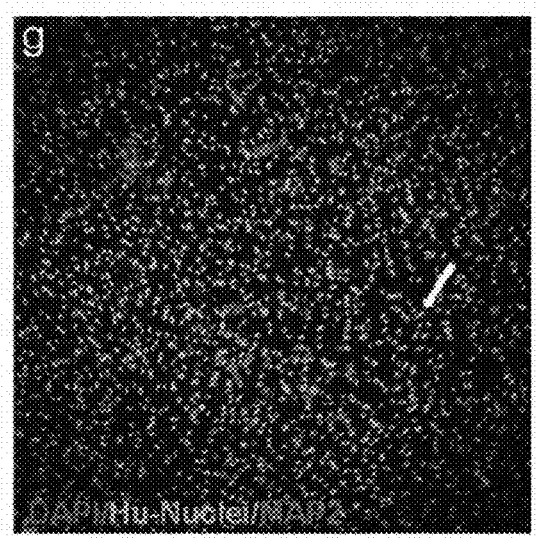

CCL171 fibroblasts were treated with the 9C composition as described in Example 2 for 3 days and then stained with an antibody against beta-Tubulin III. In a second experiment, the CCL-171 fibroblasts were treated with the 9C composition for 24 hours and then co-cultured with rat neurons for another 5 days. The cells were fixed and analyzed by immunocytochemistry.
Results
The CCL171 cells were very sensitive to the 9C composition. Within only 3 days of incubation in the 9C composition, CCL171 cells were induced to become Tuj1-positive neuron-like cells (FIG. 13A). However, such fast conversion caused stress in the CCL171 cells and unfortunately most of them were not able to survive to become mature neurons.

To protect the 9C induced-neurons, the CCL171 cells were incubated in the 9C composition for a shorter time period (i.e. 24 hours), followed by co-culture with rat neurons for 5 days. In order to distinguish the induced neurons from the rat neurons, the co-cultured cells were stained by using the antibodies against human nuclei and MAP2. As shown in FIG. 13C-G, the 9C-CCL cells were clearly converted into mature neurons (FIG. 13C-G).

EXAMPLE 4 microRNA124 Enhances Conversion of Fibroblasts into Neurons

Figure 14A:
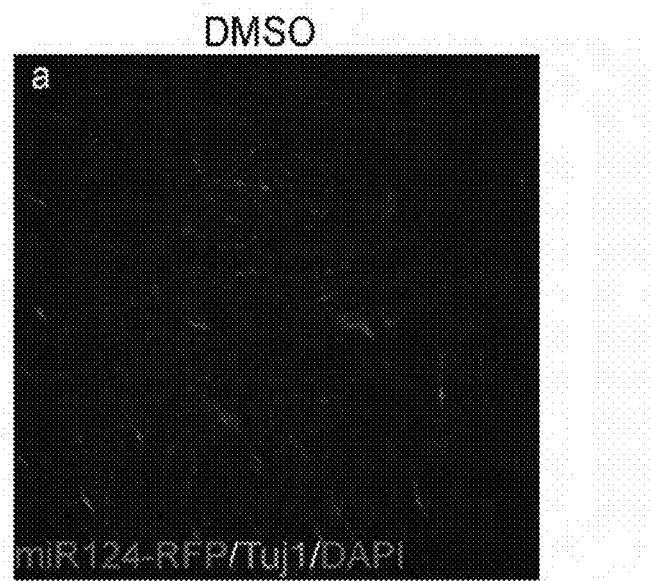
FIG. 14A-14B shows that neuronal conversion in the presence of the 9C composition is enhanced by miR124. The miR124-RFP vector was introduced into hF2097 cells and the cells were treated with DMSO (FIG. 14A) or with the 9C composition (FIG. 14B) for 10 days. Then the cells were fixed and analyzed by immunocytochemistry using an anti-beta-Tubulin III antibody. The arrows point to the neuron-like cells.
Figure 14B:
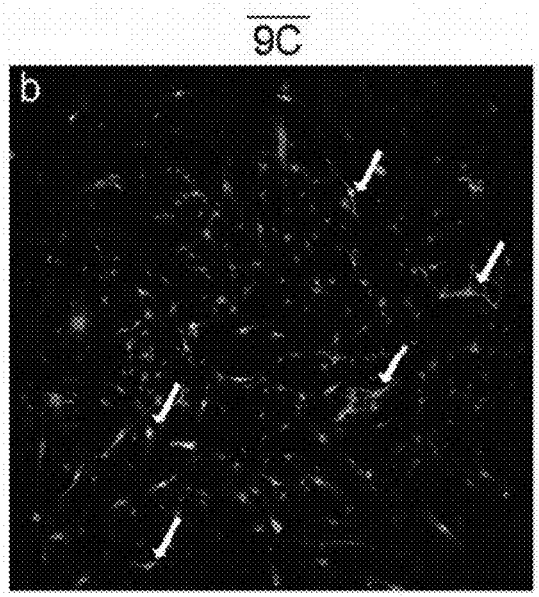

Although miR124 is thought to play a role in the neuronal programming, no evidence suggests that miRNA124 alone is able to convert fibroblasts into neurons.
Methods A miR124-RFP vector was introduced into hF2097 cells and the cells were either incubated with the 9C factors or with DMSO (control) for 10 days. The cells were then fixed and analyzed by ICC using the antibody recognized beta-Tubulin III (Tuj1) as a marker of the neuronal phenotype.
Results As shown in FIG. 14A, human hF2097 fibroblast cells that express miR124 without supplemental factors and without expression of other microRNAs, did not convert the foreskin fibroblasts into neurons. However, as shown in FIG. 14B, human hF2097 fibroblast cells that express miR124 and were incubated in media with the 9C factors, generate more neuron-like cells within 10 days after 9C treatment than when control human hF2097 fibroblast without miR124 expression.

Accordingly, expression of miR124 enhances conversion of cells to the neuronal phenotype when the 9C factors are present in the cell media.

REFERENCES

1 Takahashi, K. & Yamanaka S. Induction of pluripotent stem cells from mouse embryonic and adult fibroblast cultures by defined factors. *Cell* 126, 663-676, doi:S0092-8674(06)00976-7 [pii]10.1016/j.cell.2006.07.024 (2006).
2 Takahashi, K. et al. Induction of pluripotent stem cells from adult human fibroblasts by defined factors. *Cell* 131, 861-872, doi:S0092-8674(07)01471-7 [pii]10.1016/j.cell.2007.11.019 (2007).
3 Yu, J. et al. Induced pluripotent stem cell lines derived from human somatic cells. *Science* 318, 1917-1920, doi: 1151526[pii]10.1126/science.1151526 (2007).
4 Ieda, M. et al. Direct reprogramming of fibroblasts into functional cardiomvocytes by defined factors. *Cell* 142, 375-386, doi:10.1016/j.cell.2010.07.002S0092-8674(10)00771-3[pii] (2010).
5 Sekiya, S. & Suzuki, A. Direct conversion of mouse fibroblasts to hepatocyte-like cells by defined factors. *Nature* 475, 390-393, doi:10.1038/nature10263nature10263[pii] (2011).
6 Huang, P. et al. Induction of functional hepatocyte-like cells from mouse fibroblasts by defined factors. *Nature* 475, 386-389, doi:10.1038/nature10263nature10116[pii] (2011).
7 Pang, Z. P. et al. Induction of human neuronal cells by defined transcription factors. *Nature* 476, 220-223, doi: 10.1038/nature10202nature10202[pii] (2011).
8 Ambasudhan, R. et al. Direct reprogramming of adult human fibroblasts to functional neurons under defined conditions. *Cell Stem Cell* 9, 113-118, doi:S1934-5909 (11)00332-8[pii]10.1016/j.stem.2011.07.002 (2011).
9 Vierbuchen, T. et al. Direct conversion of fibroblasts to functional neurons by defined factors. *Nature* 463, 1035-1041, doi:nature08797[pii]10.1038/nature08797 (2010).
10 Ring, K. L. et al. Direct reprogramming of mouse and human fibroblasts into multipotent neural stem cells with a single factor. *Cell Stem Cell* 11, 100-109, doi:S1934-5909(12)00289-5[pii]10.1016/j.stem.2012.05.018 (2012).
11 Lujan, E., Chanda, S., Ahlenius, H., Sudhof, T. C. & Wernig, M. Direct conversion of mouse fibroblasts to self-renewing, tripotent neural precursor cells. *Proc Natl Acad Sci USA* 109, 2527-2532, doi:1121003109[pii] 10.1073/pnas.1121003109 (2012).
12 Son, E. Y. et al. Conversion of mouse and human fibroblasts into functional spinal motor neurons. *Cell Stem Cell* 9, 205-218, doi:S1934-5909(11)00377-8 [pii] 10.1016/j.stem.stem.2011.07.014 (2011).
13 Qiang, L. et al. Directed conversion of Alzheimer's disease patient skin fibroblasts into functional neurons. *Cell* 146, 359-371, doi:S0092-8674(11)00764-1 [pii]10.1016/j.cell.2011.07.007 (2011).
14 Pfisterer, U. et al. Direct conversion of human fibroblasts to dopaminergic neurons. *Proc Natl Acad Sci USA* 108, 10343-10348, doi:1105135108 [pii]10.1073/pnas.1105135108 (2011).
15.. Caiazzo, M. et al. Direct generation of functional dopaminergic neurons from mouse and human fibroblasts. *Nature* 476, 224-227, doi:10.1038/nature10284nature10284[pii] (2011).
16. Li, W. et al. Rapid induction and long-term self-renewal of primitive neural precursors from human embryonic stem cells by small molecule inhibitors. *Proc Natl Acad Sci U S A* 108, 8299-8304, doi:10.1073/pnas.10140411081014041108[pii] (2011).
17. Li, W. et al. Generation of rat and human induced pluripotent stem cells by combining genetic reprogramming and chemical inhibitors. *Cell Stem Cell* 4, 16-19, doi:10.1016/j.stem.2008.11.014S1934-5909(08)00616-4 [pii] (2009).
18. Ladewig, J. et al. Small molecules enable highly efficient neuronal conversion of human fibroblasts. *Nat Methods,* doi:10.1038/nmeth.1972nmeth.1972[pii] (2012).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound," "a cell," "a nucleic acid" or "a polypeptide" includes a plurality of such compounds, cells, nucleic acids or polypeptides (for example, a solution of cells, nucleic acids or polypeptides, a suspension of cells, or a series of compound, cell, nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following statements are intended to describe and summarize various embodiments of the invention according to the foregoing description in the specification.

STATEMENTS

1. A composition comprising one or more of the following agents: a GSK3 inhibitor, a WNT agonist, an ALK4/5/7 inhibitor, an HDAC inhibitor, a p300 activator, a PDE4 inhibitor, an Adenylyl cyclase agonist, a retinoic acid receptor γ agonist, a 5-HT3 antagonist, or a metabotropic glutamate (mGlu) receptor agonist.
2. The composition of statement 1, containing at least two of the agents, or at least three of the agents, or at least four of the agents, or at least five of the agents, or at least six of the agents, or at least seven of the agents, or at least eight of the agents.
3. The composition of statement 1 or 2, further comprising one or more of the following compounds: a ROCK inhibitor, a neuronal differentiation enhancer, an omega-3 fatty acid, an A3 adenosine receptor agonist or an L-type calcium channel blocker.
4. The composition of any of statements 1-3, wherein the WNT agonist is an agent that activates TCF/LEF-mediated transcription in a cell.
5. The composition of any of statements 1-4, wherein the WNT agonist binds and activates a Frizzled receptor family member.
6. The composition of any of statements 1-5, wherein the WNT agonist is a WNT family protein, an inhibitor of intracellular beta-catenin degradation, an activator of TCF/LEF, an inhibitor of GSK-3, or a combination thereof.
7. The composition of any of statements 1-6, wherein the WNT agonist is selected from the group consisting of WNT-3a, a GSK-inhibitor, WNT5, WNT-6a, Norrin, and another WNT family protein.
8. The composition of any of statements 1-7, wherein the GSK3 inhibitor is selected from a group consisting of CHIR99021 (6-(2-(4-(2,4-dichlorophenyl)-5-(4-methyl-1H-imidazol-2-yl)pyrimidin-2-ylamino)ethylamino)nicotinonitrile); 1-azakenpaullone (9-Bromo-7,12-dihydro-pyrido[3',2':2,3]azepino[4,5-]indol-6(5H)-one), BIO ((2'Z,3'E)-6-Bromoindirubin-3'-oxime); AR-A014418 (N-(4-Methoxybenzyl)-N'-(5-nitro-1,3-thiazol-2-yl)urea); Indirubin-3'-monoxime; 5-Iodo-indirubin-3'-monoxime; kenpaullone (9-Bromo-7,12-dihydroindolo-[3,2-d][1]benzazepin-6(5H)-one); SB-415286 (3-[(3-Chloro-4-hydroxyphenyl)amino]-4-(2-nitro-phenyl)-1H-pyrrole-2,5-dione); SB-216763 (3-(2,4-Dichlorophenyl)-4-(1-methyl-1H-indol-3-yl)-1H-pyrrole-2,5-dione); Maybridge SEW00923SC (2-anilino-5-phenyl-1,3,4-oxadiazole); (Z)-5-(2,3-Methylenedioxyphenyl)-imidazolidine-2,4-dione; TWS119 (3-(6-(3-aminophenyl)-7H-pyrrolo[2,3-d]pyrimidin-4-yloxy)phenol); CHIR98014 (N2-(2-(4-(2,4-dichlorophenyl)-5-(1H-imidazol-1-yl)pyrimidin-2-ylamnino)ethyl)-5-nitropyridine-2,6-diamine; SB415286 (3-(3-chloro-4-hydroxyphenylamino)-4-(2-nitrophenyl)-1H-pyrrole-2,5-dione); Tideglusib (2-(1-naphthalenyl)-4-(phenylmethyl)); LY2090314 (3-imidazo[1,2-a]pyridin-3-yl-4-[1,2,3,4-tetrahydro-2-(1-piperidinylcarbonyl)-pyrrolo[3,2,1-jk][1,4]benzodiazepin-7-yl]); lithium salt; and any combination thereof.
9. The composition of any of statements 1-8, wherein the GSK3 inhibitor is CHIR99021, SB216763, TWS119, CHIR98014, Tideglusib (NP031112, NP-12), SB415286, LY2090314, or any combination thereof.
10. The composition of any of statements 1-9, wherein the TGFβ inhibitor is selected from the group consisting of 4-[4-(1,3-benzodioxol-5-yl)-5-(2-pyridinyl)-1H-imidazol-2-yl]benzamide (SB 431542); 3-(6-Methyl-2-pyridinyl)-N-phenyl-4-(4-quinolinyl)-1H-pyrazole-1-carbothioamide (A83-01); 2-(3-(6-Methylpyridine-2-yl)-1H-pyrazol-4-yl)-1,5-naphthyridine (SJN 2511); 4-[4-(2,3-Dihydro-1,4-benzodioxin-6-yl)-5-(2-pyridinyl)-1H-imidazol-2-yl]benzamide (D4476); 4-[3-(2-Pyridinyl)-1H-pyrazol-4-yl]-quinoline (LY 364947); 2-(4-(benzo[d][1,3]dioxol-5-yl)-2-tert-butyl-1H-imidazol-5-yl)-6-methylpyridine (SB505124); 6-[2-(1,1-Dimethylethyl)-5-(6-methyl-2-pyridinyl)-1H-imidazol-4-yl]quinoxaline (SB 525334); 2-(5-Chloro-2-fluorophenyl)-4-[(4-pyridyl)amino]pteridine (SD 208); 4-(6-(4-(piperazin-1-yl)phenyl)pyrazolo[1,5-a]pyrimidin-3-yl)quinoline (LDN-193189 and any combination thereof.
11. The composition of any of statements 1-10, wherein the TGFβ inhibitor is SB-431542.
12. The composition of any of statements 1-11, wherein the HDAC inhibitor is an HDAC1 inhibitor.

13. The composition of any of statements 1-12, wherein the HDAC inhibitor is Suberoylanilide Hydroxamic Acid; BML-210 (N1-(2-aminophenyl)-N8-phenyl-octanediamide); Depudecin; HC Toxin ((6R,9S,14aR)-3,6R-dimethyl-9S-(7-((S)-oxiran-2-yl)-7-oxoheptyl) decahydropyrrolo[1,2-a][1,4,7,10]-tetraazacyclododecine-1,4,7,10- tetranone); Scriptaid (N-Hydroxy-1,3-dioxo-1H-benz[de]isoquinoline-2 (3H)-hexananmide); Phenylbutyrate; Sodium Butyrate; pivaloyloxymethyl butyrate; valproic Acid; Suramin; Trichostatin A; APHA Compound 8 (3-(1-Methyl-4-phenylacetyl-1H-2-pyrrolyl)-N-hydroxy-2-propenamide); Apicidin (Cyclo[(2S)-2-Amino-8-oxodecanoyl-1-methoxy-L-tryptophyl-L-isoleucyl-(2R)-2-piperidine-carbonyl]); Trapoxin B (3,6-dibenzyl-9-[6-(oxiran-2-yl)-6-oxohexyl]-1,4,7,10-tetrazabicyclo [10.3.0]pentadecane-2,5,8,11-tetrone); Chlamydocin ((3R)-3-benzyl-6,6-dimethyl-9-[6-[(2R)-oxiran-2-yl]-6-oxohexyl]-1,4,7,10-tetrazabicyclo[10.3.0]pentadecane-2,5,8,11-tetrone); Depsipeptide (1S,4S,7Z,10S,16E,21R)-7-ethylidene-4,21-di(propan-2-yl)-2-oxa-12,13-dithia-5,8,20,23-tetrazabicyclo[8.7.6]tricos-16-ene-3,6,9,19,22-pentone; C1-994; MS-27-275 (MS275); MGCD0103 (N-(2-aminophenyl)-4-[[(4-pyridin-3-ylpyrimidin-2-yl)amino]methyl]benzamide); NVP-LAQ-824 ((E)-N-hydroxy-3-[4-[[2-hydroxyethyl-[2-(1H-indol-3-yl)ethyl]amino]-methyl]phenyl]prop-2-enamide); CBHA (N-hydroxy-3-[(E)-3-(hydroxyamino)-3-oxoprop-1-enyl]benzamide); JNJ16241199 (N-hydroxy-2-(4-(naphthalen-2-ylsulfonyl)piperazin-1-yl)pyrimidine-5-carboxamide); Tubacin (N-[4-[(2R,4R,6S)-4-[(4,5-diphenyl-1,3-oxazol-2-yl)sulfanylmethyl]-6-[4-(hydroxymethyl)phenyl]-1,3-dioxan-2-yl]phenyl]-N'-hydroxyoctanediamide); A-161906 (7-[4-(4-cyanophenyl)phenoxy]-heptanohydroxamic acid); Proxamide; Oxamflatin ((E)-5-[3-(benzenesulfonamido)phenyl]-N-hydroxypent-2-en-4-ynamide); 3C1-UCHA (6-(3-chlorophenylureido) caproic hydroxamic acid); AOE (2-amino-8-oxo-9,10-epoxydecanoic acid); CHAP31 ((2S)-N'-hydroxy-N-[(2R)-3-(4-methoxyphenyl)-1-[[(2S,3R)-3-methyl-1-oxopentan-2-yl]amino]-1-oxopropan-2-yl]-2-(pyrrolidine-2-carbonylamino)octanediamide); or any combination thereof.

14. The composition of any of statements 1-13, wherein the HDAC inhibitor is selected from the group consisting of C1994 (Tacedinaline), ITF2357 (Givinostat), PI3K/HDAC Inhibitor I, Vorinostat (suberoylanilide hydroxamic acid, SAHA, Zolinza), SB939 (Pracinostat), PCI-24781 (CRA-024781), JNJ-26481585 (Quisinostat), Romidepsin (FK228, FR901228, depsipeptide, NSC 630176), MGCD0103 (Mocetinostat), Entinostat (MS275), and combinations thereof.

15. The composition of any of statements 1-14, wherein the HDAC inhibitor is Entinostat (MS275), Trichostatin A (TSA), MS275 or a combination thereof.

16. The composition of any of statements 1-15, wherein the p300 activator is CTB, CTPB, TTK21, or any combination thereof.

17. The composition of any of statements 1-16, wherein the p300 activator is CTPB [N-(4-chloro-3-trifluoromethyl-phenyl)-2-ethoxy-6-pentadecyl-benzamide], CTB [N-(4-chloro-3-trifluoromethyl-phenyl)-2-ethoxybenzamide], or any combination thereof.

18. The composition of any of statements 1-17, wherein the p300 activator is N-(4-Chloro-3-(trilluoromethyl) phenyl)-2-ethoxybenzamide (CTB).

19. The composition of any of statements 1-18, wherein the PDE4 inhibitor is rolipram; enprofylline; theophylline; roflumilast; ariflo; tofimilast; pumafentrin; lirimilast; arofyllin; atizoram; D-4418; Bay-198004; Sch-351591; AWD-12-281; NCS-613; C1-1018; T-440; Tyrphostin AG 537; V-11294A; CDC-801; D-22888; YM-58997; Z-15370; N-(3,5-dichloro-1-oxo-pyridin-4-yl)-4-difluoromethoxy-3-cyclopropylmethoxybenzamide; (−)p-[(4aR*,10bS*)-9-ethoxy-1,2,3,4,4a,10b-hexahydro-8-methoxy-2-methylbenzo[s][1,6] naphthyridin-6-yl]-N,N-diisopropylbenzamide; (R)-(+)-1-(4-bromobenzyl)-4-[(3-cyclopentyloxy)-4-methoxyphenyl]-2-pyrrolidone; 3-(cyclopentyloxy-4-methoxyphenyl)-1-(4-N'-[N-2-cyano-S-methyl-isothioureido]benzyl)-2-pyrrolidone; cis[4-cyano-4-(3-cyclopentyloxy-4-methoxyphenyl)cyclohexane-1-carboxylic acid]; 2-carbomethoxy-4-cyano-4-(3-cyclopropylmethoxy-4-difluoromethoxy-phenyl) cyclohexan-1-one; cis[4-cyano-4-(3-cyclopropylmethoxy-4-difluoromethoxyphenyl) cyclohexan-1-ol]; (R)-(+)-ethyl[4-(3-cyclopentyloxy-4-methoxyphenyl)pyrrolidin-2-ylidene]acetate; (S)-(−)-ethyl[4-(3-cyclopentyloxy-4-methoxyphenyl) pyrrolidin-2-ylidene]acetate; 9-cyclopentyl-5,6-dihydro-7-ethyl-3-(2-thienyl)-9H-pyrazolo[3.4-c]-1,2,4-triazolo[4,3-a]pyridine; 9-cyclopentyl-5,6-dihydro-7-ethyl-3-(tert-butyl)-9H-pyrazolo[3.4-c]-1,2,4-triazolo[4.3-a]pyridine; or any combinations thereof.

20. The composition of any of statements 1-20, wherein the PDE4 inhibitor is Rolipram.

21. The composition of any of statements 1-21, wherein the Adenylyl cyclase agonist is Forskolin.

22. The composition of any of statements 1-22, wherein the RARγ agonist is CD1530; CD666; NRX204647; retinoic acid; all-trans retinoic acid (ATRA); 9-cis retinoic acid; all-trans 3-4 didehydro retinioc acid; 4-oxo retinoic acid; Retinol; 4-[(E)-2-(5,6,7,8-tetrahydro-5,5,8,8-tetramethyl-2-naphthalenyl)-1-propenyl]benzoic acid; 4-(5-methoxymethyl-5-methyl-2,3,4,5-tetrahydro-1-benzo[b]oxepin-8-yl-ethynyl)-benzoic acid; 4-(5-ethoxymethyl-5-methyl-2,3,4,5-tetrahydrobenzo[b]oxepin-8-ylethynyl)-benzoic acid; 4-(5-methyl-5-propoxymethyl-2,3,4,5-tetrahydrobenzo[b] oxepin-8-ylethynyl)-benzoic acid; (E)-4-[2-(5-methoxymethyl-5-propyl-2,3,4,5-tetrahydrobenzo[b] oxepin-8-yl)-vinyl]-benzoic acid; (E)-4-[2-(5-methoxymethyl-5-methyl-2,3,4,5-tetrahydrobenzo[b] oxepin-8-yl)-vinyl]-benzoic acid; (E)-4-[2-(5-methyl-5-propoxymethyl-2,3,4,5-tetrahydrobenzo[b]oxepin-8-yl)-vinyl]-benzoic acid; 4-(5-methoxymethyl-5-methyl-2,3,4,5-tetrahydrobenzo[b]thiepin-8-ylethynyl)-benzoic acid; 4-(5-ethoxymethyl-5-methyl-2,3,4,5-tetrahydrobenzo[b]thiepin-8-ylethynyl)-benzoic acid; (E)-4-[2-(5-ethoxymethyl-5-methyl-2,3,4,5-tetrahydrobenzo[b]thiepin-8-yl)-vinyl]-benzoic acid; (E)-4-[2-(5-methoxymethyl-5-propyl-2,3,4,5-tetrahydrobenzo[b]thiepin-8-yl)-vinyl]-benzoic acid; 4-(4-methoxymethyl-4-methyl-chroman-6-ylethynyl)-benzoic acid; (E)-4-[2-(4-methoxymethyl-4-methyl-chroman-6-yl)-vinyl]-benzoic acid; or any combination thereof.

23. The composition of any of statements 1-23, wherein the RARγ receptor agonist is CD1530.

24. The composition of any of statements 1-24, wherein the 5-HT3 antagonist is TDMB; Ondansetron; Granisetron; Tropisetron; Dolasetron; Palonosetron; Ramosetron; or any combination thereof.

25. The composition of any of statements 1-25, wherein the 5-HT3 antagonist is Tropanyl-3,5-dimethylbenzoate.

26. The composition of any of statements 1-26, wherein a metabotropic glutamate (mGlu) receptor agonist is ACPD; ACPT-1; AMN082; DCPG; GET73; LSP1-2111; Lu AF21934; Lu AF21935; Lu AF32615; LY354740; LY379268; LY2140023; LY459477; MMPIP; ML182; ML128; VU0155041; or any combination thereof.

27. The composition of any of statements 1-26, wherein the metabotropic glutamate (mGlu) receptor agonist is (1S,3R)-1-Aminocyclopentane-1,3-dic-arboxylic acid (ACPD).

28. The composition of any of statements 3-27, wherein the ROCK inhibitor Y27632 (4-[(1R)-1-aminoethyl]-N-pyridin-4-ylcyclohexane-1-carboxamide); 4-(2-pyridylcarbamoyl)piperidine; 1-benzyloxycarbonyl-4-(4-pyridylcarbamoyl)-piperidine; 1-benzoyl-4-(4-pyridylcarbamoyl)piperidine; 1-propyl-4-(4-pyridylcarbamoyl)piperidine; 1-[3-(2-(2-thienylmethyl)phenoxy)-2-hydroxypropyl]-4-(4-pyridylcarbamoyl)piperidine, 4-(4-pyridylcarbamoyl)piperidine; 1-benzyl-4-(4-pyridylcarbamoyl)-1,2,5,6-tetrahydropyridine; 3-(4-pyridylcarbamoyl)piperidine; 1-benzyl-3-(4-pyridylcarbamoyl)piperidine; 1-(2-(4-benzyloxyphenoxy)ethyl)-4-(N-(2-pyridyl)-N-benzyl-carbamoyl)piperidine; 1-formyl-4-(4-pyridylcarbamoyl)piperidine; 4-(3-pyridylcarbamoyl)piperidine; 1-isopropyl-4-(4-pyridylcarbamoyl)piperidine; 1-methyl-4-(4-pyridylcarbamoyl)piperidine; 1-hexyl-4-(4-pyridylcarbamoyl)piperidine; 1-benzyl-4-(4-pyridylcarbamoyl)piperidine; 1-(2-phenylethyl)-4-(4-pyridylcarbamoyl)piperidine; 1-(2-(4-methoxyphenyl)ethyl)-4-(4-pyridylcarbamoyl)-piperidine; 1-(2-(4-methoxyphenyl)ethyl)-4-(2-pyridylcarbamoyl)-piperidine; 1-(2-(4-chlorophenyl)ethyl)-4-(4-pyridylcarbamoyl)-piperidine; 1-diphenylmethyl-4-(2-pyridylcarbamoyl)piperidine; 1-[2-(4-(5-methyl-3-oxo-2,3,4,5-tetrahydropyridazin-6-yl)phenyl)ethyl]-4-(2-pyridylcarbamoyl)piperidine; 1-(4-(4,5-dihydro-2-furyl)phenyl)-4-(4-pyridylcarbamoyl)piperidine; 1-(2-nitrophenyl)-4-(4-pyridylcarbamoyl)piperidine; 1-(2-aminophenyl)-4-(4-pyridylcarbamoyl)piperidine; 1-nicotinoyl-4-(4-pyridylcarbamoyl)piperidine; 1-isonicotinoyl-4-(4-pyridylcarbamoyl)piperidine; 1-(3,4,5-trimethoxybenzoyl)-4-(4-pyridylcarbamoyl)-piperidine; 1-acetyl-4-(4-pyridylcarbamoyl)piperidine; 1-(3-(4-fluorobenzoyl)propyl)-4-(4-pyridylcarbamoyl)-piperidine; 1-(3-(4-fluorobenzoyl)propyl)-4-(2-pyridylcarbamoyl)-piperidine; 1-(1-(4-hydroxybenzoyl)ethyl)-4-(2-pyridylcarbamoyl)-piperidine; 1-(1-(4-benzyloxybenzoyl)ethyl)-4-(2-pyridylcarbamoyl)-piperidine; 1-(2-(4-hydroxyphenoxy)ethyl)-4-(2-pyridylcarbamoyl)-piperidine; 1-(4-(4-fluorophenyl)-4-hydroxy butyl)-4-(4-pyridylcarbamoyl)piperidine; 1-(1-methyl-2-(4-hydroxyphenyl)-2-hydroxyethyl)-4-(2-pyridylcarbamoyl)piperidine; 1-cinnamyl-4-(2-pyridylcarbamoyl)piperidine; 1-(2-hydroxy-3-phenoxypropyl)-4-(4-pyridylcarbamoyl)-piperidine; 1-(2-hydroxy-3-phenoxypropyl)-4-(3-pyridylcarbamoyl)-piperidine; 1-(2-hydroxy-3-phenoxypropyl)-4-(2-pyridylcarbamoyl)-piperidine; 1-(2-phenylethyl)-4-[N-(2-pyridyl)-N-(2-(N,N-dimethylamino)ethyl)carbamoyl]piperidine; 1-benzyloxycarbonyl-4-(2-pyridylcarbamoyl)piperidine; 1-(3-chloropheni)carbamoyl-4-(4-pyridylcarbamoyl)-piperidine; 4-[N-(2-pyridyl)-N-(2-(N,N-dimetliylamino)ethyl)-carbamoyl]piperidine; 1-methyl-4-(4-pyridylcarbamoyl)-1,2,5₅6-tetrahydropyridine; 1-nicotinoyl-3-(4-pyridylcarbamoyl)piperidine; 1-[2-(4-fluorobenzoyl)ethyl]-4-(4-pyridylcarbamoyl)-piperidine; 1-(6-chloro-2-methylimidazo[1,2-a]pyridine-3-carbonyl)-4-(4-pyridylcarbamoyl)piperidine; 1-(4-nitrobenzyl)-4-(4-pyridylcarbamoyl)piperidine; 1-hexyl-4-(4-pyridylcarbamoyl)piperidine; 1-benzyloxycarbonyl-4-(2-chloro-4-pyridylcarbamoyl)-piperidine; 4-(2-chloro-4-pyridylcarbamoyl)piperidine; 1-(2-chloronicotinoyl)-4-(4-pyridylcarbamoyl)piperidine; 3-(2-chloro-4-pyridylcarbamoyl)piperidine; 1-(4-phthalimidobutyl)-4-(4-pyridylcarbamoyl)piperidine; 1-(3,5-di-tert-butyl-4-hydroxycinnamoyl)-4-(4-pyridylcarbamoyl)piperidine; 1-carbamoylmethyl-4-(4-pyridylcarbamoyl)piperidine; 1-benzyloxycarbonyl-4-(5-nitro-2-pyridylcarbamoyl)-piperidine; 4-(5-nitro-2-pyridylcarbamoyl)piperidine; trans-4-benzyloxycarboxamidomethyl-1-(4-pyridylcarbamoyl)cyclohexane; trans-4-aminomethyl-1-(4-pyridylcarbamoyl)cyclohexane; trans-4-formamidomethyl-1-(4-pyridylcarbamoyty-cyclohexane; trans-4-dimethylaminomethyl-1-(4-pyridylcarbamoyl)-cyclohexane; N-benzylidene-trans-(4-pyridylcarbamoyl)-cyclohexylmethylamine; trans-4-benzylaminomethyl-1-(4-pyridylcarbamoyl)-cyclohexane; trans-4-isopropylaminomethyl-1-(4-pyridylcarbamoyl)-cyclohexane; trans-4-nicotinoylaminomethyl-1-(4-pyridylcarbamoyl)-cyclohexane; trans-4-cyclohexylaminomethyl-1-(4-pyridylcarbamoyl)-cyclohexane; trans-4-benzyloxycarboxamide-1-(4-pyridylcarbamoyl)-cyclohexane; trans-4-amino-1-(4-pyridylcarbamoyl)cyclohexane; trans-4-(1-aminoethyl)-1-(4-pyridylcarbamoyl)-cyclohexane; trans-4-aminomethyl-cis-2-methyl-1-(4-pyridylcarbamoyl)-cyclohexane; (+)-trans-4-(1-benzyloxycarboxamidopropyl)-1-cyclohexanecarboxylic acid; (+)-trans-4-(1-benzyloxycarboxamidopropyl)-1-(4-pyridylcarbamoyl)cyclohexane; (−)-trans-4-(1-benzyloxycarboxamidopropyl)-1-(4-pyridylcarbamoyl)cyclohexane; (+)-trans-4-(1-aminopropyl)-1-(4-pyridylcarbamoyl)-cyclohexane; (−)-trans-4-(1-aminopropyl)-1-(4-pyridylcarbamoyl)-cyclohexane; (−)-trans-4-(1-benzyloxycarboxamidoethyl)-1-(4-pyridylcarbamoyl)cyclohexane; (+)-trans-4-(1-benzyloxycarboxamidoethyl)-1-(4-pyridylcarbamoyl)cyclohexane; (+)-trans-4-(1-aminoethyl)-1-(4-pyridylcarbamoyl)-cyclohexane; (−)-trans-4-(1-aminoethyl)-1-(4-pyridylcarbamoyl)-cyclohexane; trans-4-(4-chlorobenzoyl)aminomethyl-1-(4-pyridylcarbamoyl)cyclohexane; trans-4-aminomethyl-1-(2-pyridylcarbamoyl)cyclohexane; trans-4-benzyloxycarboxamidomethyl-1-(2-pyridylcarbamoyl)cyclohexane; trans-4-methylaminotnethyl-1-(4-pyridylcarbamoyl)-cyclohexane; trans-4-(N-benzyl-N-methylamino)methyl-1-(4-pyridylcarbamoyl)cyclohexane; trans-4-aminomethyl-1-(3-pyridylcarbamoyl)cyclohexane; trans-4-aminomethyl-1-[(3-hydroxy-2-pyridyl)carbamoyl]-cyclohexane; trans-4-benzyloxycarboxamidomethyl-1-(3-pyridylcarbamoytycyclohexane; trans-4-benzyloxycarboxamidomethyl-1-[(3-benzyloxy-2-pyridyl)carbamoyl]cyclohexane; trans-4-phthalimidomethyl-1-(4-pyridylcarbamoyl)-cyclohexane; trans-4-benzyloxycarboxamidomethyl-1-(3-methyl-4-pyridylcarbamoyl)cyclohexane; trans-4- aminomethyl-1-(3-methyl-4-pyridylcarbamoyl)-cyclohexane; 4-(trans-4-benzyloxycarboxamidomethylcyclohexyl-carbonyl)amino-2,6-dimethylpyridine-N-oxide; 4-(trans-4-aminomethylcyclohexylcarbonyl)amino-2,6-dimethylpyridine-N-oxide; trans-4-aminomethyl-1-(2-methyl-4-pyridylcarbamoyl)-cyclohexane; trans-4-(1-benzyloxycarboxamidoethyl)-1-(4-pyridylcarbamoyl)cyclohexane; trans-4-(1-amino-1-methylethyl)-1-(4-pyridylcarbamoyl)-cyclohexane; trans-4-(2-aminoethyl)-1-(4-pyridylcarbamoyl)cyclohexane; trans-4-(2-amino-1-methylethyl)-1-(4-pyridylcarbamoyl)-cyclohexane; trans-4-(1-aminopropyl)-1-(4-pyridylcarbamoyl)-cyclohexane; trans-4-aminomethyl-trans-1-methyl-1-(4-pyridylcarbamoyl)cyclohexane; trans-4-benzylaminomethyl-cis-2-methyl-1-(4-pyridylcarbamoyl)cyclohexane; trans-4-(1-benzyloxycarboxamide-1-methylethyl)-1-(4-pyridylcarbamoyl)cyclohexane; trans-4-benzyloxycarboxamidomethyl-1-(N-methyl-4-pyridylcarbamoyl)cyclohexane; trans-4-(1-acetamide-1-methylethyl)-1-(4-pyridylcarbamoyl)cyclohexane; trans-N-(6-amino-4-pyrimidyl)-4-aminomethylcyclohexanecarboxamide; trans-N-(1H-pyrrolo[2,3-b]pyridin-4-yl)-4-aminomethylcyclohexane-carboxaniide; (+)-trans-N-(1H-pyrrolo[2,3-b]pyridin-4-yl)-4-(1-aminoethylcyclo-hexanecarboxamide; trans-N-(1H-pyrrolo[2,3-b]pyridin-4-yl)-4-(1-amino-1-methylethyl)cyclo-hexanecarboxamide; trans-N-(1H-pyrazolo[3,4-b]pyridin-4-yl)-4-aminomethylcyclohexanecarboxamide; (+)-trans-N-(1H-pyrazolo[3,4-b]pyridin-4-yl)-4-(1-aminoethyl)cyclo-hexanecarboxamide; trans-N-(1H-pyrazolo[3,4-b]pyridin-4-yl)-4-(1-amino-1-methylethyl)cyclo-hexanecarboxamide; (+)-trans-N-(2-amino-4-pyridyl)-4-(1-aminoethyl)-cyclohexanecarboxamide; trans-N-(1H-pyrazolo[3,4-d]pyrimidin-4-yl)-4-aminomethylcyclohexane-carboxamide; (+)-trans-N-(1H-pyrazolo[3,4-d]pyrimidin-4-yl)-4-(1-aminoethyl)cyclohexane carboxamide; trans-N-(1H-pyrazolo[3,4-d]pyrimidin-4-yl)-4-(1-amino-1-methylethyl)cyclohexane carboxamide; trans-N-(4-pyrimidinyl)-4-aminomethylcyclohexanecarboxamide; trans-N-(3-amino-4-pyridyl)-4-aminomethylcycloliexanecarboxamide; trans-N-(7H-imidazo[4,5-d]pyrimidin-6-yl)-4-aminomethylcyclo-hexanecarboxamide; trans-N-(3H-1,2,3-triazolo[4,5-d]-pyrimidin-7-yl)-4-aminomethyl-cyclohexane carboxamide; trans-N-(1-benzyl-1H-pyrazolo[3,4-b]pyridin-4-yl)-4-aminomethylcyclohexane; carboxamide trans-N-(1H-5-pyrazolyl)-4-aminomethylcyclo-hexanecarboxamide; trans-N-(1H-pyrazolo[3,4-b]pyridm-4-yl)-4-aminomethylcyclo-hexanecarboxamide; trans-N-(4-pyridazinyl)-4-aminomethylcyclohexanecarboxamide; trans-N-(7H-pyrrolo[2,3-d]pyrimidin-4-yl)-4-aminomethylcyclo-hexanecarboxamide; trans-N-(2-amino-4-pyridyl)-4-aminomethylcyclohexanecarboxamide; trans-N-(thieno[2,3-d]pyrimidin-4-yl)-4-aminomethylcyclohexan-ecarboxamide; trans-N-(5-methyl-1,2,4-triazolo[1,5-a]pyrimidin-7-yl)-4-aminomethyl-cyclohexane carboxamide; trans-N-(3-cyano-5-methylpyrazolo[1,5-a]pyrimidin-7-yl)-4-aminomethyl-cyclohexanecarboxamide; trans-N-(1H-pyrazolo[3,4-b]pyridin-4-yl)-4-(1-amino-1-methylethyl)cyclohexanecarboxamide; trans-N-(2-(1-pyrrolidinyl)-4-pyridyl)-4-aminomethylcyclohexanecarboxamide; trans-N-(2,6-diamino-4-pyrimidyl)-4-aminomethylcyclohexanecarboxamide; (+)-trans-N-(7-methyl-1,8-naphthyridin-4-yl)-4-(1-aminoethyl)cyclohexane-carboxamide; trans-N-(1-benzyloxymethylpyrrolo[2,3-b]pyridin-4-yl)-4-aminomethyl-cyclohexanecarboxamide; (+)-trans-N-(1-methylpyrrolo[2,3-b]pyridin-4-yl)-4-(1-aminoethyl)cyclo-hexanecarboxamide; trans-N-benzyl-N-(2-benzylamino-4-pyridyl)-4-(1-amino-1-methylethyl)-cyclohexanecarboxamide; trans-N-(2-azide-4-pyridyl)-4-aminomethylcyclohexanecarboxamide; trans-N-(2,3-dihydro-1H-pyrrolo[2,3-b]pyridin-4-yl)-4-aminomethyl-cyclohexanecarboxamide; trans-N-(2,3-dihydro-1H-pyrrolo[2,3-b]pyridin-4-yl)-4-(1-amino-1-methylethyl)cyclohexanecarboxamide; trans-N-(2-carboxy-4-pyridyl)-4-aminomethylcyclohexanecarboxamide; (R)-(+)-trans-N-(3-bromo-1H-pyrrolo[2,3-b]pyridin-4-yl)-4-(1-aminoethyl)cyclohexanecarboxamide; trans-N-(1H-pyrrolo[2,3-b]pyridin-4-yl)-4-guanidinomethylcyclohexanecarboxamide; trans-N-(1H-pyrazolo[3,4-b]pyridin-4-yl)-4-guanidinomethyl-cyclohexanecarboxamide; trans-N-(4-pyridyl)-4-guanidinomethylyclohexanecarboxamide; trans-N-(1-methylpyrrolo[2,3-b]pyridin-4-yl)-4-(guanidmomethyl)cyclo-hexanecarboxamide; trans-N-(1H-pyrrolo[2,3-b]pyridin-4-yl)-4-(2-imidazolin-2-yl)aminomethyl-cycloliexanecarboxamide; trans-N-(1-benzyloxymethylpyrrolo[2,3-b]pyridin-4-yl)-4-guanidinomethyl-cyclohexane-carboxamide; trans-N-(2-amino-4-pyridyl)-4-guanidinomethylcyclohexanecarboxamide; trans-N-(1-benzyloxymethyl-1H-pyrrolo[2,3-b]pyridin-4-yl)-4-(2-imidazolin-2-yl)aminomethylcyclohexanecarboxamide; trans-N-(1H-pyrrolo[2,3-b]pyridin-4-yl)-4-(3-benzylguanidinomethyl)cyclo-hexanecarboxamide; trans-N-(1H-pyrrolo[2,3-b]pyridin-4-yl)-4-(3-phenylguanidinomethyl)-cyclohexanecarboxamide; trans-N-(1H-pyrrolo[2,3-b]pyridin-4-yl)-4-(3-propylguanidinomethyl)-cyclohexanecarboxamide; trans-N-(1H-pyrrolo[2,3-b]pyridin-4-yl)-4-(3-octylguanidinomethyl)-cyclohexanecarboxamide; trans-N-(1-benzyloxymethylpyrrolo[2,3-b]pyridin-4-yl)-4-(2-benzyl-3-ethylguanidinomethyl)-cyclohexanecarboxamide; trans-N-(1H-pyrrolo[2,3-b]pyridin-4-yl)-4-(imidazol-2-yl)aminomethyl-cyclohexanecarboxamide; trans-N-(1H-pyrrolo[2,3-b]pyridin-4-yl)-4-(thiazol-2-yl)aminomethyl-cyclohexane carboxamide; (R)-(+)-N-(4-pyridyl)-4-(1-aminoethyl)benzamide; N-(4-pyridyl)-4-(1-amino-1-methylethyl)benzamide; N-(4-pyridyl)-4-aminomethyl-2-benzyloxybenzamide; N-(4-pyridyl)-4-aminomethyl-2-ethoxybenzamide; (R)-(−)-N-(4-pyridyl)-4-(1-aminoethyl)-3-nitrobenzamide; (R)-(−)-N-(4-pyridyl)-3-amino-4-(1-aminoethyl)benzamide; (R)-(+)-N-(4-pyridyl)-4-(1-aminoethyl)-3-chlorobenzamide; N-(4-pyridyl)-3-aminomethylbenzamide; (R)-(+)-N-(1H-pyrrolo[2,3-b]pyridin-4-yl)-4-(1-aminoethyl)benzamide; (R)-(+)-N-(1H-pyrazolo[3,4-]pyridin-4-yl)-4-(1-aminoethyl)benzamide; N-(1H-pyrazolo[3,4-b]pyridin-4-yl)-4-guanidinomethylbenzamide; N-(4-pyridyl)-4-guanidinomethylbenzamide; (R)-(+)-N-(4-pyridyl)-4-(1-aminoethyl)-3-fluorobenzamide; N-(4-pyridyl)-4-aminomethylbenzamide; N-(4-pyridyl)-4-aminomethyl-2-hydroxybenzamide; N-(4-pyridyl)-4-(2-aminoethyl)benzamide, N-(4-pyridyl)-4-aminomethyl-3-nitrobenzamide; N-(4-pyridyl)-

3amino-4-aminomnethylbenzamide; (S)-(−)-N-(4-pyridyl)-4-(1-aminoethyl)benzamide; (S)-(−)-N-(4-pyridyl)-2-(1-aminoethyl)benzamide; (R)-(+)-N-(4-pyridyl)-4-(1-aminoethyl)-2-chlorobenzamide; (R)-(+)-N-(1H-pyrrolo[2,3-b]pyridin-4-yl)-4-(1-(3-propylguanidino)ethyl)-benzamide; (R)-(−)-N-(1H-pyrrolo[2,3-b]pyridin-4-yl)-4-(1-aminoethyl)-3-azide-benzamide; (R)-(+)-N-(4-pyridyl)-4-(1-aminoethyl)-2-nitrobenzamide; (R)-(−)-N-(4-pyridyl)-4-(1-aminoethyl)-3-ethoxybenzamide; (R)-(+)-N-(3-iodo-1H-pyrrolo[2,3-b]pyridm-4-yl)-4-(1-ammoethyl)benzamide; (R)-(+)-N-(3-iodo-1H-pyrrolo[2,3-b]pyridin-4-yl)-4-(1-aminooethyl)-3-azidebenzamide; (R)-(−)-N-(4-pyridyl)-4-(1-aminoethyl)-3-hydroxybenzamide; N-(1H-pyrazolo[3,4-b]pyridin-4-yl)-4-guanidinomethyl-3-nitrobenzamide; (R)-N-(1H-pyrazolo[3,4-b]pyridin-4-yl)-4-(1-guanidinoethyl)-3-nitrobenzamide; (R)-N-(1H-pyrazolo[3,4-b]pyridin-4-yl)-4-(1-aminoethyl)-2-nitrobenzamide; N-(1H-pyrazolo[3,4-b]pyridin-4-yl)-4-guanidinobenzamide; (R)-N-(1H-pyrazolo[3,4-b]pyridin-4-yl)-4-(1-aminoethyl)-3-nitrobenzamide; (R)-N-(1H-pyrazolo[3,4-b]pyridin-4-yl)-4-(1-guanidinoethyl)benzamide; N-(1H-pyrazolo[3,4-b]pyridin-4-yl)-4-(1-amino-2-hydroxyethyl)benzamide; N-(1H-pyrazolo[3,4-b]pyridin-4-yl)-4-aminomethyl-3-nitrobenzamide; N-(1H-pyrrolo[2,3-b]pyridin-4-yl)-4-piperidinecarboxamide; N-(1H-pyrazolo[3,4-b]pyridin-4-yl)-4-piperidinecarboxamide; N-(1H-pyrazolo[3,4-b]pyridin-4-yl)-1-aminoacetyl-4-piperidine-carboxamide; N-(1-methoxymethyl-1H-pyrazolo[3,4-b]pyridin-4-yl)-4-piperidine-carboxamide; N-(2,3-dihydro-1H-pyrrolo[2,3-b]pyridin-4-yl)-4-piperidinecarboxamide; N-(1H-pyrrolo[2,3-b]pyridin-4-yl)-1-(2-phenylethyl)-4-piperidine-carboxamide; N-(1H-pyrrolo[2,3-b]pyridin-4-yl)-1-amidino-4-piperidinecarboxamide; N-(1H-pyrrolo[2,3-b]pyridin-4-yl)-1-(3-phenylpropyl)-4-piperidine-carboxamide; N-(1H-pyrrolo[2,3-b]pyridin-4-yl)-1-benzyl-4-piperidmecarboxamide; N-(1H-pyrazolo[3,4-b]pyridin-4-yl)-1-(2-phenylethyl)-4-piperidine-carboxamide; N-(1H-pyrazolo[3,4-b]pyridin-4-yl)-1-(3-phenylpropyl)-4-piperidine-carboxamide; N-(1H-pyrrolo[2,3-b]pyridin-4-yl)-4-(1-amino-1-methylethyl)benzamide; or any combination thereof.

29. The composition of any of statements 3-28, wherein the ROCK inhibitor Y27632 (4-[(1R)-1-aminoethyl]-N-pyridin-4-ylcyclohexane-1-carboxamide);

30. The composition of any of statements 3-29, wherein the neuronal differentiation enhancer is KHS2 (ethyl 4-(methyl(2-phenyl-4,5-dihydrothiazol-4-yl)amnino)benzoate); basic fibroblast growth factor (hFGF); fibroblast growth factor-8 (FGF-8); brain-derived neurotrophic factor (BDNF); Sonic Hedgehog (SHH); recombinant human insulin; human transferrin; sodium selenite; putrescine; progesterone; or any combination thereof.

31. The composition of any of statements 3-30, wherein the neuronal differentiation enhancer is KHS2

32. The composition of any of statements 3-31, wherein the an omega-3 fatty acid is docosahexaenoic acid; arachidonic acid; linolanic acid; linolenic acid; eicosapentaenoic acid; ethyl eicosapentaenoate (EPA-E); or any combination thereof.

33. The composition of any of statements 3-32, wherein the an omega-3 fatty acid is docosahexaenoic acid.

34. The composition of any of statements 3-33, wherein the A3 adenosine receptor agonists is IB-MECA; AB-MECA; (R)-PIA; (S)-PIA; AB-NECA; CCPA; [$^3$H] CCPA; CGS 21680; [$^3$]CGS 21680; CGS 24012; 2-chloroadenosine; 2-hexynyl-NECA; $N^6$-cyclopentyladenosine; NECA; (R,S)-PHPNECA; APNEA; IAB-MECA; Cyclopentyladenosine; LUF5831; Tecadenoson; or any combination thereof.

35. The composition of any of statements 3-34, wherein the A3 adenosine receptor agonists is IB-MECA.

36. The composition of any of statements 3-35, wherein the L-type calcium channel blocker is: Nitrendipine; Amlodipine; Felodipine; Isradipine; Lacidipine; Lercanidipine; Nicardipine; Nifedipine; Nimodipine; Nisoldipine; (+) isopropyl 2-methoxyethyl 4-(2-chloro-3-cyano-phenyl)-1,4-dihydro-2,6-dimethylpyridine-3,5-dicarboxylate; or any combination thereof.

37. The composition of any of statements 3-36, wherein the L-type calcium channel blocker is: Nitrendipine.

38. A composition consisting essentially of the following compounds: CHIR99021 (GSK3 inhibitor), SB431542 (ALK4/5/7 inhibitor), MS275 (HDAC1 inhibitor), CTB (p300 activator), Rolipram (PDE4 inhibitor), Forskolin (Adenylyl cyclase agonist), CD1530 (RARγ receptor agonist), TDMB (Tropanyl-3,5-dimethylbenzoate, 5-HT3 antagonist), and ACPD (mGlu receptor agonist).

39. A composition comprising the following compounds: a ROCK inhibitor, a neuronal differentiation enhancer, an omega-3 fatty acid, an A3 adenosine receptor agonist, or an L-type calcium channel blocker.

40. A composition consisting essentially of the following compounds: Y27632 (ROCK inhibitor), KHS2 (neuronal differentiation enhancer), DHA (an omega-3 fatty acid), IB-MECA (A3 adenosine receptor agonist), and Nitrendipine (L-type calcium channel blocker).

41. The composition of statement 39, containing at least two of the compounds, or at least three of the compounds, or at least four of the compounds.

42. The composition of any of statements 1-41, further comprising a physiologically acceptable excipient or carrier.

43. The composition of any of statements 1-42, wherein the composition is a cell reprogramming composition.

44. The composition of any of statements 1-43, wherein the agent(s) or compound(s) is present in an amount sufficient to reprogram a cell into a neuronal cell type.

45. The composition of any of statements 1-44, wherein the agent(s) or compound(s) is present in an amount sufficient to induce a cell to express Tuj1.

46. The composition of any of statements 1-45, wherein the agent(s) or compound(s) is present in an amount sufficient to induce a cell to express Tau.

47. The composition of any of statements 1-46, wherein the agent(s) or compound(s) is present in an amount sufficient to induce a cell to express NeuN.

48. The composition of any of statements 1-47, wherein the agent(s) or compound(s) is present in an amount sufficient to induce a cell to express MAP2.

49. The composition of any of statements 1-48, wherein the agent(s) or compound(s) is present in an amount sufficient to induce a cell to express Synapsin.

50. The composition of any of statements 43-49, wherein the cell is a non-neuronal cell.

51. The composition of any of statements 43-50, wherein the cell is a differentiated cell.

52. The composition of any of statements 43-51, wherein the cell is a somatic cell.
53. The composition of any of statements 43-52, wherein the cell is an adult cell.
54. The composition of any of statements 43-53, wherein the cell is a multipotent, unipotent, or progenitor cell.
55. The composition of any of statements 43-54, wherein the cell is a newborn cord blood cell, or a newborn stem cell.
56. The composition of any of statements 43-55, wherein the cell s an allogenic or autologous cell.
57. The composition of any of statements 43-56, wherein the cell is a heterogeneous or homogeneous mixture of cells.
58. A method of generating a neuronal cell comprising contacting a selected cell with the composition of any of statements 1-57, to thereby generate a neuronal progenitor cell.
59. The method of statement 58, wherein the selected cell is a population of cells contacted with the composition.
60. The method of statement 58 or 59, wherein the selected cell is a differentiated cell.
61. The method of any of statements 58-60, wherein the selected cell is a non-neuronal cell.
62. The method of any of statements 58-61, wherein the selected cell is a somatic cell.
63. The method of any of statements 58-62, wherein the selected cell is a heterogeneous or homogeneous mixture of cells.
64. The method of any of statements 58-63, wherein the selected cell is an adult cell.
65. The method of any of statements 58-64, wherein the selected cell is a multipotent, unipotent, or progenitor cell.
66. The method of any of statements 58-65, wherein the selected cell is a newborn cord blood cell, or a newborn stem cell.
67. The method of any of statements 58-66, wherein the selected cell is an allogenic or autologous cell.
68. The method of any of statements 58-67, wherein the selected cell expresses a heterologous miR124.
69. The method of any of statements 58-68, wherein the cell comprises a heterologous nucleic acid comprising a segment encoding miR124 operably linked to a promoter.
70. The method of statement 69, wherein the promoter is heterologous to the segment encoding miR124.
71. The method of any of statements 58-70, wherein the selected cell is contacted with the composition for a time and/or with an amount of each agent sufficient to induce the selected cell to express Tuj1.
72. The method of any of statements 58-71, wherein the selected cell is contacted with the composition for a time and/or with an amount of each agent sufficient to induce the selected cell to express Tau.
73. The method of any of statements 58-72, wherein the selected cell is contacted with the composition for a time and/or with an amount of each agent sufficient to induce the selected cell to express NeuN.
74. The method of any of statements 58-73, wherein the selected cell is contacted with the composition for a time and/or with an amount of each agent sufficient to induce the selected cell to express MAP2.
75. The method of any of statements 58-74, wherein the selected cell is contacted with the composition for a time and/or with an amount of each agent sufficient to induce the selected cell to express Synapsin.
76. The method of any of statements 58-75, furthering comprising administering the neuronal cell to a subject.
77. The method of any of statements 58-76, furthering comprising administering at least about 100 of the neuronal cells to a subject.
78. The method of any of statements 58-77, comprising administering at least about 1000, or at least about 10,000, or at least about 100,000, or at least about 1,000,000, or at least about 10,000,000, or at least about 100,000,000 of the neuronal cells to a subject.
79. The method of any of statements 72-78, wherein the neuronal cell(s) is/are allogenic or autologous cell(s).
80. The method of any of statements 72-79, wherein the neuronal cell(s) is/are neuronal progenitor cells.
81. The method of any of statements 72-80, wherein the neuronal cell(s) is/are mature neuronal cells.
82. The method of any of statements 72-81, wherein the subject suffers or is suspected of suffering from Amyotrophic lateral sclerosis (ALS), Alzheimer's disease, Parkinson's disease, multiple sclerosis, Primary lateral sclerosis (PLS), Progressive bulbar palsy, Pseudobulbar palsy, Primary lateral sclerosis (PLS), Progressive muscular atrophy, Spinal muscular atrophy (SMA), including Type I (also called Werdnig-Hoffmann disease), Type II, Type III (Kugelberg-Welander disease), Fazio-Londe disease, Huntington's disease, Kennedy's disease also known as progressive spinobulbar muscular atrophy, hereditary spastic paraplegia (HSP), congenital SMA with arthrogryposis, Post-polio syndrome (PPS), traumatic spinal cord injury, progressive pseudobulbar palsy, progressive muscular atrophy, stroke, head trauma, spinal cord injury, or a combination thereof.
83. A method comprising administering the composition of any of statements 1-57, to a subject.
84. The method of statement 83, wherein the composition contains one or more neuronal progenitor cells and/or one or more mature neuronal cells.
85. The method of statement 83 or 84, wherein the composition contains one or more allogenic or autologous cell.
86. The method of any of statements 83-85, wherein the composition contains one or more, or at least about 1000, cells that express Tuj1.
87. The method of any of statements 83-86, wherein the composition contains one or more, or at least about 1000, cells that express Tau.
88. The method of any of statements 83-87, wherein the composition contains one or more, or at least about 1000, cells that express NeuN.
89. The method of any of statements 83-88, wherein the composition contains one or more, or at least about 1000, cells that express MAP2.
90. The method of any of statements 83-89, wherein the composition contains one or more, or at least about 1000, cells that express Synapsin.
91. The method of any of statements 83-90, wherein the composition contains at least about 1000, or at least about 10,000, or at least about 100,000, or at least about 1,000,000, or at least about 10,000,000, or at least about 100,000,000 neuronal cells.
92. The method of any of statements 83-91, wherein the subject is in need of administration of the composition.
93. The method of any of statements 83-92, wherein the subject is in need of neuronal progenitor cells or mature neuronal cells.

94. The method of any of statements 83-93, wherein the composition is administered for a time and/or with an amount of each agent sufficient to reduce the symptoms of a neuronal condition or disease.
95. The method of any of statements 83-94, wherein the subject suffers or is suspected of suffering from Amyotrophic lateral sclerosis (ALS), Alzheimer's disease, Parkinson's disease, multiple sclerosis, Primary lateral sclerosis (PLS), Progressive bulbar palsy, Pseudobulbar palsy, Progressive muscular atrophy, Spinal muscular atrophy (SMA), including Type I (also called Werdnig-Hoffmann disease), Type II, Type III (Kugelberg-Welander disease), Fazio-Londe disease, Huntington's disease, Kennedy's disease also known as progressive spinobulbar muscular atrophy, hereditary spastic paraplegia (HSP), congenital SMA with arthrogryposis, Post-polio syndrome (PPS), traumatic spinal cord injury, progressive pseudobulbar palsy, progressive muscular atrophy, stroke, head trauma, spinal cord injury, or a combination thereof.
96. A kit comprising the composition of any of statements 1-57, and instructions for using the composition.
97. The kit of statement 96, further comprising components for in vitro cell culture of a selected cell.
98. The kit of statement 96 or 97, further comprising one or more cell collection devices (e.g., one or more sterile cell collection devices).
99. The kit of any of statements 96-98, further comprising cell culture medium, or a supplementary factor.
100. The kit of any of statement 96-99, further comprising a population of neuronal cells generated by contacting the cells with the composition.
101. The kit of any of statements 96-100, further comprising a diluent, a pharmaceutically acceptable carrier, a syringe, a catheter, or a device for delivery of cells or of the composition.
102. The kit of any of statements 96-101, further comprising antibodies, probes, or primers for detection of a neuronal progenitor cell marker.
103. The kit of statement 102, wherein the marker is Tuj1, Tau, NeuN, MAP2, synapsin, or any combination thereof.

What is claimed:

1. A method of generating a neuronal cell comprising incubating a selected population of non-pluripotent, non-neuronal cells with the composition comprising CHIR99021, an ALK5 and ALK4 inhibitor, a histone deacetylase inhibitor, and a p300 activator, to thereby generate neuronal cells, neuronal progenitor cells, or a combination thereof without de-differentiating the population of non-pluripotent, non-neuronal cells into a population of cells exhibiting pluripotent stem cell characteristics.

2. The method of claim 1, wherein the selected population of non-pluripotent, non-neuronal cells contacted with the composition comprises a somatic cell, a differentiated cell, a heterogeneous mixture of cells, or a combination thereof.

3. The method of claim 2, wherein the population of cells comprises cells from the spinal cord or brain.

4. The method of claim 1, wherein the selected population of non-pluripotent, non-neuronal cells comprises newborn cord blood cells.

5. The method of claim 1, wherein the composition comprises about 0.01 micromolar to about 20 millimolar CHIR99021, about 0.01 micromolar to about 20 millimolar ALK5 and ALK4 inhibitor, about 0.001 micromolar to about 20 millimolar histone deacetylase inhibitor, and about 0.001 micromolar to about 20 millimolar p300 activator.

6. The method of claim 1, further comprising administering the neuronal cells, neuronal progenitor cells, or a combination thereof to a subject.

7. The method of claim 6, wherein the population of non-pluripotent, non-neuronal cells comprises allogenic or autologous cells.

8. The method of claim 6, wherein the subject suffers or is suspected of suffering from Amyotrophic lateral sclerosis (ALS), Alzheimer's disease, Parkinson's disease, multiple sclerosis, Primary lateral sclerosis (PLS), Progressive bulbar palsy, Pseudobulbar palsy, Primary lateral sclerosis (PLS), Progressive muscular atrophy, Spinal muscular atrophy (SMA), Werdnig-Hoffmann disease, Kugelberg-Welander disease, Fazio-Londe disease, Huntington's disease, Kennedy's disease also known as progressive spinobulbar muscular atrophy, hereditary spastic paraplegia (HSP), congenital SMA with arthrogryposis, Post-polio syndrome (PPS), traumatic spinal cord injury, progressive pseudobulbar palsy, progressive muscular atrophy, stroke, head trauma, spinal cord injury, or a combination thereof.

9. The method of claim 1, wherein the composition further comprises a PDE4 inhibitor, an Adenylyl cyclase agonist, a retinoic acid receptor γ agonist, a 5-HT3 antagonist, and a metabotropic glutamate (mGlu)receptor agonist.

10. The method of claim 1, wherein the composition further comprises one or more of the following compounds: a ROCK inhibitor, a neuronal differentiation enhancer, an omega-3 fatty acid, an A3 adenosine receptor agonist or an L-type calcium channel blocker.

11. The method of claim 1, wherein the composition comprises the following compounds: CHIR99021, SB431542, MS275, N-(4-chloro-3-trifluoromethyl-phenyl)-2-ethoxybenzamide (CTB), Rolipram, Forskolin, CD1530, Tropanyl-3,5-dimethylbenzoate, and (1S,3R)-1-Aminocyclopentane-1,3-dic-arboxylic acid (ACPD).

12. The method of claim 1, wherein the composition comprises the following compounds: CHIR99021, SB431542, MS275, N-(4-chloro-3-trifluoromethyl-phenyl)-2-ethoxybenzamide (CTB), Rolipram, Forskolin, CD1530, Tropanyl-3,5-dimethylbenzoate, and (1S,3R)-1-Aminocyclopentane-1,3-dicarboxylic acid (ACPD).

13. The method of claim 1, wherein the composition comprises the following compounds: SB431542, Trichostatin A, Rolipram, CHIR99021, and N-(4-chloro-3-trifluoromethyl-phenyl)-2-ethoxy-6-pentadecyl-benzamide (CTPB).

* * * * *